(12) United States Patent
Harada

(10) Patent No.: US 11,419,749 B2
(45) Date of Patent: Aug. 23, 2022

(54) ADHESIVE PLASTER STRUCTURE FOR TREATING WOUNDS CAUSED BY INGROWN NAILS

(71) Applicant: Neostyle B Co., Ltd., Tokyo (JP)

(72) Inventor: Masanori Harada, Kitakyushu (JP)

(73) Assignee: NEOSTYLE B CO., LTD., Tokyo (JP)

( * ) Notice: Subject to any disclaimer, the term of this patent is extended or adjusted under 35 U.S.C. 154(b) by 273 days.

(21) Appl. No.: 15/515,150

(22) PCT Filed: Nov. 9, 2015

(86) PCT No.: PCT/JP2015/081434
§ 371 (c)(1),
(2) Date: Mar. 29, 2017

(87) PCT Pub. No.: WO2016/076248
PCT Pub. Date: May 19, 2016

(65) Prior Publication Data
US 2017/0216079 A1    Aug. 3, 2017

(30) Foreign Application Priority Data

Nov. 10, 2014 (JP) .............................. JP2014-228328
Jul. 17, 2015 (WO) .................. PCT/JP2015/070539

(51) Int. Cl.
*A61F 5/00* (2006.01)
*A61F 5/11* (2006.01)
(Continued)

(52) U.S. Cl.
CPC ....... *A61F 5/11* (2013.01); *A61F 5/00* (2013.01); *A61F 5/01* (2013.01); *A61F 13/105* (2013.01);
(Continued)

(58) Field of Classification Search
CPC ...... A61F 5/11; A61F 5/00; A61F 5/01; A61F 13/105; A61F 13/104; A61F 5/019;
(Continued)

(56) References Cited

U.S. PATENT DOCUMENTS 1,596,532 A * 8/1926 Haener ...................... A61F 5/11
602/31
2,499,851 A * 3/1950 Cronholm ................. A61F 5/11
602/31
(Continued)

FOREIGN PATENT DOCUMENTS

CN       101873840 A     10/2010
CN       202446313 U      9/2012
(Continued)

OTHER PUBLICATIONS

"Solid," Volcabulary.com, https://www.vocabulary.com/dictionary/solid.*
(Continued)

*Primary Examiner* — Victoria Hicks Fisher
(74) *Attorney, Agent, or Firm* — KDB Firm PLLC

(57) ABSTRACT

An adhesive plaster structure 1 attached to a finger or a toe along a lateral nail edge, the adhesive plaster structure 1 has: a wound adhesion area 2 having a flexible wound adhesion surface 2A; and a guide area 3 having a slide groove 3A that receives the lateral nail edge, the slide groove being capable of sliding in a longitudinal direction of a nail along the lateral nail edge, wherein the slide groove 3A extends at least over a part of a length between the tip portion and the rear end portion of the adhesive plaster structure 1 in the longitudinal direction of the adhesive plaster structure 1, and the flexible wound adhesion surface is guided to a position of the wound caused by the ingrown nail when the adhesive plaster structure 1 is attached to the finger or the toe.

6 Claims, 48 Drawing Sheets

(51) Int. Cl.
  *A61F 13/10* (2006.01)
  *A61F 5/01* (2006.01)
  *A61F 5/058* (2006.01)
  *A61F 13/04* (2006.01)
(52) U.S. Cl.
  CPC ........... *A61F 5/019* (2013.01); *A61F 5/05875* (2013.01); *A61F 13/04* (2013.01)
(58) Field of Classification Search
  CPC .. A61F 5/05875; A61F 5/05866; A61F 13/04; A61F 2013/00353; A61F 13/10; A61F 2013/0048; A61F 2013/00089; A61F 2013/00093; A61F 2013/00361; A61F 2013/00365
  USPC .............................. 602/31, 30; 128/893, 894
  See application file for complete search history.

(56) References Cited

U.S. PATENT DOCUMENTS

| | | | |
|---|---|---|---|
| 2,542,324 A * | 2/1951 | Gibbons | A61F 5/11 602/31 |
| 2,920,621 A * | 1/1960 | Fettig | A61F 5/11 602/31 |
| 4,057,055 A | 11/1977 | Clark | |
| 5,613,503 A | 3/1997 | Penner | |
| 6,095,995 A | 8/2000 | Machida | |
| 2004/0260221 A1* | 12/2004 | Machida | A61F 5/11 602/30 |
| 2006/0189909 A1* | 8/2006 | Hurley | A61F 13/063 602/41 |
| 2007/0287945 A1* | 12/2007 | Cha | A61F 5/11 602/31 |
| 2010/0137771 A1 | 6/2010 | Harada | |
| 2010/0160845 A1* | 6/2010 | Yoshikawa | A61F 5/11 602/31 |
| 2010/0262058 A1* | 10/2010 | Stolz | A61F 5/11 602/31 |
| 2010/0268143 A1 | 10/2010 | Kojima | |
| 2012/0197172 A1* | 8/2012 | Ogawa | A61F 5/11 602/31 |
| 2017/0020709 A1 | 1/2017 | Harada | |

FOREIGN PATENT DOCUMENTS

| | | | |
|---|---|---|---|
| CN | 203790112 U | 8/2014 | |
| EP | 1477144 A2 * | 11/2004 | ................ A61F 5/11 |
| EP | 1477144 A2 | 11/2004 | |
| GB | 928885 | 6/1963 | |
| GB | 2147211 A | 5/1985 | |
| JP | H08-215227 A | 8/1996 | |
| JP | 2001-276104 A | 10/2001 | |
| JP | 2002-360619 A | 12/2002 | |
| JP | 2002360619 A | 12/2002 | |
| JP | 2004-329646 A | 11/2004 | |
| JP | 2004329646 A | 11/2004 | |
| JP | 2008-531130 A | 8/2008 | |
| JP | 2008531130 A | 8/2008 | |
| JP | 2011-104231 A | 6/2011 | |
| JP | 2012-125527 A | 7/2012 | |
| JP | 2012-176228 A | 9/2012 | |
| JP | 2013-081723 A | 5/2013 | |
| JP | 5579913 B | 8/2014 | |
| WO | 2008/142880 A | 11/2008 | |
| WO | 2009072456 A1 | 6/2009 | |
| WO | WO2009/072456 A | 6/2009 | |

OTHER PUBLICATIONS

International Search Report for PCT/JP2015/081434 dated Dec. 15, 2015.
PCT written opinion dated Dec. 15, 2015.
Japanese decision to grant a patent dated Aug. 2, 2016.

\* cited by examiner

ADHESIVE PLASTER STRUCTURE FOR TREATING WOUNDS CAUSED BY INGROWN NAILS

TECHNICAL FIELD

The present invention relates to an adhesive plaster structure for treating wounds caused by ingrown nails. In more detail, the present invention relates to an adhesive plaster structure attached to a finger/toe along a lateral nail edge for treating wound caused by ingrown nail, the adhesive plaster structure comprising: (i) a wound adhesion area having a flexible wound adhesion surface to be adhered to the wound caused by the ingrown nail; and (ii) a guide area having a slide groove that receives the lateral nail edge, the slide groove being capable of sliding in a longitudinal direction of a nail along the lateral nail edge, wherein the adhesive plaster structure has an approximately rod shape, the slide groove extends at least over a part of a length between the tip portion and the rear end portion of the adhesive plaster structure in the longitudinal direction of the adhesive plaster structure, and the flexible wound adhesion surface is guided to a position of the wound caused by the ingrown nail when the adhesive plaster structure is attached to the finger/toe. When the adhesive plaster structure of the present invention is used, because of a linkage between the wound adhesion area and the guide area, the wound of the ingrown nail can be surely treated also near the root of the nail in addition to near the tip of the nail regardless of degree of the deformation of the ingrown nail and severity of pain of the wound caused by the ingrown nail. In the conventional technology, the root of the nail could not be treated effectively and efficiently. By using the present invention, the wound caused by the ingrown nail can be treated effectively and efficiently and pain of the wound caused by the ingrown nail can be relieved rapidly and drastically. (Namely, the wound can be immediately cured.) Furthermore, the adhesive plaster structure of the present invention has a function of assisting to correct the ingrown nail since an effect of correcting the ingrown nail is provided by an effect of pushing up the lateral nail edge (lateral edge of the nail).

BACKGROUND ART

Nail deformity includes "rolled nail" and "ingrown nail." Frequently, the word of the rolled nail and the word of the ingrown nail are used without being distinguished from each other. However, in general, a state as if the nail is rolled laterally is called as "rolled nail," and a state that the nail is significantly curved and both ends of the nail are growing into skin or flesh (soft tissue) is called as "ingrown nail" in many cases. In the present invention, hereafter, unless otherwise specified, the term of "ingrown nail" is used as a general term of the nail deformity causing wound and pain to the finger/toe of the patient. In case of the ingrown nail, one or both sides of lateral edges of the nail are deeply growing into a nail groove along with the growth of the nail, and stuck in the soft tissue (flesh of nail groove and nail bed) causing inflammation accompanying pain or severe pain. When the ingrown nail becomes serious, the inflammation spreads to the root of the nail and pain is increased. The ingrown nail is mainly caused by pressure, wound, overcut and birth defect, for example. The ingrown nail frequently occurs especially on a big toe. As the conventional methods for curing the ingrown nail, a method of removing the lateral edge of the nail ingrown in the nail groove by a surgical operation, and a method of using a corrector or a correcting device are known. As the method of using the corrector and the correcting device, for example, U.S. Pat. No. 4,057,055 (Patent Document 1), Japanese Unexamined Patent Application Publication No. H08-215227 (Patent Document 2), Japanese Unexamined Patent Application Publication No. 2001-276104 (Patent Document 3), Japanese Unexamined Patent Application Publication No. 2011-104231 (Patent Document 4), Japanese Unexamined Patent Application Publication No. 2002-360619 (Patent Document 5), International Patent Application Publication No. WO2008-142880 (Patent Document 6), and Japanese Patent No. 5579913 (Patent Document 7) can be seen.

However, the method of using the surgical operation is complicated and the width of the nail plate becomes narrow permanently after the operation. Furthermore, in the method of using the surgical operation, the nail growing into the soft tissue is partly cut and removed. Thus, the operation is difficult when there is a risk of bacterial infection. Even if the ingrown nail is temporarily cured by the surgical operation by partly removing the nail, tendency of curling in a curling direction is not corrected as whole the nail. Thus, the ingrown nail often occurs again after the operation. Consequently, it is now generally thought that a method not using the surgical operation, i.e. a conservative method, is preferable as the method for curing the ingrown nail.

In the methods of using the corrector and the correcting device disclosed in Patent Documents 1 to 7, the ingrown nail (deformed nail) itself can be corrected pretty well by using some of these methods. However, all methods disclosed in Patent Documents 1 to 7 do not directly provide a therapeutic effect to the wound caused by the ingrown nail. Accordingly, in general, the wound caused by the ingrown nail cannot be treated effectively and efficiently by any methods disclosed in Patent Documents 1 to 7. In addition, the pain cannot be relieved rapidly and drastically. (Namely, the wound cannot be immediately cured.)

As the conventionally known method for curing the wound caused by the ingrown nail, a method of applying an adhesive plaster or the like on the wound and a method of covering a lateral edge portion (lateral nail edge) of the ingrown nail by a metal body or a resin body having a long shape are known. As the method of applying the adhesive plaster or the like on the wound caused by the ingrown nail, for example, Japanese Unexamined Patent Application Publication No. 2012-125527 (Patent Document 8) and Japanese Unexamined Patent Application Publication No. 2013-81723 (Patent Document 9) can be seen. As the method of covering the lateral edge portion of the ingrown nail by the metal body or the resin body having a long shape, Japanese Unexamined Patent Application Publication No. 2004-329646 (Patent Document 10) and U.S. Unexamined Patent Application Publication No. 2007/0287945A1 (Patent Document 11) can be seen.

The adhesive plaster or the like used in the method of Patent Document 8 and Patent Document 9 has a structure substantially same as the structure of normal first-aid adhesive plaster except for that the position of a wound contact pad (a portion to cover the wound) is slightly different from that of the normal first-aid adhesive plaster. As is clear from the drawings of Patent Document 8 and Patent Document 9, the wound of the ingrown nail can be cured at a portion near the tip, but it is substantially impossible to cure the wound of the ingrown nail at a portion near the root by the method described in Patent Document 8 and Patent Document 9. As described above, when the ingrown nail becomes serious, the inflammation spreads to the root of the nail and pain is increased. Therefore, if it is substantially impossible to cure the wound of the ingrown nail at a portion near the root, it is substantially impossible to cure the serious wound caused by the ingrown nail. Accordingly, the wound caused by the ingrown nail cannot be treated effectively and efficiently by the methods disclosed in Patent Document 8 and Patent Document 9. In addition, the pain cannot be relieved rapidly and drastically. (Namely, the wound cannot be immediately cured.)

Patent Document 10 (Japanese Unexamined Patent Application Publication No. 2004-329646) discloses "ingrown nail correcting tool" including a tubular body made of a hard material and formed in a C-shaped cross-section. The ingrown nail correcting tool is attached to a finger/toe by inserting the lateral edge portion (lateral nail edge) of the ingrown nail into a gap portion of the C-shaped cross-section. When the ingrown nail correcting tool is attached to the finger/toe, the lateral edge portion of the ingrown nail is covered by the tubular body. Thus, if the wound caused by the ingrown nail is not serious, pain of the wound is slightly reduced with the lapse of time. However, the ingrown nail correcting tool of Patent Document 10 does not have structural characteristics for actively treating the wound caused by the ingrown nail. Accordingly, the ingrown nail correcting tool does not directly provide a therapeutic effect to the wound caused by the ingrown nail and it is substantially impossible to cure the serious wound caused by the ingrown nail. As explained above, the wound caused by the ingrown nail cannot be treated effectively and efficiently ingrown nail by the correcting tool disclosed in Patent Document 10. In addition, the pain cannot be relieved rapidly and drastically. (Namely, the wound cannot be immediately cured.)

An essential point of a method disclosed in Patent Document 11 is that the lateral nail fold closely contacted with the lateral edge portion of the ingrown nail is laterally pushed and moved by a finger to expose the lateral edge portion of the ingrown nail and the wound site and then the lateral edge portion of the ingrown nail is covered by a long soft resin piece (referred to as "protecting gutter") formed in a U-shape. Thus, the lateral edge portion of the ingrown nail and the wound site are separated with each other for facilitating wound healing. However, in this case, when the ingrown nail is serious, the wound site and surrounding area are terribly swollen by severe inflammation and seems painful. Thus, when the lateral nail fold closely contacted with and pressed to the lateral edge portion of the ingrown nail is laterally pushed and moved by a finger, large pain is accompanied. In addition, even when the lateral nail fold is laterally pushed and moved forcefully as described above, the exposed space is very small and enough space cannot be provided, and body fluid such as pus and lymph exudes to obstruct visual field in many cases. Accordingly, it is not easy even for a skilled operator to correctly and surely cover the soft resin piece on an entire length of the lateral edge portion of the ingrown nail (entire length in the longitudinal direction of the nail). Furthermore, as described above, when the ingrown nail becomes serious, the inflammation spreads to the root of the nail and pain is increased. The root portion of the nail is covered by a posterior nail fold (regardless of whether the nail is the ingrown nail or not). As explained above, in the method described in Patent Document 11, it is substantially impossible to surely cover the lateral edge portion of the ingrown nail by the soft resin piece near the root portion of the nail. Thus, it is substantially impossible to cure the wound (serious wound caused by the ingrown nail) at a portion near the root. Accordingly, the wound caused by the ingrown nail cannot be treated effectively and efficiently by the method disclosed in Patent Document 11. In addition, the pain cannot be relieved rapidly and drastically. (Namely, the wound cannot be immediately cured.)

PRIOR ART DOCUMENTS

Patent Documents

Patent Document 1: U.S. Pat. No. 4,057,055
Patent Document 2: Japanese Unexamined Patent Application Publication No. H08-215227
Patent Document 3: Japanese Unexamined Patent Application Publication No. 2001-276104
Patent Document 4: Japanese Unexamined Patent Application Publication No. 2011-104231
Patent Document 5: Japanese Unexamined Patent Application Publication No. 2002-360619
Patent Document 6: International Patent Publication No. WO2008-142880
Patent Document 7: Japanese Patent No. 5579913
Patent Document 8: Japanese Unexamined Patent Application Publication No. 2012-125527
Patent Document 9: Japanese Unexamined Patent Application Publication No. 2013-81723
Patent Document 10: Japanese Unexamined Patent Application Publication No. 2004-329646
Patent Document 11: U.S. Unexamined Patent Application Publication No. 2007/0287945A1

SUMMARY OF THE INVENTION

Problems to be Solved by the Invention

As described above, in the conventional methods (methods for correcting the ingrown nail) by using the correcting tool or the correcting device, a therapeutic effect is not directly provided to the wound caused by the ingrown nail. Thus, it is impossible to treat the wound effectively and efficiently and remove the pain rapidly and drastically. In addition, as described above, even when the conventional method of applying the adhesive plaster or the like on the wound and the conventional method of covering the lateral edge portion of the ingrown nail by the metal body or the resin body having a long shape are used, it is substantially impossible to cure the wound (serious wound caused by the ingrown nail) at a portion near the root. Accordingly, it is impossible to treat the wound caused by the ingrown nail effectively and efficiently and remove the pain rapidly and drastically. To solve the above described problems of the conventional technology, it is desired to provide a treatment tool and a treatment method that enable to surely treat the ingrown nail also near the root of the nail in addition to near the tip of the nail regardless of degree of the deformation of the ingrown nail and severity of pain of the wound caused by the ingrown nail although it was difficult in the conventional technology, enable to surely treat the wound caused by the ingrown nail can be treated effectively and efficiently, and enable to relieve pain of the wound caused by the ingrown nail rapidly and drastically (i.e., cure the wound immediately). In other words, briefly, it is desired to develop a technology surely and rapidly curing the wound and pain caused by the ingrown nail regardless of degree of seriousness of the ingrown nail and the position of the wound caused by the ingrown nail in the longitudinal direction of the nail.

Means for Solving Problem

In such a situation, as a result of intensive research to solve the above described problem, the inventor found that the problem could be solved by an adhesive plaster structure attached to a finger/toe along a lateral nail edge for treating wound caused by ingrown nail, the adhesive plaster structure comprising: (i) a wound adhesion area having a flexible wound adhesion surface to be adhered to the wound caused by the ingrown nail; and (ii) a guide area having a slide groove that receives the lateral nail edge, the slide groove being capable of sliding in a longitudinal direction of a nail along the lateral nail edge, wherein the adhesive plaster structure has an approximately rod shape, the slide groove extends over a part of a length between the tip portion and the rear end portion of the adhesive plaster structure in the longitudinal direction of the adhesive plaster structure, and the flexible wound adhesion surface is guided to a position of the wound caused by the ingrown nail when the adhesive plaster structure is attached to the finger/toe. In particular, the inventor found that the flexible wound adhesion surface could be surely guided to the position of the wound by the unique structure formed by combining the wound adhesion area (i) having the flexible wound adhesion surface to be adhered to the wound caused by the ingrown nail and the guide area (ii) having the slide groove that receives the lateral nail edge, the slide groove being capable of sliding in the longitudinal direction of the nail along the lateral nail edge, regardless of degree of seriousness of the ingrown nail and the position of the wound caused by the ingrown nail in the longitudinal direction of the nail. In accordance with this knowledge, the present invention was completed.

Effects of the Invention

By using the adhesive plaster structure of the present invention, the flexible wound adhesion surface can be surely guided to the position of the wound regardless of degree of seriousness of the ingrown nail and the position of the wound caused by the ingrown nail in the longitudinal direction of the nail. Thus, the wound of the ingrown nail can be surely treated also near the root of the nail in addition to near the tip of the nail. In the conventional technology, the root of the nail could not be treated effectively and efficiently. Accordingly, the wound caused by the ingrown nail can be treated effectively and efficiently and pain of the wound caused by the ingrown nail can be relieved rapidly and drastically. Namely, the wound and pain caused by the ingrown nail can be surely and rapidly cured regardless of degree of seriousness of the ingrown nail and the position of the wound caused by the ingrown nail in the longitudinal direction of the nail. More specifically, if the adhesive plaster structure of the present invention is attached to the finger/toe, even severe pain of the wound is relieved almost instantly or within several seconds, and the pain disappears almost completely within several minutes or several tens of minutes. In addition, healing of the wound is advanced rapidly after the attachment of the adhesive plaster structure. Normally, healing of the wound is finished within very short period, i.e., about one week to ten days. In the treatment methods of the conventional technology, on the other hand, therapeutic effect to the wound caused by the ingrown nail cannot be expected immediately (i.e., pain of the wound does not disappear immediately). It is known in this industry that sufficient healing cannot be obtained in many cases of the serious wound even if the treatment is continued for long periods (about one or two months), and it takes about two or three months to obtain sufficient healing of the wound in many cases.

By using the adhesive plaster structure of the present invention, the flexible wound adhesion surface can be surely guided to the wound even when the wound to be treated is located at the root portion of the nail (invisible position covered by the posterior nail fold). This is impossible in the conventional technology. Furthermore, the adhesive plaster structure of the present invention has a function of assisting to correct the ingrown nail since an effect of correcting the ingrown nail is provided by an effect of pushing up the lateral nail edge (lateral edge of the nail).

EMBODIMENTS OF THE INVENTION

Figure 1A:
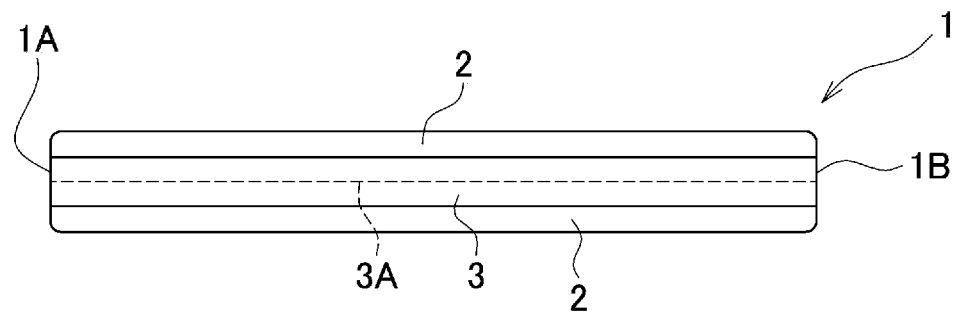
FIG. 1A is a schematic side view showing an example of the positional relation between the wound adhesion area and the guide area in the adhesive plaster structure of the present invention.

The present invention provides an adhesive plaster structure attached to a finger/toe along a lateral nail edge for treating wound caused by ingrown nail, the adhesive plaster structure comprising:

(i) a wound adhesion area having a flexible wound adhesion surface to be adhered to the wound caused by the ingrown nail; and (ii) a guide area having a slide groove that receives the lateral nail edge, the slide groove being capable of sliding in a longitudinal direction of a nail along the lateral nail edge, wherein the adhesive plaster structure has an approximately rod shape, when an end portion of the adhesive plaster structure located at a root side of the finger/toe is defined as a tip portion and an end portion of the adhesive plaster structure located at a root side of the finger/toe is defined as a rear end portion in a state that the adhesive plaster structure is attached to the finger/toe, the slide groove extends at least over a part of a length between the tip portion and the rear end portion of the adhesive plaster structure in the longitudinal direction of the adhesive plaster structure, and the flexible wound adhesion surface is guided to a position of the wound caused by the ingrown nail when the adhesive plaster structure is attached to the finger/toe.

Next, in order to assist the understanding of the present invention, a basic feature and various preferable embodiments of the present invention will be listed.

1. An adhesive plaster structure attached to a finger/toe along a lateral nail edge for treating wound caused by ingrown nail, the adhesive plaster structure comprising:

(i) a wound adhesion area having a flexible wound adhesion surface to be adhered to the wound caused by the ingrown nail; and (ii) a guide area having a slide groove that receives the lateral nail edge, the slide groove being capable of sliding in a longitudinal direction of a nail along the lateral nail edge, wherein the adhesive plaster structure has an approximately rod shape, when an end portion of the adhesive plaster structure located at a root side of the finger/toe is defined as a tip portion and an end portion of the adhesive plaster structure located at a tip side of the finger/toe is defined as a rear end portion in a state that the adhesive plaster structure is attached to the finger/toe, the slide groove extends at least over a part of a length between the tip portion and the rear end portion of the adhesive plaster structure in the longitudinal direction of the adhesive plaster structure, and the flexible wound adhesion surface is guided to a position of the wound caused by the ingrown nail when the adhesive plaster structure is attached to the finger/toe.

2. The adhesive plaster structure according to claim 1, wherein the wound adhesion area is formed by a soft body, and the guide area is formed by a hard body.

3. The adhesive plaster structure according to claim 2, wherein the soft body of the wound adhesion area is selected from the group consisting of a hydrogel body, a gauze, a woven fabric, a nonwoven fabric, an absorbent cotton body, a rubber body, a foamed polyurethane body, a sponge body, a fiber body, a resin body having high flexibility and a material body having a property of absorbing and storing body fluid by a porous structure and/or an uneven structure, and the hard body of the guide area is selected from the group consisting of a resin body having low flexibility, a metal body having low flexibility, a hard pulp body, a glass body, a stone material body and a ceramic body.

4. The adhesive plaster structure according to claim 1 or 2, wherein the wound adhesion area has a property of absorbing and storing body fluid.

5. The adhesive plaster structure according to any one of claims 1 to 4, further comprising: a handle to facilitate attaching the adhesive plaster structure to the finger/toe.

6. The adhesive plaster structure according to any one of claims 1 to 5, further comprising: an extension portion extending from the rear end portion of the adhesive plaster structure in a direction crossing the longitudinal direction of the adhesive plaster structure, wherein the extension portion has a groove to receive a tip edge portion of the nail when the adhesive plaster structure is attached to the finger/toe.

Hereafter, with reference to the attached drawings, the present invention will be explained in detail.

The adhesive plaster structure of the present invention is an adhesive plaster structure attached to a finger/toe along a lateral nail edge for treating wound caused by ingrown nail, the adhesive plaster structure comprising:

(i) a wound adhesion area having a flexible wound adhesion surface to be adhered to the wound caused by the ingrown nail; and (ii) a guide area having a slide groove that receives the lateral nail edge, the slide groove being capable of sliding in a longitudinal direction of a nail along the lateral nail edge.

In the present invention, the term "adhesive plaster structure" means a structure comprising: a structural area for exhibiting therapeutic effect having the flexible wound adhesion surface to be adhered to the wound of the finger/toe caused by the ingrown nail; and a structural area for guiding the flexible wound adhesion surface to the wound of the ingrown nail. In the present invention, the term "adhesive plaster structure" can be replaced with "medical-pad structure," for example. In the present invention, the term "wound" means a damage and/or lesion of body surface tissue and/or a surrounding area of the body surface tissue. In the present invention, the term "wound" can be accompanied with or without inflammation and/or exudation of body fluid. The adhesive plaster structure of the present invention can be also used for treating the damage (e.g., heat injury, burn injury, contused wound, abraded wound) and the lesion of the body surface tissue and/or the surrounding area of the body surface tissue caused by other reasons without limited to the wound caused by the ingrown nail.

The adhesive plaster structure of the present invention can be provided with or without an adhesive surface on any part (body portion and/or overhang portion of the body portion) of the adhesive plaster structure to hold the adhesive plaster structure on the nail of the finger/toe of the patient. When the adhesive plaster structure of the present invention is attached to the finger/toe along the lateral nail edge, the adhesive plaster structure is arranged between the lateral edge portion of the nail (lateral nail edge) and the wound site neighboring the lateral edge portion of the nail. Thus, the slide groove of the guide area (ii) receives the lateral edge portion of the nail, and the flexible wound adhesion surface of the wound adhesion area (i) is adhered to the wound site stably. Because of this, even if an adhesive surface to hold the adhesive plaster structure on the nail of the finger/toe of the patient is provided or not provided, the adhesive plaster structure of the present invention is held to the finger/toe of the patient stably.

The adhesive plaster structure of the present invention has a function of guiding the flexible wound adhesion surface of the wound adhesion area (i) to the wound site surely, for example, by the slide groove of the guide area (ii) that receives the lateral edge portion of the nail (lateral nail edge) and is slid in the longitudinal direction of the nail (i.e., direction of extending the lateral nail edge) along the lateral nail edge and/or by the slide groove of the guide area (ii) that receives the lateral edge portion of the nail (lateral nail edge) and slid in the direction crossing the longitudinal direction of the nail. (From the viewpoint of the function, the slide groove of the guide area (ii) can be also referred to as "guide groove.")

In the adhesive plaster structure of the present invention, the flexible wound adhesion surface of the wound adhesion area (i) is surely guided to the wound site caused by the ingrown nail by the function of the slide groove of the guide area (ii), and the flexible surface is adhered to the wound site and held on the wound site stably. Thus, healing promoting effect and healing effect to the wound is obtained. As explained above, because of the linkage between the wound adhesion area (i) and the guide area (ii), excellent effect is obtained in the present invention.

The adhesive plaster structure of the present invention has an approximately rod shape, the slide groove extends at least over a part of a length between the tip portion and the rear end portion of the adhesive plaster structure in the longitudinal direction of the adhesive plaster structure.

Here, the end portion of the adhesive plaster structure located at the root side of the finger/toe is defined as the tip portion and the end portion of the adhesive plaster structure located at the tip side of the finger/toe is defined as the rear end portion in a state that the adhesive plaster structure is attached to the finger/toe.

In various basic embodiments of the adhesive plaster structure of the present invention, the body portion of the adhesive plaster structure of the present invention has an approximately rod shape (i.e., rod shape, columnar shape, conical shape, square columnar shape, pyramid shape and similar shapes of them) as an entire shape. However, since the adhesive plaster structure of the present invention is a device for treating the wound of the ingrown nail, performance and safety should be considered with the highest priority as the treatment tool. Accordingly, there is no need to be particular about a specific shape as the shape of the embodiment of the adhesive plaster structure of the present invention. Preferably, the most appropriate shape should be selected in viewpoints of performance, safety and economic efficiency corresponding to the individual case to apply the adhesive plaster structure.

In the adhesive plaster structure of the present invention, the positional relation between the wound adhesion area (i) and the guide area (ii) can be selected from various options according to the position and condition of the wound to be treated and requirements of the treatment.

FIGS. 1A-1L show schematic side views showing typical examples of the positional relation between the wound adhesion area (i) and the guide area (ii) in the adhesive plaster structure of the present invention. In FIGS. 1A-1L, the reference numeral 1 indicates the adhesive plaster structure, the reference numeral 1A indicates a tip portion of the adhesive plaster structure, the reference numeral 1B indicates a rear end portion of the adhesive plaster structure, the reference numeral 2 indicates the wound adhesion area (i), the reference numeral 3 indicates the guide area (ii), and the reference numeral 3A indicates the slide groove (shown as broken line) of the guide area (ii).

In the embodiment shown in FIG. 1A, a wound adhesion area 2 extends over an entire length between a tip portion 1A and a rear end portion 1B of an adhesive plaster structure 1, and a slide groove 3A of a guide area 3 continuously extends in the longitudinal direction of the adhesive plaster structure 1 over an entire length between the tip portion 1A and the rear end portion 1B of the adhesive plaster structure 1.

Figure 1B:
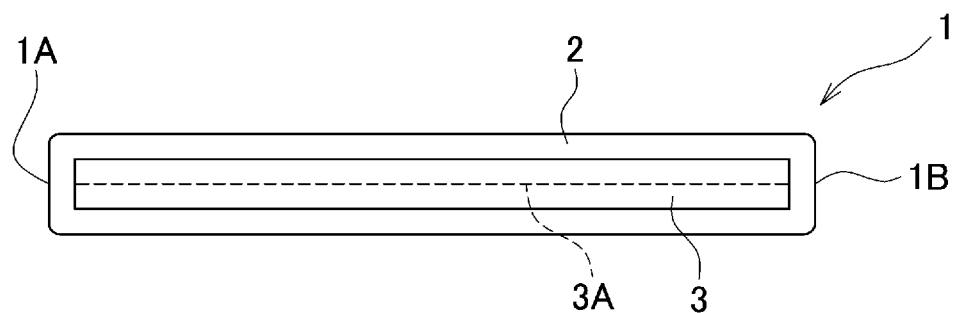
FIG. 1B is a schematic side view showing another example of the positional relation between the wound adhesion area and the guide area in the adhesive plaster structure of the present invention.

In the embodiment shown in FIG. 1B, the wound adhesion area 2 extends over an entire length between the tip portion 1A and the rear end portion 1B of the adhesive plaster structure 1, and the slide groove 3A of the guide area 3 continuously extends in the longitudinal direction of the adhesive plaster structure 1 over an almost entire length between the tip portion 1A and the rear end portion 1B of the adhesive plaster structure 1 (except for the end portion of the tip portion 1A side and the end portion of the rear end portion 1B side).

Figure 1C:
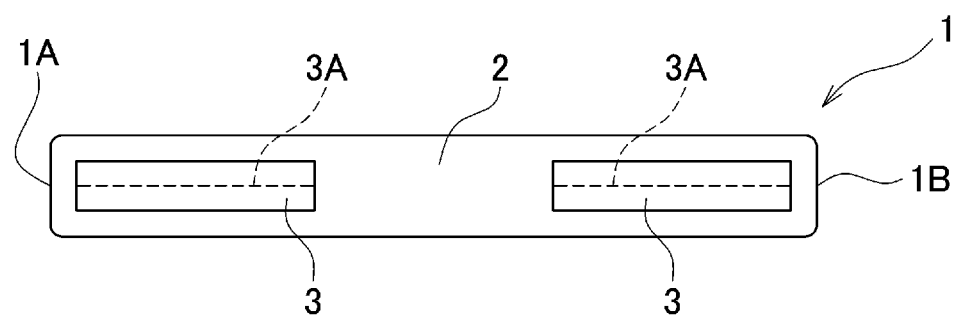
FIG. 1C is a schematic side view showing another example of the positional relation between the wound adhesion area and the guide area in the adhesive plaster structure of the present invention.

In the embodiment shown in FIG. 1C, the wound adhesion area 2 extends over an entire length between the tip portion 1A and the rear end portion 1B of the adhesive plaster structure 1, and the slide groove 3A of the guide area 3 extends in the longitudinal direction of the adhesive plaster structure 1 at a portion except for the intermediate region between the tip portion 1A and the rear end portion 1B of the adhesive plaster structure 1 (at the region near the tip portion 1A and the rear end portion 1B side). As shown in FIG. 1C, the guide area 3 can be intermittently formed (i.e., the guide area 3 can be divided into a plurality of sections).

Figure 1D:
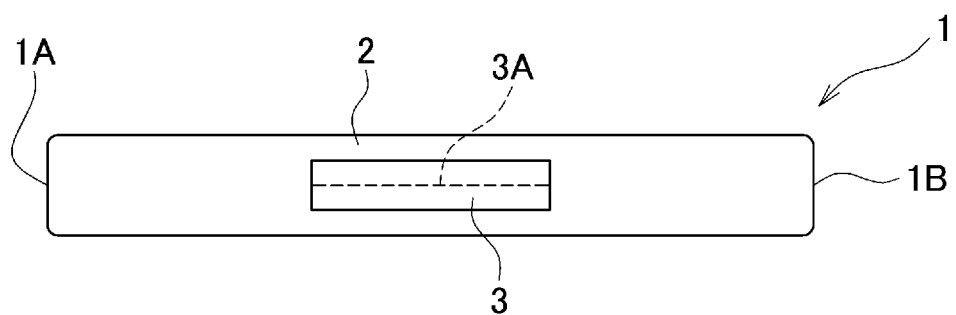
FIG. 1D is a schematic side view showing another example of the positional relation between the wound adhesion area and the guide area in the adhesive plaster structure of the present invention.

In the embodiment shown in FIG. 1D, the wound adhesion area 2 extends over an entire length between the tip portion 1A and the rear end portion 1B of the adhesive plaster structure 1, and the slide groove 3A of the guide area 3 extends in the longitudinal direction of the adhesive plaster structure 1 only at the intermediate region between the tip portion 1A and the rear end portion 1B of the adhesive plaster structure 1.

Figure 1E:
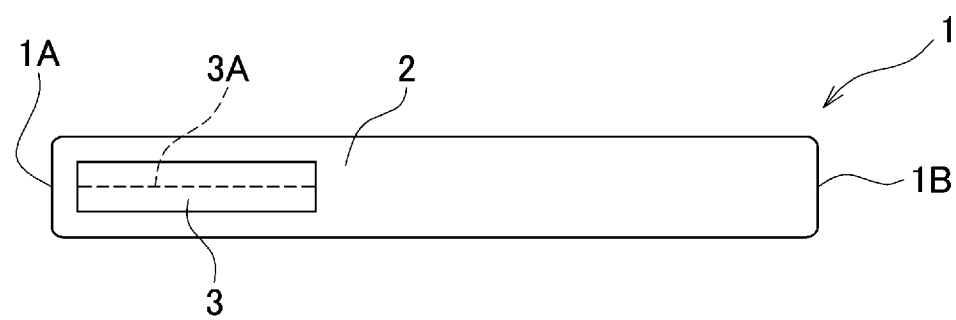
FIG. 1E is a schematic side view showing another example of the positional relation between the wound adhesion area and the guide area in the adhesive plaster structure of the present invention.

In the embodiment shown in FIG. 1E, the wound adhesion area 2 extends over an entire length between the tip portion 1A and the rear end portion 1B of the adhesive plaster structure 1, and the slide groove 3A of the guide area 3 extends in the longitudinal direction of the adhesive plaster structure 1 only at the region of the tip portion 1A side between the tip portion 1A and the rear end portion 1B of the adhesive plaster structure 1.

Figure 1F:
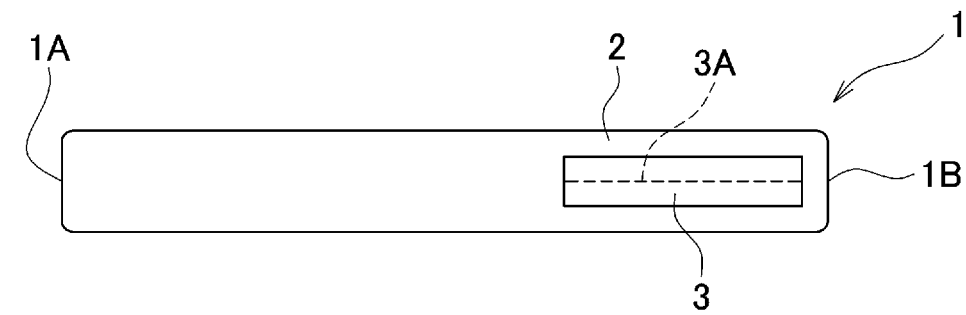
FIG. 1F is a schematic side view showing another example of the positional relation between the wound adhesion area and the guide area in the adhesive plaster structure of the present invention.

In the embodiment shown in FIG. 1F, the wound adhesion area 2 extends over an entire length between the tip portion 1A and the rear end portion 1B of the adhesive plaster structure 1, and the slide groove 3A of the guide area 3 extends in the longitudinal direction of the adhesive plaster structure 1 only at the region of the rear end portion 1B side between the tip portion 1A and the rear end portion 1B of the adhesive plaster structure 1.

Figure 1G:
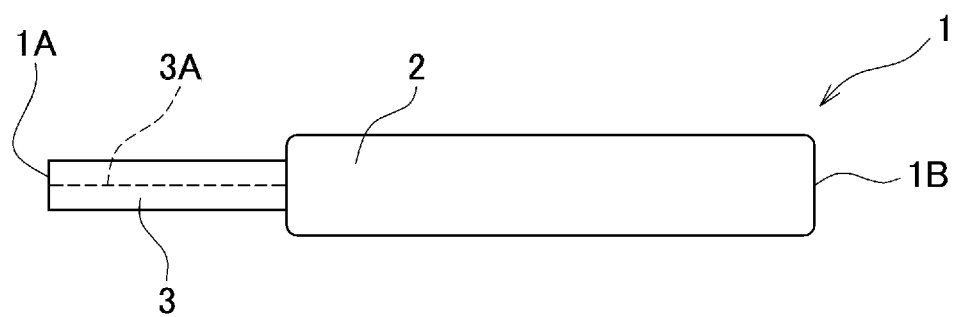
FIG. 1G is a schematic side view showing another example of the positional relation between the wound adhesion area and the guide area in the adhesive plaster structure of the present invention.

In the embodiment shown in FIG. 1G, the region of the tip portion 1A side of the adhesive plaster structure 1 is formed only by the guide area 3, the region of the rear end portion 1B side of the adhesive plaster structure 1 is formed only by the wound adhesion area 2, and the slide groove 3A of the guide area 3 extends in the longitudinal direction of the adhesive plaster structure 1 only at the region of the tip portion 1A side between the tip portion 1A and the rear end portion 1B of the adhesive plaster structure 1.

Figure 1H:
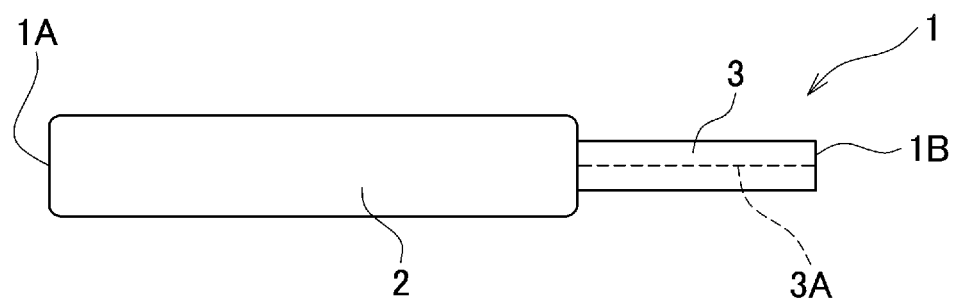
FIG. 1H is a schematic side view showing another example of the positional relation between the wound adhesion area and the guide area in the adhesive plaster structure of the present invention.

In the embodiment shown in FIG. 1H, the region of the rear end portion 1B side of the adhesive plaster structure 1 is formed only by the guide area 3, the region of the tip portion 1A side of the adhesive plaster structure 1 is formed only by the wound adhesion area 2, and the slide groove 3A of the guide area 3 extends in the longitudinal direction of the adhesive plaster structure 1 only at the region of the rear end portion 1B side between the tip portion 1A and the rear end portion 1B of the adhesive plaster structure 1.

Figure 1I:
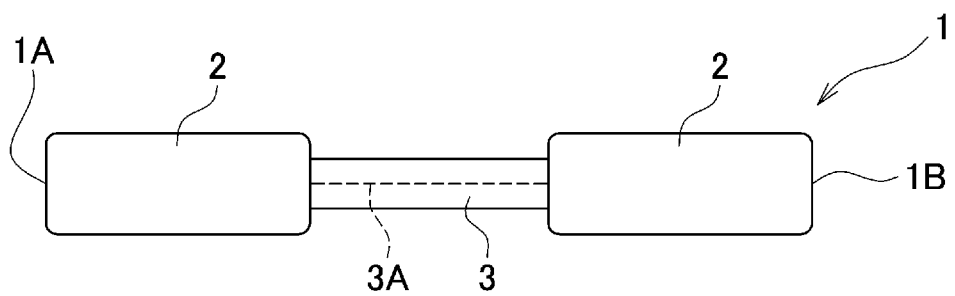
FIG. 1I is a schematic side view showing another example of the positional relation between the wound adhesion area and the guide area in the adhesive plaster structure of the present invention.

In the embodiment shown in FIG. 1I, the intermediate region between the tip portion 1A and the rear end portion 1B of the adhesive plaster structure 1 is formed only by the guide area 3, the region near the tip portion 1A and the region near the rear end portion 1B of the adhesive plaster structure 1 are formed only by the wound adhesion area 2, and the slide groove 3A of the guide area 3 extends in the longitudinal direction of the adhesive plaster structure 1 only at the intermediate region.

Figure 1J:
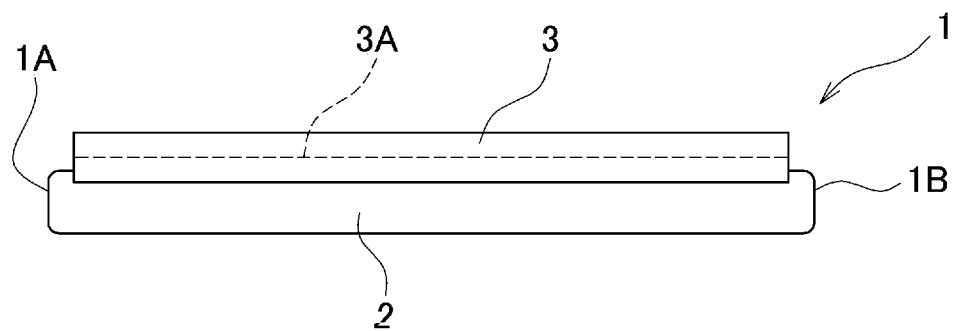
FIG. 1J is a schematic side view showing another example of the positional relation between the wound adhesion area and the guide area in the adhesive plaster structure of the present invention.

In the embodiment shown in FIG. 1J, the wound adhesion area 2 extends over an entire length between the tip portion 1A and the rear end portion 1B of the adhesive plaster structure 1, and the slide groove 3A of the guide area 3 continuously extends in the longitudinal direction of the adhesive plaster structure 1 over an almost entire length between the tip portion 1A and the rear end portion 1B of the adhesive plaster structure 1 (except for the end portion of the tip portion 1A side and the end portion of the rear end portion 1B side).

Figure 1K:
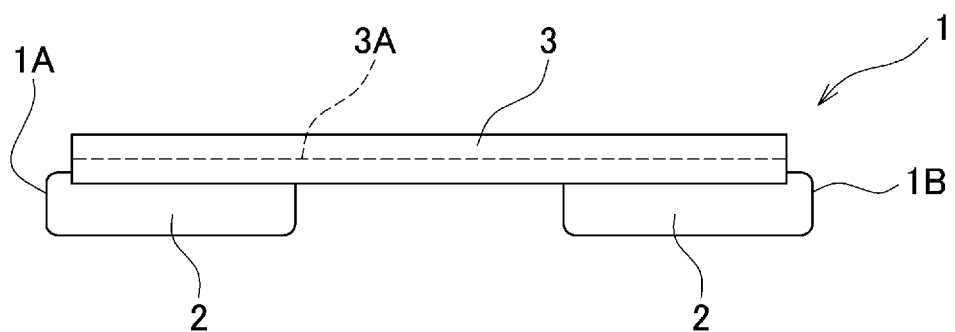
FIG. 1K is a schematic side view showing another example of the positional relation between the wound adhesion area and the guide area in the adhesive plaster structure of the present invention.

In the embodiment shown in FIG. 1K, the wound adhesion area 2 extends at a portion except for the intermediate region between the tip portion 1A and the rear end portion 1B of the adhesive plaster structure 1 (at the region near the tip portion 1A and the rear end portion 1B side), and the slide groove 3A of the guide area 3 continuously extends in the longitudinal direction of the adhesive plaster structure 1 over an almost entire length between the tip portion 1A and the rear end portion 1B of the adhesive plaster structure 1 (except for the end portion of the tip portion 1A side and the end portion of the rear end portion 1B side).

Figure 1L:
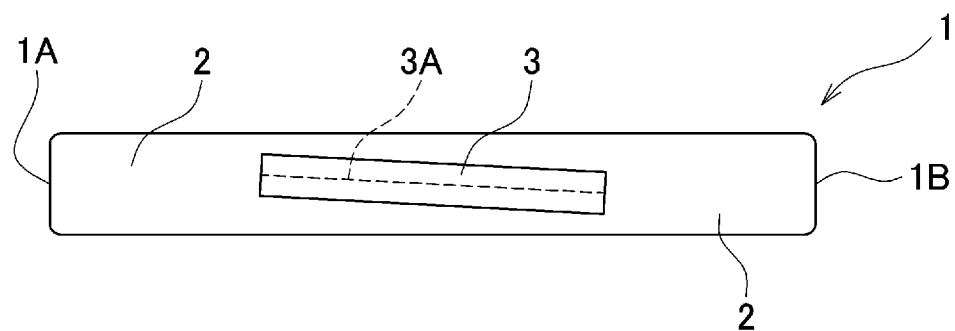
FIG. 1L is a schematic side view showing another example of the positional relation between the wound adhesion area and the guide area in the adhesive plaster structure of the present invention.

In the embodiment shown in FIG. 1L, the wound adhesion area 2 extends over an entire length between the tip portion 1A and the rear end portion 1B of the adhesive plaster structure 1, the slide groove 3A of the guide area 3 extends in the longitudinal direction of the adhesive plaster structure 1 only at the intermediate region so that the slide groove 3A is slightly inclined with respect to the longitudinal direction.

As exemplified in FIGS. 1A-1L, in the adhesive plaster structure 1 of the present invention, the positional relation between the wound adhesion area 2 and the guide area 3 can be designed with high flexibility to comply with various conditions such as the position and condition of the wound to be treated and requirements of the treatment. Thus, the wound caused by the ingrown nail can be treated effectively, efficiently and immediately. In the adhesive plaster structure 1 of the present invention, the positional relation between the wound adhesion area 2 and the guide area 3 is not limited to the examples shown in FIGS. 1A-1L. As long as the purpose of the present invention is attained, other various positional relations can be used.

As long as the wound adhesion area 2 and the guide area 3 can perform respective functions after the adhesive plaster structure of the present invention is attached to the finger/toe, the positional relation between the wound adhesion area 2 and the guide area 3 and the shapes of them are not particularly limited before and after the adhesive plaster structure of the present invention is attached to the finger/toe. For example, the positional relation between the wound adhesion area 2 and the guide area 3 and the shapes of them can be changed or kept unchanged when the adhesive plaster structure of the present invention is attached to the finger/toe.

When the adhesive plaster structure of the present invention is attached to the finger/toe, because of the function of the slide groove 3A of the guide area 3, the flexible wound adhesion surface is guided to the position of the wound caused by the ingrown nail.

As long as the excellent effect of the present invention can be obtained, the method of attaching the adhesive plaster structure of the present invention to the finger/toe is not particularly limited. The method of attaching the adhesive plaster structure to the finger/toe can be arbitrarily selected according to the individual case such as the condition of the ingrown nail, the condition of the wound caused by the ingrown nail, and the shape of the finger/toe and the nail of the patient. In one embodiment of attaching the adhesive plaster structure of the present invention to the finger/toe, the tip portion 1A of the adhesive plaster structure 1 is inserted from the tip side of the finger/toe along the lateral nail edge (lateral edge portion of the nail) and the slide groove 3A is slid to the root side of the nail along the lateral nail edge. Thus, the flexible wound adhesion surface of the wound adhesion area 2 can be guided to the position of the wound caused by the ingrown nail. In another embodiment of attaching the adhesive plaster structure of the present invention to the finger/toe, the slide groove 3A extending the longitudinal direction of the adhesive plaster structure of the present invention is inserted from the lateral edge portion side of the finger/toe to fit to the lateral nail edge (lateral edge portion of the nail) and, if desired, the slide groove 3A is slid to the root side or the tip side of the nail along the lateral nail edge. (When the slide groove 3A is fit to the lateral nail edge, the slide groove 3A is slightly slid in the direction crossing the slide groove 3A and the longitudinal direction of the nail.) Thus, the flexible wound adhesion surface of the wound adhesion area 2 can be guided to the position of the wound caused by the ingrown nail. The following three kinds of motions can be listed as examples of main motions for attaching the adhesive plaster structure of the present invention to the finger/toe: (1) motion of sliding the slide groove 3A to the root side or the tip side of the nail along the lateral nail edge; (2) motion of sliding the slide groove 3A in the direction crossing the slide groove 3A and the longitudinal direction of the nail; and (3) motion of moving the slide groove 3A in the thickness direction of the nail. These motions can be used in combination freely if required or desired. When attaching, or removing the adhesive plaster structure of the present invention to/from the finger/toe or after attaching it, the adhesive plaster structure can be moved three-dimensionally in any directions of the finger/toe and/or the nail if required or desired.

When the adhesive plaster structure of the present invention is attached to the finger/toe along the lateral nail edge, the adhesive plaster structure is arranged between the lateral edge portion of the nail (lateral nail edge) and the wound site neighboring the lateral edge portion of the nail, the slide groove 3A of the guide area 3 receives the lateral edge portion of the nail, and the flexible wound adhesion surface of the wound adhesion area 2 is attached to the wound site and held stably.

Figure 2:
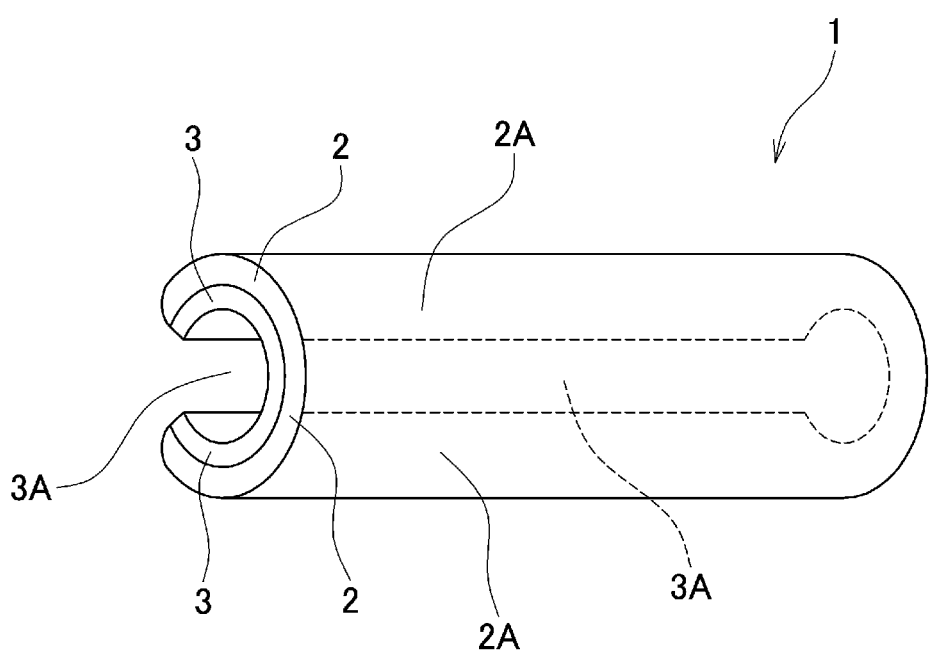
FIG. 2 is a schematic perspective view showing an example of the adhesive plaster structure of the present invention.

FIG. 2 is a schematic perspective view showing an example of the adhesive plaster structure of the present invention. The adhesive plaster structure 1 shown in FIG. 2 includes the wound adhesion area 2 and the guide area 3. The wound adhesion area 2 includes a flexible wound adhesion surface 2A to be adhered to the wound caused by the ingrown nail. The guide area 3 includes the slide groove 3A that receives the lateral nail edge (lateral edge portion of the nail) and is capable of sliding in the longitudinal direction of the nail along the lateral nail edge. The adhesive plaster structure 1 shown in FIG. 2 has an approximately rod shape as an entire shape and a C-shape as a cross-sectional shape. The slide groove 3A (internal space of the C-shape) extends in the longitudinal direction of the adhesive plaster structure 1 over an entire length between the tip portion and the rear end portion of the adhesive plaster structure 1.

In the present invention, in a state that the adhesive plaster structure 1 is attached to the finger/toe, an end portion of the adhesive plaster structure 1 located at a root side of the finger/toe is defined as a tip portion and an end portion of the adhesive plaster structure 1 located at a tip side of the finger/toe is defined as a rear end portion. Accordingly, for example, when the end portion of the adhesive plaster structure 1 located at the right side in FIG. 2 is inserted from the tip side of the finger/toe along the lateral nail edge (lateral edge portion of the nail) and slid to the root side of the nail to attach the adhesive plaster structure 1, this end portion is regarded as the tip portion 1A of the adhesive plaster structure 1 and the other end portion is regarded as the rear end portion 1B. Needless to say, when the end portion of the adhesive plaster structure 1 located at the left side in FIG. 2 is inserted from the tip side of the finger/toe along the lateral nail edge (lateral edge portion of the nail) and slid to the root side of the nail to attach the adhesive plaster structure 1, this end portion is regarded as the tip portion 1A of the adhesive plaster structure 1 and the other end portion is regarded as the rear end portion 1B. According to the situation, one of both ends of the adhesive plaster structure 1 can be freely determined to serve as the tip portion 1A or the rear end portion 1B.

Figure 3A:
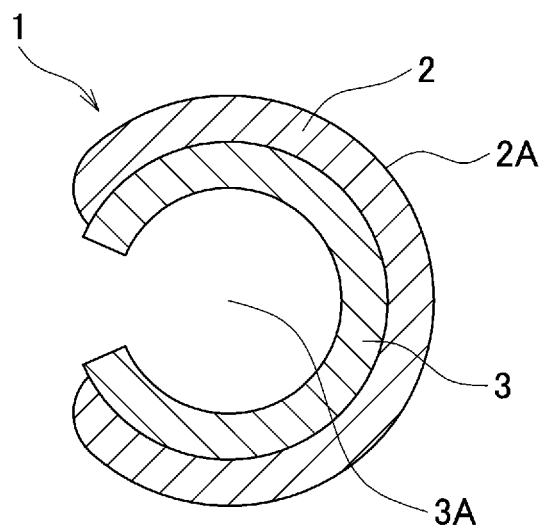
FIG. 3A is a schematic cross-sectional view in the direction crossing the longitudinal direction of the adhesive plaster structure showing an example of the positional relation between the wound adhesion area and the guide area of the adhesive plaster structure of the present invention.

The adhesive plaster structure of the present invention can have various cross-sectional shapes. FIGS. 3A-3R show schematic cross-sectional views showing typical examples of the positional relation between the wound adhesion area 2 and the guide area 3 of the adhesive plaster structure when both the wound adhesion area 2 and the guide area 3 are shown in the cross-sectional view in the direction crossing the longitudinal direction of the adhesive plaster structure 1 of the present invention.

In the embodiment of FIG. 3A, both the wound adhesion area 2 and the guide area 3 have a C-shape in cross section and are closely contact with each other.

Figure 3B:
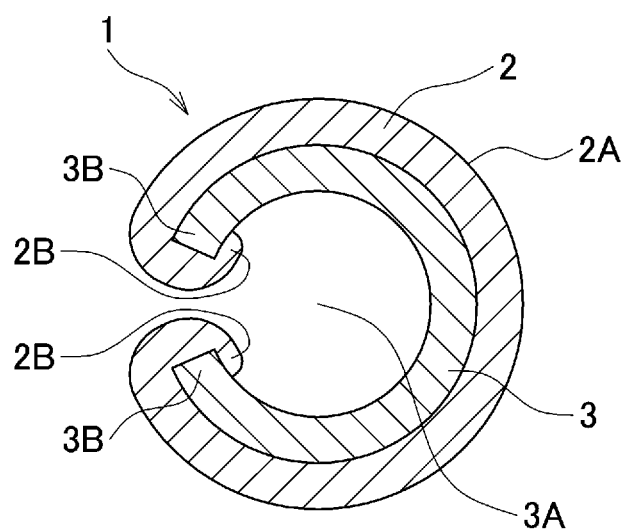
FIG. 3B is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3B, the guide area 3 has a C-shape in cross section, the wound adhesion area 2 has an approximately C-shape in cross section, the wound adhesion area 2 includes two edge portions 2B to cover two edge portions 3B extending in a longitudinal direction of the guide area 3, and the wound adhesion area 2 and the guide area 3 are closely contact with each other.

Figure 3C:
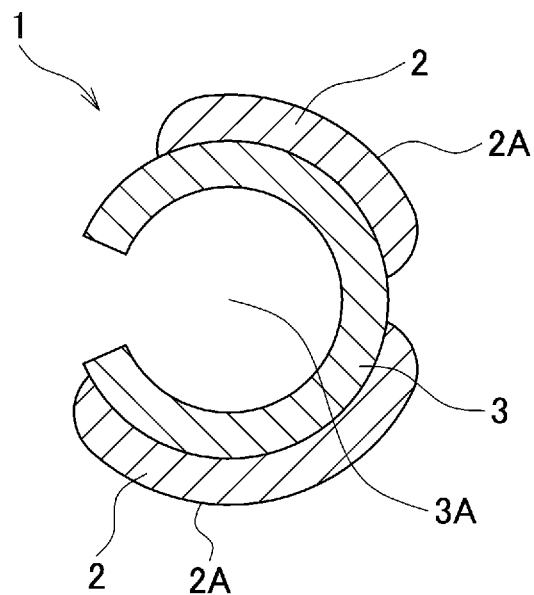
FIG. 3C is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3C, the guide area 3 has a C-shape in cross section, the wound adhesion area 2 is formed from two approximately arc-shapes in cross section, and the wound adhesion area 2 and the guide area 3 are closely contact with each other.

Figure 3D:
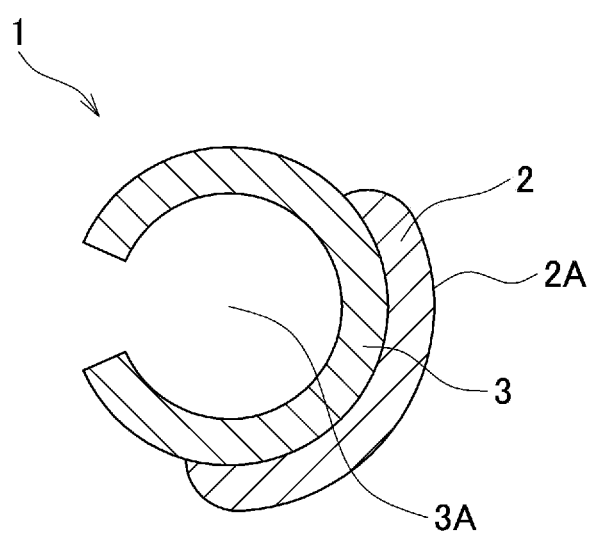
FIG. 3D is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3D, the guide area 3 has a C-shape in cross section, the wound adhesion area 2 has an approximately arc-shape in cross section, and the wound adhesion area 2 and the guide area 3 are closely contact with each other.

Figure 3E:
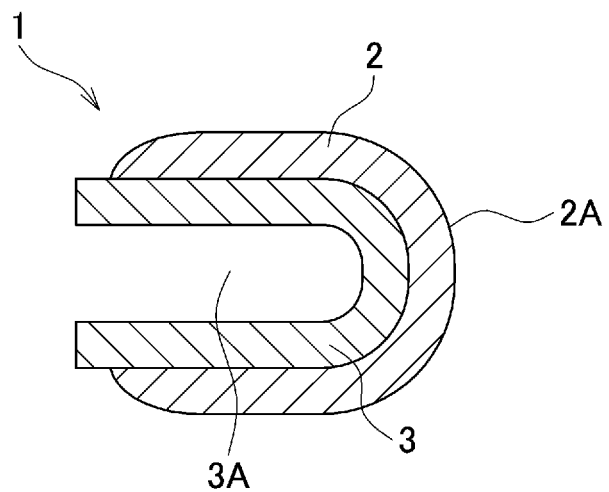
FIG. 3E is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3E, both the wound adhesion area 2 and the guide area 3 have a U-shape in cross section and are closely contact with each other.

Figure 3F:
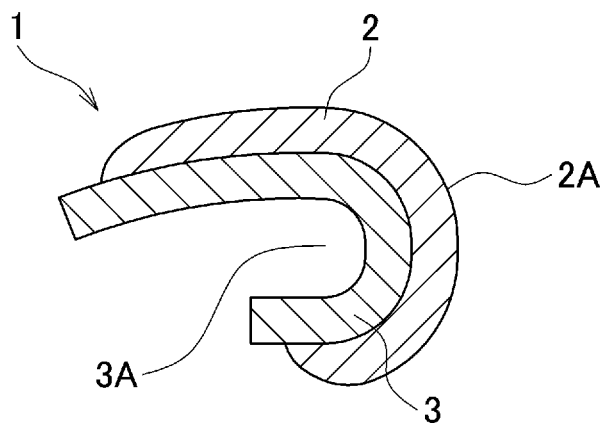
FIG. 3F is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3F, both the wound adhesion area 2 and the guide area 3 have a J-shape in cross section and are closely contact with each other.

Figure 3G:
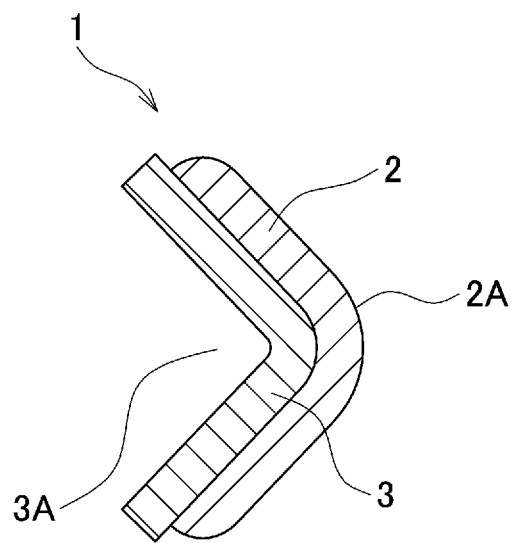
FIG. 3G is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3G, both the wound adhesion area 2 and the guide area 3 have an L-shape in cross section and are closely contact with each other.

Figure 3H:
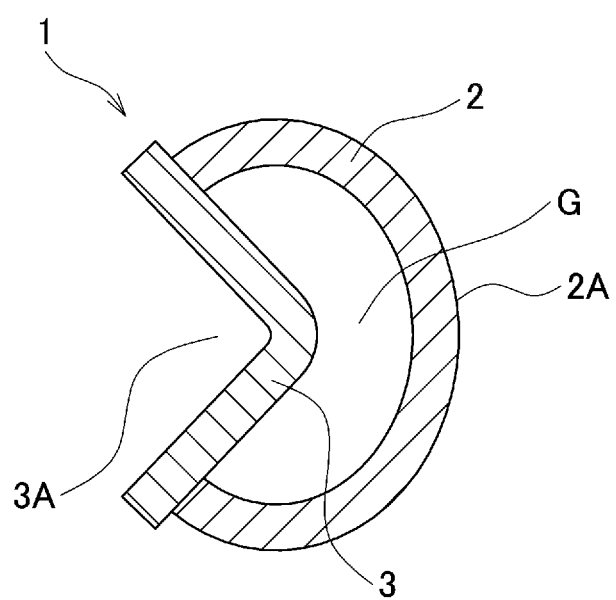
FIG. 3H is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3H, the guide area 3 has an L-shape in cross section, the wound adhesion area 2 has a C-shape in cross section, and the wound adhesion area 2 and the guide area 3 are in contact with each other at upper and lower two points having a gap G between them.

Figure 3I:
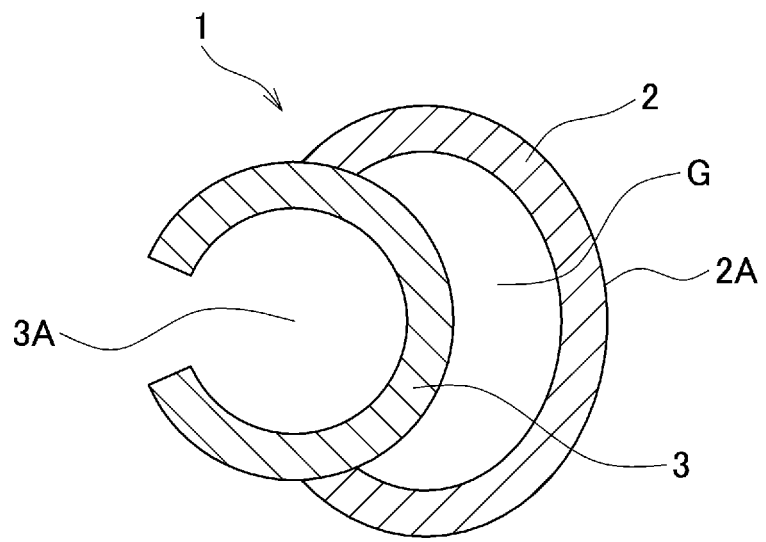
FIG. 3I is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3I, the guide area 3 has a C-shape in cross section, the wound adhesion area 2 has a C-shape in cross section, and the wound adhesion area 2 and the guide area 3 are in contact with each other at upper and lower two points having a gap G between them.

Figure 3J:
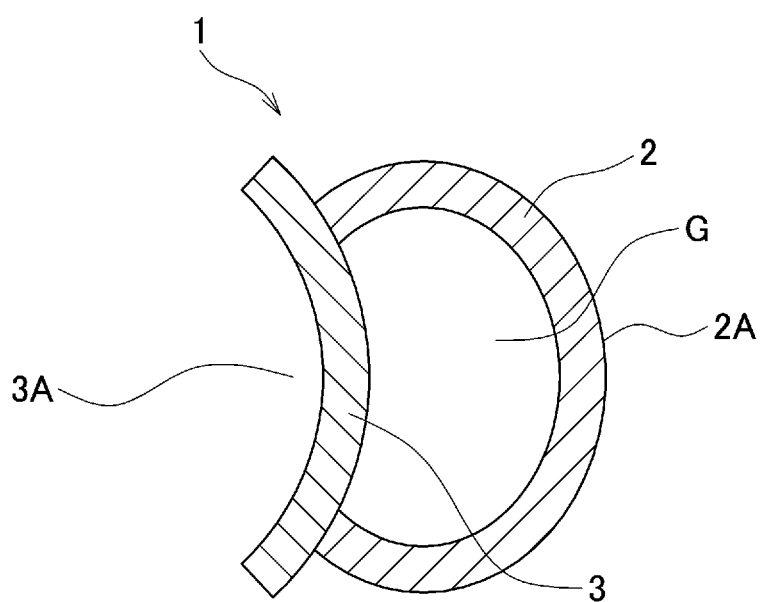
FIG. 3J is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3J, the guide area 3 has an approximately arc-shape in cross section, the wound adhesion area 2 has a C-shape in cross section, and the wound adhesion area 2 and the guide area 3 are in contact with each other at upper and lower two points having a gap G between them.

Figure 3K:
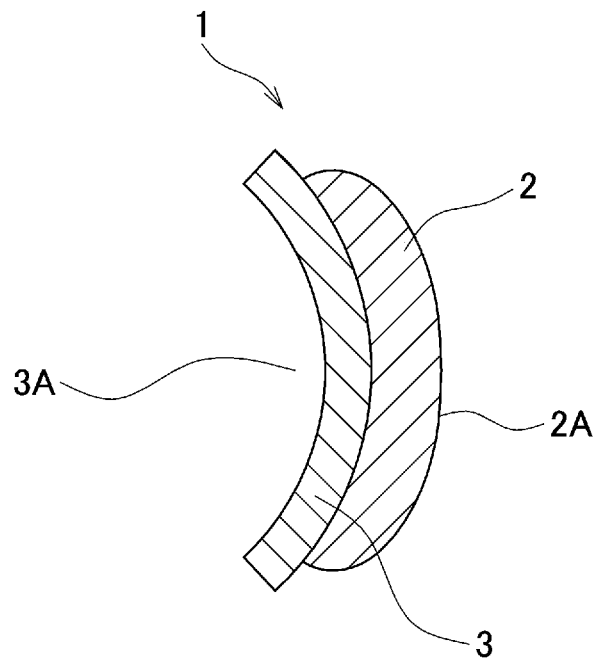
FIG. 3K is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3K, both the wound adhesion area 2 and the guide area 3 have an approximately arc-shape in cross section and are closely contact with each other.

Figure 3L:
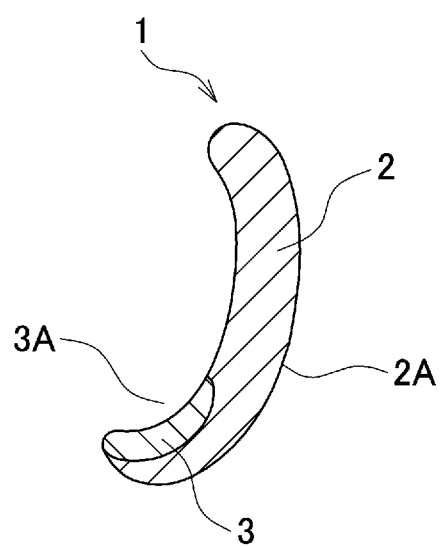
FIG. 3L is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3L, both the wound adhesion area 2 and the guide area 3 have an approximately arc-shape in cross section and are closely contact with each other.

Figure 3M:
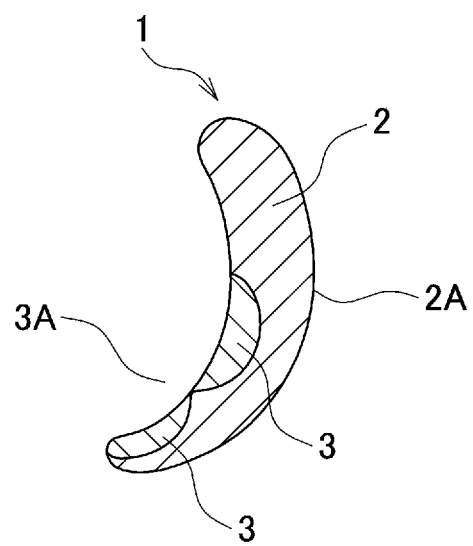
FIG. 3M is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3M, the guide area 3 is formed from two approximately arc-shapes in cross section, the wound adhesion area 2 has an approximately arc-shape in cross section, and the wound adhesion area 2 and the guide area 3 are closely contact with each other.

Figure 3N:
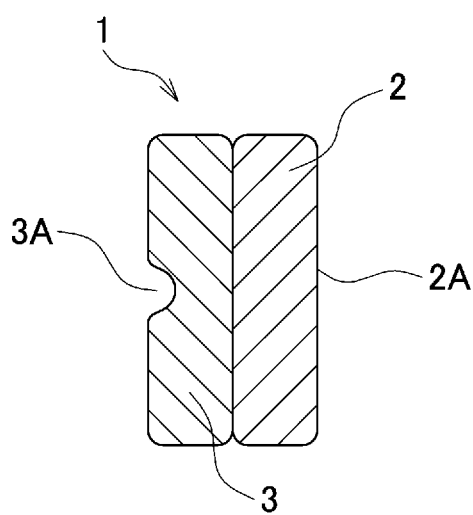
FIG. 3N is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3N, both the wound adhesion area 2 and the guide area 3 have a rectangular-shape in cross section and are closely contact with each other.

Figure 3O:
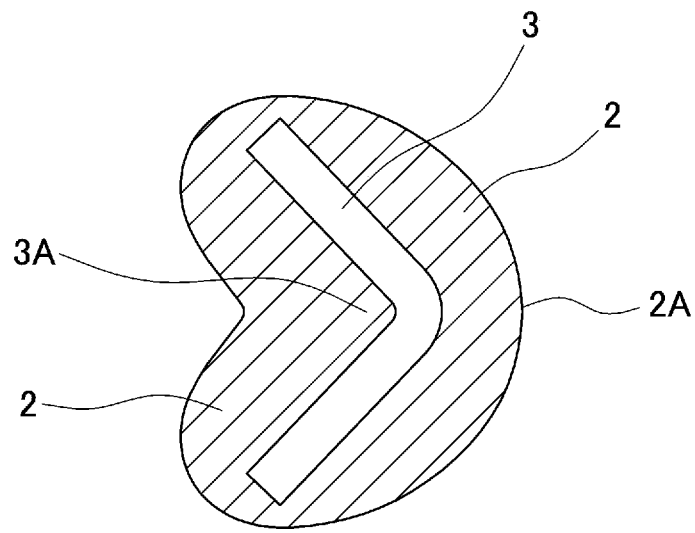
FIG. 3O is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3O, the guide area 3 has an L-shape in cross section, the wound adhesion area 2 has a heart-shape in cross section, and the wound adhesion area 2 is closely contact with the guide area 3 and covers the guide area 3 entirely.

Figure 3P:
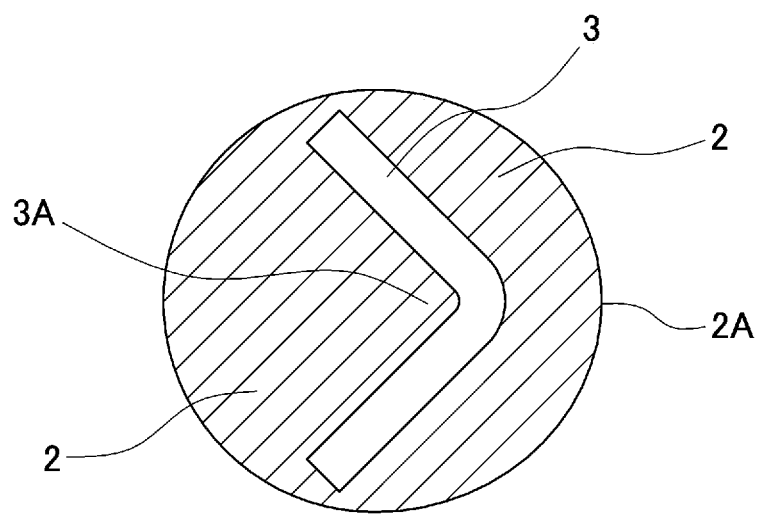
FIG. 3P is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3P, the guide area 3 has an L-shape in cross section, the wound adhesion area 2 has a circular-shape in cross section, and the wound adhesion area 2 is closely contact with the guide area 3 and covers the guide area 3 entirely.

Figure 3Q:
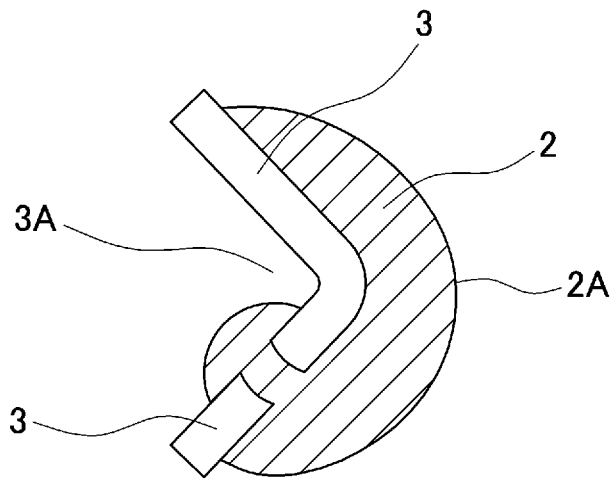
FIG. 3Q is a schematic cross-sectional view in the direction crossing the longitudinal direction of the adhesive plaster structure showing another example of the positional relation between the wound adhesion area and the guide area of the adhesive plaster structure of the present invention.
Figure 3R:
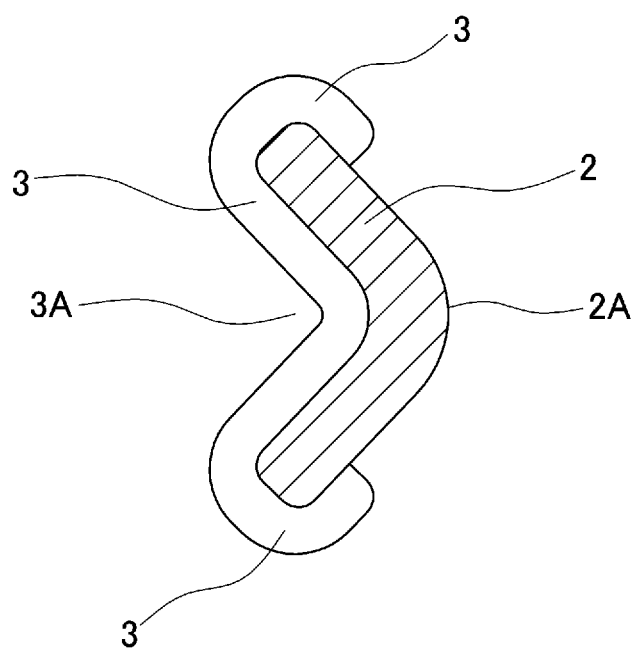
FIG. 3R is a schematic cross-sectional view in the direction crossing the longitudinal direction of the adhesive plaster structure showing another example of the positional relation between the wound adhesion area and the guide area of the adhesive plaster structure of the present invention.

In the embodiment of FIG. 3Q, the guide area 3 has an approximately L-shape in cross section, the wound adhesion area 2 and the guide area 3 are closely contact with each other, and a part of the wound adhesion area 2 penetrates an opening portion of the guide area 3 and protrudes from the other side (side of the slide groove 3A).

In the embodiment of FIG. 3R, the guide area 3 has a sigma (Σ)-shape in cross section, the wound adhesion area 2 has an L-shape in cross section, and the wound adhesion area 2 and the guide area 3 are closely contact with each other.

The gap G can be airtightly or liquid tightly sealed or kept unsealed. In addition, the gap G can contain fluid (e.g. water, body fluid, liquid medicine, air, inert gas), jelly-like substance, powder and granular material and/or one kind or two or more kinds of soft bodies (mentioned later) available for the wound adhesion area 2.

The thickness of the wound adhesion area 2 is not particularly limited. However, the thickness is generally within the range of 0.01 to 10.0 mm, preferably the range of 0.05 to 5.0 mm, and more preferably the range of 0.1 to 3.0 mm. The thickness of the guide area 3 is not particularly limited. However, the thickness is generally within the range of 0.01 to 8.0 mm, preferably the range of 0.05 to 4.0 mm, and more preferably the range of 0.1 to 2.0 mm. The thickness of the gap G is not particularly limited. However, the thickness is generally within the range of 0.1 to 5.0 mm, preferably the range of 0.2 to 3.0 mm, and more preferably the range of 0.3 to 2.0 mm.

In the adhesive plaster structure of the present invention, the cross-sectional shape in the direction crossing the longitudinal direction of the adhesive plaster structure can be constant over the longitudinal direction or different. When the cross-sectional shape is different in the longitudinal direction of the adhesive plaster structure, two or more kinds of various cross-sectional shapes shown in FIGS. 3A-3R can be combined, for example. The cross-sectional shape of the adhesive plaster structure of the present invention in the direction crossing the longitudinal direction is not limited to the shapes shown in FIGS. 3A-3R. As long as the purpose of the present invention is attained, various cross-sectional shapes can be further used.

As long as the wound adhesion area 2 and the guide area 3 can perform respective functions after the adhesive plaster structure of the present invention is attached to the finger/toe, the positional relation between the wound adhesion area 2 and the guide area 3 and the shapes of them in the cross-section crossing the longitudinal direction of the adhesive plaster structure of the present invention are not particularly limited before and after the adhesive plaster structure of the present invention is attached to the finger/toe. The positional relation between the wound adhesion area 2 and the guide area 3 and the shapes of them can be changed or kept unchanged when the adhesive plaster structure of the present invention is attached to the finger/toe.

The adhesive plaster structure of the present invention can have various entire shapes. FIG. 4A-4H show schematic side views showing typical examples of an entire shape of the adhesive plaster structure of the present invention.

Figure 4A:
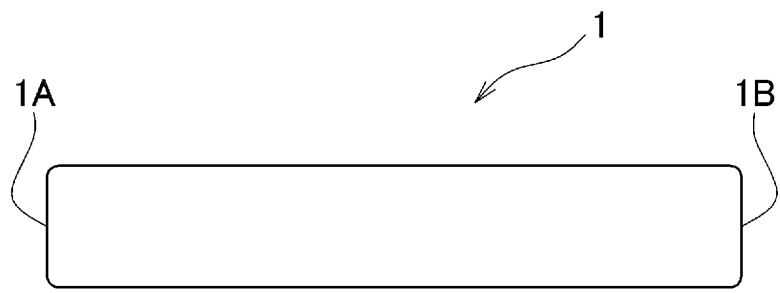
FIG. 4A is a schematic side view showing an example of an entire shape of the adhesive plaster structure of the present invention.

In the embodiment of FIG. 4A, the shape of the adhesive plaster structure 1 is an approximately rod-shape having a constant diameter in the longitudinal direction.

Figure 4B:
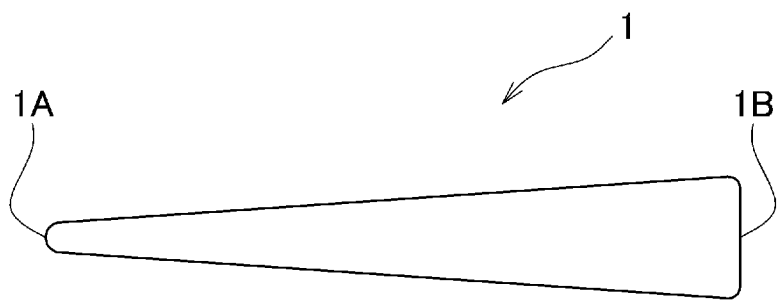
FIG. 4B is a schematic side view showing another example of an entire shape of the adhesive plaster structure of the present invention.

In the embodiment of FIG. 4B, the shape of the adhesive plaster structure 1 is an approximately rod-shape having a diameter reducing from the rear end portion 1B to the tip portion 1A in the longitudinal direction. (Namely, the adhesive plaster structure 1 has a tapered shape from the rear end portion 1B to the tip portion 1A.)

Figure 4C:
FIG. 4C is a schematic side view showing another example of an entire shape of the adhesive plaster structure of the present invention.

In the embodiment of FIG. 4C, the shape of the adhesive plaster structure 1 is an approximately rod-shape where a diameter reduces toward the tip at the end portion of the tip portion 1A side in the longitudinal direction. (Namely, the tip portion 1A has a tapered shape.)

Figure 4D:
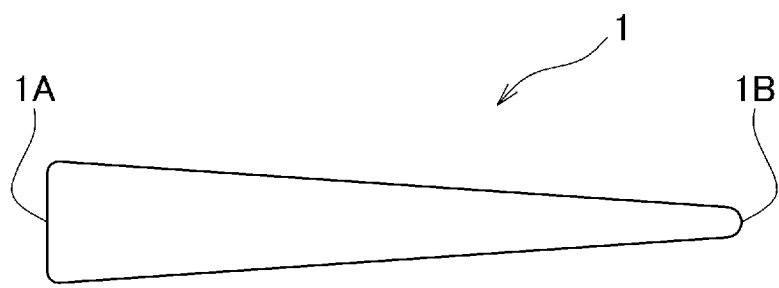
FIG. 4D is a schematic side view showing another example of an entire shape of the adhesive plaster structure of the present invention.

In the embodiment of FIG. 4D, the shape of the adhesive plaster structure 1 is an approximately rod-shape having a diameter reducing from the tip portion 1A to the rear end portion 1B in the longitudinal direction. (Namely, the adhesive plaster structure 1 has a tapered shape from the tip portion 1A to the rear end portion 1B.)

Figure 4E:
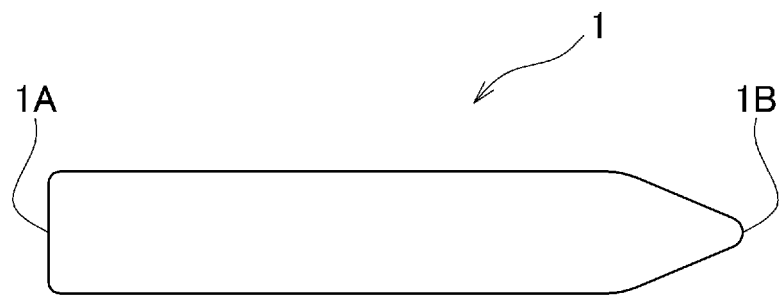
FIG. 4E is a schematic side view showing another example of an entire shape of the adhesive plaster structure of the present invention.

In the embodiment of FIG. 4E, the shape of the adhesive plaster structure 1 is an approximately rod-shape where a diameter reduces toward the tip at the end portion of the rear end portion 1B side in the longitudinal direction. (Namely, the rear end portion 1B has a tapered shape.)

Figure 4F:
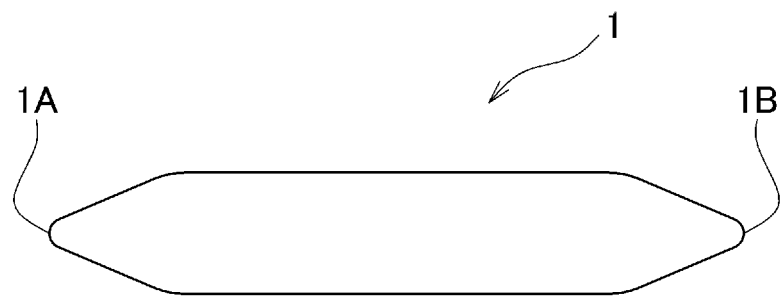
FIG. 4F is a schematic side view showing another example of an entire shape of the adhesive plaster structure of the present invention.

In the embodiment of FIG. 4F, the shape of the adhesive plaster structure 1 is an approximately rod-shape where a diameter reduces toward the tip at both the end portion of the tip portion 1A side and the end portion of the rear end portion 1B side in the longitudinal direction. (Namely, both the tip portion 1A and the rear end portion 1B have a tapered shape.)

Figure 4G:
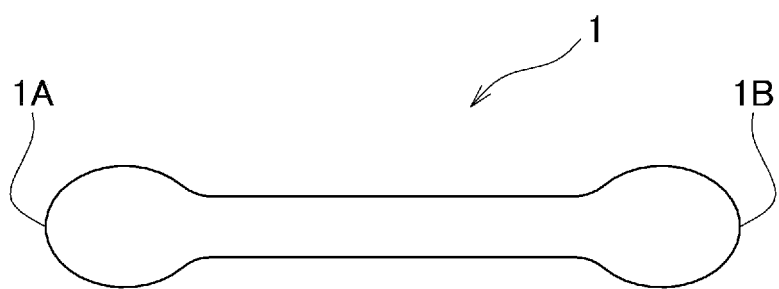
FIG. 4G is a schematic side view showing another example of an entire shape of the adhesive plaster structure of the present invention.

In the embodiment of FIG. 4G, the shape of the adhesive plaster structure 1 is an approximately rod-shape having a spherical swelling at both the end portion of the tip portion 1A side and the end portion of the rear end portion 1B side. (Namely, the adhesive plaster structure 1 has a dumbbell-shape.)

Figure 4H:
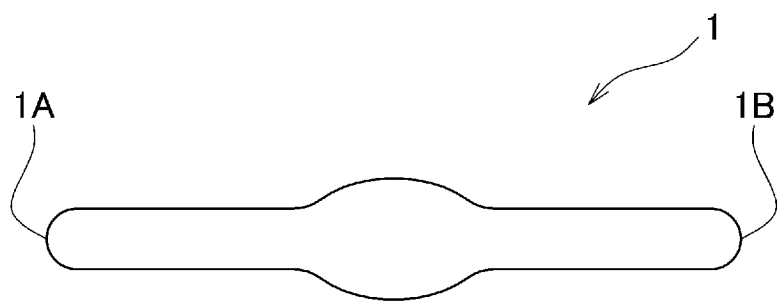
FIG. 4H is a schematic side view showing another example of an entire shape of the adhesive plaster structure of the present invention.

In the embodiment of FIG. 4H, the shape of the adhesive plaster structure 1 is an approximately rod-shape having a spherical swelling at an intermediate region between the tip portion 1A and the rear end portion 1B.

In general, from the viewpoint of easiness of attaching the adhesive plaster structure 1 of the present invention to the finger/toe, the tip portion 1A of the adhesive plaster structure 1 preferably has a tapered shape in many cases, i.e., the embodiments shown in FIG. 4B, FIG. 4C and FIG. 4F. However, the easiness of attaching is not always determined only by the shape of the tip portion 1A. The easiness of attaching relates to various factors such as the position (position in the longitudinal direction of the nail) and condition of wound to be treated, the material used for the adhesive plaster structure 1, and the subjective view of the operator who attaches the adhesive plaster structure 1 to the finger/toe. Accordingly, the entire shape of the adhesive plaster structure 1 can be arbitrarily selected based on integrated determination. However, regardless of the entire shape of the adhesive plaster structure 1, the operator having an ordinary knowledge and skill in the treatment of the ingrown nail can attach the adhesive plaster structure 1 to the finger/toe of the patient easily and correctly. Thus, the wound caused by the ingrown nail can be immediately and easily cured.

The entire shape of the adhesive plaster structure of the present invention is not limited to the examples shown in FIG. 4A to FIG. 4H. As long as the purpose of the present invention is attained, various entire shapes can be further used. For example, the adhesive plaster structure of the present invention can have a flat-shape, a plate-shape or a sheet-shape both before and after attaching the adhesive plaster structure to the finger/toe.

Figure 5A:
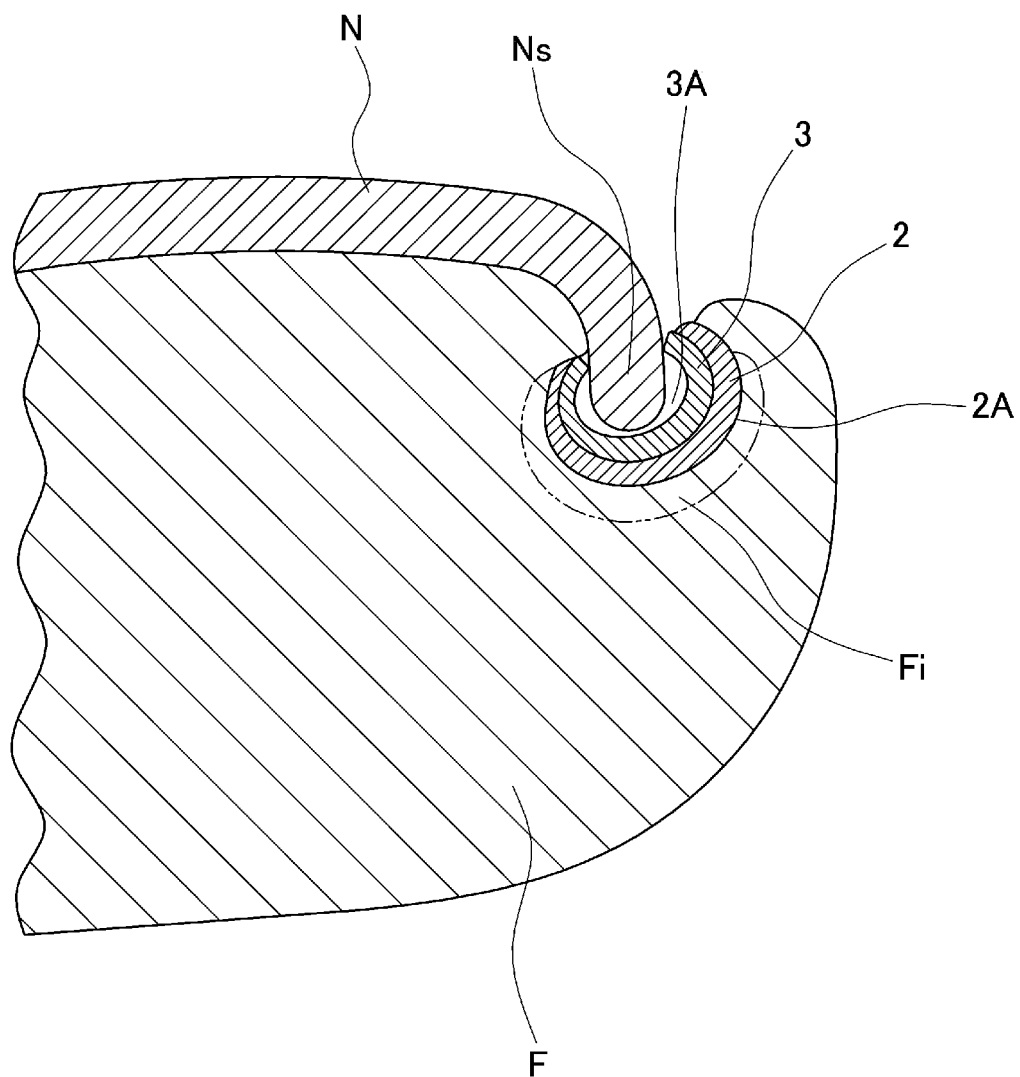
FIG. 5A is a partial schematic cross-sectional view in the direction crossing the longitudinal direction of the finger/toe and the nail showing an example of the adhesive plaster structure of the present invention in a state of being attached to the finger/toe.

FIG. 5A is a partial schematic cross-sectional view in the direction crossing the longitudinal direction of the finger/toe and the nail showing an example of the adhesive plaster structure of the present invention in a state of being attached to the finger/toe. In the embodiment shown in FIG. 5A, the adhesive plaster structure attached to a finger/toe F having an ingrown nail N from the tip side along a lateral nail edge Ns (lateral edge of the nail) is arranged between the lateral nail edge Ns and a wound site Fi (indicated by two-dot chain line) neighboring the lateral nail edge Ns so that the slide groove 3A of the guide area 3 receives the lateral nail edge Ns and the flexible wound adhesion surface 2A of the wound adhesion area 2 is adhered to the wound site Fi stably.

Figure 5B:
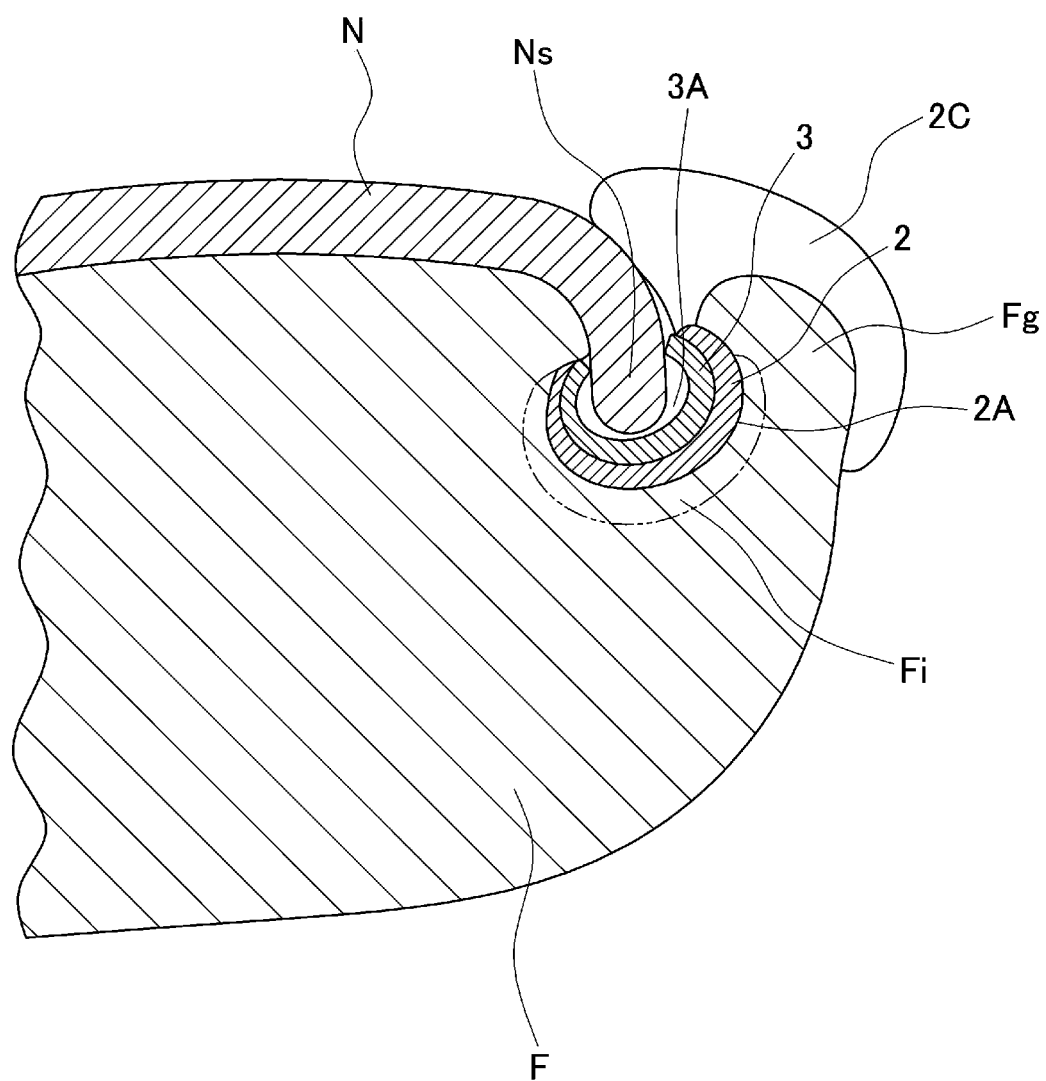
FIG. 5B is a partial schematic cross-sectional view in the direction crossing the longitudinal direction of the finger/toe and the nail showing another example of the adhesive plaster structure of the present invention in a state of being attached to the finger/toe.

FIG. 5B is a partial schematic cross-sectional view in the direction crossing the longitudinal direction of the finger/toe and the nail showing another example of the adhesive plaster structure of the present invention in a state of being attached to the finger/toe. In the embodiment shown in FIG. 5B, in addition to the configurations shown in FIG. 5A, the wound adhesion area 2 has an overhang portion 2C for covering and protecting granuloma Fg caused by the influence of the wound site Fi.

Figure 5C:
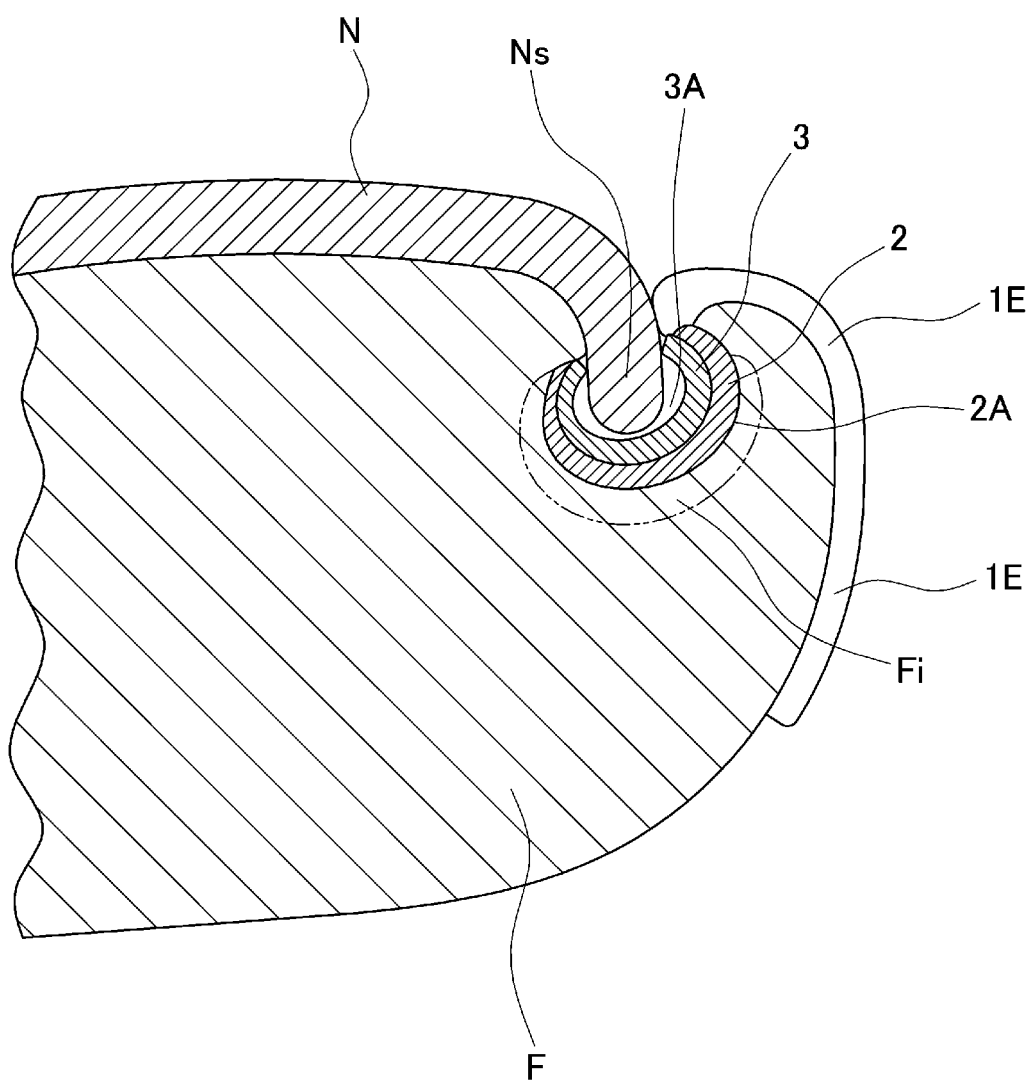
FIG. 5C is a partial schematic cross-sectional view in the direction crossing the longitudinal direction of the finger/toe and the nail showing another example of the adhesive plaster structure of the present invention in a state of being attached to the finger/toe.

FIG. 5C is a partial schematic cross-sectional view in the direction crossing the longitudinal direction of the finger/toe and the nail showing another example of the adhesive plaster structure of the present invention in a state of being attached to the finger/toe. In the embodiment shown in FIG. 5C, in addition to the configurations shown in FIG. 5A, an overhang portion 1E for holding the adhesive plaster structure on a finger/toe is further provided. The overhang portion 1E preferably has a flexibility capable of following the shape of the finger/toe and change of the shape. The overhang portion 1E can be formed, for example, by a tape or a sheet having an adhesive surface at a portion for adhesion to the finger/toe.

Although both the wound adhesion area 2 and the guide area 3 appear in the partial schematic cross-sectional views shown in FIG. 5A and FIG. 5B, the flexible wound adhesion surface 2A of the wound adhesion area 2 should be adhered to the wound site Fi to be treated in order to treat the wound caused by the ingrown nail. Accordingly, although both the wound adhesion area 2 and the guide area 3 can appear in any cross-sections crossing the longitudinal direction of the finger/toe and the nail in a state that the adhesive plaster structure of the present invention is attached to the finger/toe, it is not necessary that both the wound adhesion area 2 and the guide area 3 appear. One of them can appear. For example, in the embodiment shown in FIG. 1A, both the wound adhesion area 2 and the guide area 3 extend over the entire length between the tip portion 1A and the rear end portion 1B of the adhesive plaster structure. Therefore, when the adhesive plaster structure of the embodiment shown in FIG. 1A is attached to the finger/toe, both the wound adhesion area 2 and the guide area 3 necessarily appear in any cross-sections crossing the longitudinal direction of the finger/toe and the nail. For example, in the embodiment shown in FIG. 1C, the guide area 3 does not exist at the intermediate region between the tip portion 1A and the rear end portion 1B of the adhesive plaster structure although the wound adhesion area 2 exists. Therefore, when the adhesive plaster structure of the embodiment shown in FIG. 1C is attached to the finger/toe, only the wound adhesion area 2 appears at the intermediate region in the cross-section crossing the longitudinal direction of the finger/toe and the nail. For example, in the embodiment shown in FIG. 1I, the wound adhesion area 2 does not exist at the intermediate region between the tip portion 1A and the rear end portion 1B of the adhesive plaster structure although the guide area 3 exists. Therefore, when the adhesive plaster structure of the embodiment shown in FIG. 1I is attached to the finger/toe, only the guide area 3 appears at the intermediate region in the cross-section crossing the longitudinal direction of the finger/toe and the nail.

In the adhesive plaster structure of the present invention, the wound adhesion area 2 is preferably formed by a soft body and the guide area 3 is preferably formed by a hard body. An examples of the soft body used for the wound adhesion area 2, the soft body can be selected from the group consisting of a hydrogel body, a gauze, a woven fabric, a nonwoven fabric, an absorbent cotton body, a rubber body, a foamed polyurethane body, a sponge body, a fiber body, a resin body having high flexibility and a material body having a property of absorbing and storing body fluid by a porous structure and/or an uneven structure. An examples of the hard body used for the guide area 3, the hard body can be selected from the group consisting of a resin body having low flexibility, a metal body having low flexibility, a hard pulp body, a glass body, a stone material body and a ceramic body.

Hereafter, the material forming the adhesive plaster structure of the present invention will be explained in detail.

The flexible wound adhesion surface 2A of the wound adhesion area 2 is adhered to the wound of the finger/toe caused by the ingrown nail to obtain healing promoting effect and/or healing effect. In the present invention, "flexible surface" can be paraphrased as "surface for obtaining healing promoting effect and/or healing effect." Accordingly, the material forming the wound adhesion area 2 preferably has flexibility, bendability, softness, cushioning property and absorption/storage property of body fluid at least the substantially same level as so-called a wound covering material (dressing material) such as a normal adhesive plaster and a medical pad. (In the present invention, "absorption/storage property of body fluid" means a property of absorbing and storing the body fluid.) As long as the purpose of the present invention is attained, the material forming the wound adhesion area 2 is not particularly limited. In general, the soft body is preferred. In the present invention, "soft body" means a material body which has at least one of properties selected from the group consisting of flexibility, bendability, softness, cushioning property and absorption/storage property of body fluid and is adhered to the wound of the finger/toe caused by the ingrown nail to obtain healing promoting effect and/or healing effect. All material bodies such as a normal adhesive plaster and a medical pad used effectively as the wound covering material (dressing material) can be used as the "soft body" of the present invention. As preferable examples of the soft body used for the wound adhesion area 2, a hydrogel body, a gauze, a woven fabric, a nonwoven fabric, an absorbent cotton body, a rubber body (natural rubber body and synthetic rubber body), a polyurethane body, a foamed polyurethane body, a sponge body (natural sponge body and artificial sponge body), a paper body (sheet body having high flexibility manufactured by agglutinating plant fiber or other fibers), a fiber body, a plant fiber body, a resin fiber body, a glass fiber body, a carbon fiber body, a metal fiber body, a resin body having high flexibility, and metal body having high flexibility can be listed. As further preferable examples of the soft body, material bodies having property of absorbing and storing body fluid based on a porous structure and/or an uneven structure (e.g., fine grooves). In general, the above described material bodies having property of absorbing and storing body fluid are material bodies exhibiting capillary phenomenon.

The above described soft bodies can be used independently or a plurality kinds of soft bodies can be used in combination. For example, the wound adhesion area 2 can have a laminate structure formed by at least two kinds of the above described soft bodies so that the outermost layer serves as the flexible wound adhesion surface 2A. The thickness of each layer of the wound adhesion area 2 in the laminate structure is generally within the range of 0.01 to 10.0 mm, preferably within the range of 0.05 to 5.0 mm, and more preferably within the range of 0.1 to 3.0 mm. As long as the purpose of the present invention is attained, the wound adhesion area 2 can have a nonporous or porous structure. The wound adhesion area 2 and the soft body for the wound adhesion area 2 can have a porous structure and/or an uneven structure (e.g., fine grooves). In addition, they can have property of absorbing and storing body fluid based on the porous structure and/or the uneven structure (e.g., fine grooves). The details of the porous structure and the uneven structure will be explained later.

The kind of the material body of the soft body used for the wound adhesion area 2 is not limited. The material body preferably has a property of absorbing and storing body fluid. When the soft body has a property of absorbing and storing body fluid, the soft body can be attached to the wound more softly and the wound can be kept in a moistening environment by the body fluid. Thus, effect of healing the wound is increased. For obtaining the property of absorbing and storing body fluid, the soft body can be formed by the material body exhibiting capillary phenomenon or the material body having a molecular structure exhibiting high water absorption, for example.

As examples of the material body exhibiting capillary phenomenon, a porous structure body, an uneven structure body (e.g., structure body having a single or a plurality of fine grooves), a fiber body, a fiber assembly, a woven fabric, a nonwoven fabric and a mesh body can be listed. As an example of the porous structure body exhibiting capillary phenomenon, a foamed polyurethane body can be listed. As an example of the preferable commercially available wound covering material (dressing material) having the foamed polyurethane body, the products generally known as "polyurethane foam dressing" in the medical industry can be used. For example, Hydrosite (registered trademark) manufactured by Smith & Nephew K.K., which is Japanese subsidiary of Smith & Nephew (UK), can be listed. As an example of the preferable commercially available wound covering material containing the porous structure body formed, for example, by synthetic resin and cellulose (specifically, mesh sheet and nonwoven fabric sheet), Plusmoist (registered trademark) manufactured by ZUIKO MEDICAL CORPORATION (Japan).

A lot of material bodies having a molecular structure exhibiting high water absorption is known in the medical industry, and these material bodies are generally referred to as "hydrogel body" in the present invention for the sake of convenience. In the present invention, "hydrogel body" is used as a general term including all polymers having a molecular structure exhibiting hydrophilicity and/or water absorbency. These polymers are used for forming a moistening environment in so-called "moistening therapy." From the viewpoint of capacity of absorbing and storing water and body fluid (i.e., ability of absorbing and storing large amount of water and body fluid more stably), the hydrogel body is preferred. The hydrogel body has a property of swelling by water and body fluid. In addition, the hydrogel body has an extremely high swelling ratio (%) (approximately 110 to 1,000%). (The swelling ratio is defined as a value obtained by the following calculation formula: Volume of gel after swelling/Volume of gel before swelling×100.) The swelling ratio (%) of the hydrogel body is extremely high. Accordingly, if the hydrogel body is used as the wound adhesion area 2 in a state that the hydrogel body is not swollen, even if the thickness of the wound adhesion area 2 is thin when attaching the adhesive plaster structure 1 to the finger/toe, the volume of the hydrogel body largely increases after attached to the finger/toe by absorbing the body fluid and swelling. Because of this, the hydrogel body is adhered to the wound more tightly and pushes up the lateral nail edge (lateral edge of the nail). Thus, the effect of correcting the ingrown nail is increased. From the viewpoint of providing an ideal moistening environment and increasing healing effect of the wound, the hydrogel body is particularly preferred as the material of the wound adhesion area 2.

When the hydrogel body is used as the material of the wound adhesion area 2, the method and condition of use can be arbitrarily selected without being particularly limited. For example, the hydrogel body used as the wound adhesion area 2 can be swollen or not swollen before attaching the adhesive plaster structure 1 to the finger/toe. When the hydrogel body is used as the wound adhesion area 2, the above described thickness of the wound adhesion area 2 indicates the value after swelling.

When the hydrogel body used for the wound adhesion area 2 is not swollen before attaching the adhesive plaster structure 1 to the finger/toe, the wound adhesion area 2 may substantially not have a surface to function as the flexible wound adhesion surface 2A at that time. However, the flexible wound adhesion surface 2A is formed enough because the hydrogel body absorbs the body fluid and swells after the adhesive plaster structure 1 is attached to the finger/toe. Accordingly, in the present invention, the flexible wound adhesion surface 2A of the wound adhesion area 2 is not necessary provided before attaching the adhesive plaster structure 1 to the finger/toe. It is enough if the flexible wound adhesion surface 2A is formed after the adhesive plaster structure 1 is attached to the finger/toe. Both before and after attaching the adhesive plaster structure 1 to the finger/toe, in order to swell the hydrogel body used as the wound adhesion area 2, the body fluid, other aqueous liquids than the body fluid, or non-aqueous liquids (e.g., ethanol) can be used.

The hydrogel body is widely used for the wound covering material (dressing material) such as a normal adhesive plaster and a medical pad. As examples of the preferable commercially available hydrogel body for medical purpose, the products generally known as "hydrocolloid dressing" in the medical industry can be used. For example, Duoactive (registered trademark) manufactured by ConvaTec Japan, which is Japanese subsidiary of ConvaTec Inc. (USA), Comfeel (registered trademark) manufactured by Coloplast K.K., which is Japanese subsidiary of Coloplast A/S (Denmark), Tegaderm (registered trademark) manufactured by 3M Japan Limited, which is Japanese subsidiary of 3M Company (USA), and Absocure (registered trademark) manufactured by Nitoms, Inc. (Japan) can be listed. As a further example of the preferable commercially available hydrogel body for medical purpose, the products generally known as "hydropolymer dressing" in the medical industry can be used. For example, Tielle (registered trademark) manufactured by Johnson & Johnson K.K., which is Japanese subsidiary of Johnson & Johnson (USA) can be listed. As a further example of the preferable commercially available hydrogel body for medical purpose, the products generally known as "fibrous dressing" and "hydrofiber dressing" in the medical industry can be used. For example, Durafiber (registered trademark) manufactured by Smith & Nephew K.K., which is Japanese subsidiary of Smith & Nephew (UK), can be listed. As a further example of the preferable commercially available hydrogel body for medical purpose, the products generally known as "hydrogel dressing" in the medical industry can be used. For example, Intrasite Conformable Dressing (registered trademark) manufactured by Smith & Nephew K.K., which is Japanese subsidiary of Smith & Nephew (UK), can be listed. As a further example of the preferable commercially available hydrogel body for medical purpose, the products generally known as "alginate dressing" in the medical industry can be used. For example, Kaltostat (registered trademark) manufactured by ConvaTec Japan, which is Japanese subsidiary of ConvaTec Inc. (USA), and Sorbsan (registered trademark) manufactured by ALCARE Co., Ltd. (Japan), can be listed. (The commercially available hydrogel bodies for medical purpose exemplified above are not initially swollen except for "Intrasite Conformable Dressing" (registered trademark)). These hydrogel bodies are not initially swollen and are swollen after applied to the wound by the body fluid exuded from the wound. "Intrasite Conformable Dressing" (registered trademark) is a dressing obtained by impregnating hydrogel (jelly-like) swollen by water into a nonwoven fabric gauze. Namely, it is initially swollen.)

As long as the purpose of the present invention is attained, the shape of the wound adhesion area 2 is not particularly limited. However, in general, the shape can have a cross-section similar to the wound adhesion area 2 shown in FIG. 3A to FIG. 3R, for example. As long as both the wound adhesion area 2 and the guide area 3 can perform their functions after the adhesive plaster structure of the present invention is attached to the finger/toe, the wound adhesion area 2 can cover the whole of the guide area 3, for example (shown in FIG. 3O and FIG. 3P). Alternatively, the wound adhesion area 2 can cover a part or the whole of a corner portion or an edge portion of the guide area 3 since these portions have possibility to make contact with the flesh (soft tissue) of the finger/toe at a relatively sharp angle when attaching or after attaching the adhesive plaster structure 1 of the present invention to the finger/toe (shown in FIG. 9). The method of making the wound adhesion area 2 is not particularly limited. Conventionally know processing methods can be arbitrarily selected according to the material to be used and the desired shape. As examples of the conventionally know processing methods, when resins or similar materials are used, molding (e.g., injection molding, compression molding), bending, machining, and processing by laser beam can be listed. When ceramics or similar materials are used, method sintering to a desired shape, machining, and processing by laser beam can be listed. When metals or similar materials are used, the conventionally known methods (e.g., die casting method, press method, sand casting method, forging method, machining, processing by laser beam, powder metallurgy method) can be used. In addition, coating method can be also used. Furthermore, it can be made by a three-dimensional (3D) printer (laminate shaping method) or a three-dimensional (3D) plotter (cutting shaping method).

As long as the purpose of the present invention is attained, the surface shape of the wound adhesion area 2 is not particularly limited. As examples of the surface shape of the wound adhesion area 2, a planar shape, a curved shape, a spherical shape, an uneven shape, a regular shape, an irregular shape, and a combination of the above shapes can be listed.

As long as the purpose of the present invention is attained, the shape of the edge portions of the wound adhesion area 2 is not particularly limited. As examples of the shape of the edge portions of the wound adhesion area 2, a linear shape, a curved shape, an arc shape, a regular shape, an irregular shape, a waved shape, a zigzag shape, and a combination of the above shapes can be listed.

As examples of the metal fiber body and the metal body having low flexibility, which are the preferable soft bodies, are not particularly limited as long as it is not harmful to a living body. For example, aluminum, silver, copper, gold, platinum, palladium, indium, iridium, iron, tin, cobalt, chromium, nickel, titanium, and alloy of the above metals can be listed. As examples of the alloy, silver alloy, gold-silver-palladium alloy, gold alloy, alloy for baking ceramic, cobalt-chromium alloy, nickel-chromium alloy, and titanium alloy can be listed, for example.

As examples of the resin body having high flexibility, which is the preferable soft body, a tubular body made of synthetic resin material (hereafter, often referred to as "plastic material") and material bodies obtained by cutting a side wall of the tubular body in the longitudinal direction to have a cross-sectional shape of a C-shape, a U-shape, an arc shape (e.g., semi-arc shape), an approximately arc shape (e.g., approximately semi-arc shape), and an L-shape can be listed. According to surprising knowledge of the inventor in a developing process of the present invention, in the adhesive plaster structure of the present invention, the tubular body made of the plastic material and the wound adhesion area 2 made of the material body obtained from the tubular body not only exhibit flexibility by itself but also exhibit physical and mechanical interaction with the guide area 3. Thus, the adhesive plaster structure as a whole exhibits flexibility, bendability, softness and cushioning property to the wound superior to those properties of the wound adhesion area 2 itself.

As examples of the plastic materials forming the tubular body, polycarbonate, ABS resin (acrylonitrile-butadiene-styrene copolymer), polyethylene, polypropylene, polyethylene terephthalate, vinyl acetate, polyvinyl chloride, urethane-based resin, nylon, nylon elastomer, polyamide, tenite acetate, silicone rubber, silicone resin, fluororesin (e.g., polytetrafluoroethylene), acrylic-based resin, polyether sulfone resin (PES), polyphenyl sulfone resin (PPSU), and all polymers generally used for a living body in the medical field can be listed. These resins can be used independently or used in combination. As more specific examples, Styrolux (registered trademark) 684D which is styrene-butadiene block copolymer (SBC) available from BASF Corporation (USA), Cryro (registered trademark) R40 (acrylic base) which is acrylic-based multipolymer available from Cyro Industries (USA), Lexan KR01 which is polycarbonate available from SABIC Innovative Plastics (USA), K-resin (registered trademark) which is styrene-butadiene copolymer (SBC) available from Chevron Phillips Chemical Company (USA), TP-UXS (MMBS) (trade name) which is methyl methacrylate butadiene styrene terpolymer available from Denka Company Limited (Japan), Starex (registered trademark) 5010 which is acrylonitrile-butadiene-styrene resin (ABS) available from Samsung Cheil Industries (Korea), Zylar (registered trademark) 220 and Nas (registered trademark) 30 which are styrene-methyl methacrylic acid (SMMS) available from NOVA Chemicals (Canada), and Toyalac 920 (transparent ABS) which is acrylonitrile-butadiene-styrene (ABS) available from Toray Resin Company (USA) can be listed. As an example of mixing two or more kinds of resins, a mixture of ABS resin and polycarbonate can be listed.

As long as the purpose of the present invention is attained, the size of the tubular body is not particularly limited. However, the outer diameter is preferably within the range of 0.8 to 10 mm, the inner diameter is preferably within the range of 0.5 to 5 mm. As the tubular body made of the plastic material, medical infusion tubes used broadly in the medical field can be preferably used. Many kinds of products are commercially available as the medical infusion tube. As preferable examples of commercially available medical infusion tube, tubes included in "Nipro Infusion Set" manufactured by NIPRO CORPORATION (Japan), and tubes included in "Infusion Set for Pump" manufactured by TERUMO CORPORATION (Japan), and "Extension Tubes" manufactured by JMS Co., Ltd. (Japan) can be listed, for example. If a medical plastic tube having a special specification not commercially available should be obtained, it can be ordered to a commission manufacturer of medical instruments, for example. As an example of the commission manufacturer of medical instruments, HAGITEC LTD. (Japan) can be listed.

When the tubular body (or the material body obtained by cutting a side wall of the tubular body in the longitudinal direction to have a cross-sectional shape of a C-shape and a U-shape) made of the plastic material is used as the soft body of the wound adhesion area 2, it is preferred that a processing to increase bendability and property of absorbing and storing body fluid is applied to the portion to function as the flexible wound adhesion surface 2A. Because of such a processing, the flexible surface 2A is more tightly adhered to the wound and the wound can be kept in a moistening environment by the body fluid. Thus, effect of healing the wound is increased. As examples of the processing to increase bendability and property of absorbing and storing body fluid, at least an outer surface of the side wall of the tubular body can be made porous, or an uneven structure such as a single or a plurality of fine grooves is formed on at least an outer surface of the side wall of the tubular body. When the tubular body is made porous, the depth of pores is preferably 0.1 mm or more. The diameter of pores is preferably within the range of 0.02 to 4.0 mm, more preferably within the range of 0.05 to 1.5 mm, and more preferably within the range of 0.1 to 0.5 mm. The interval between pores is preferably within the range of 0.1 to 2.0 mm. The pores can be arranged regularly or randomly. The shape of the pores extending in the side wall of the tubular body can be a linear shape or a curved shape. The pores can penetrate through the side wall of the tubular body or can be non-penetrating. As long as the property of absorbing and storing body fluid can be obtained, details of the pores are not particularly limited. As long as the property of absorbing and storing body fluid can be obtained, the pores can be continuous pores, non-continuous pores (closed pores), or a combination of the continuous pores and the non-continuous pores. When the fine grooves are formed, the depth of the grooves is preferably 0.1 mm or more. The depth of the grooves is preferably within the range of 0.02 to 4.0 mm, more preferably within the range of 0.05 to 1.5 mm, more preferably within the range of 0.1 to 0.5 mm. The length of the grooves is preferably within the range of 0.1 to 10.0 mm, and the interval between the grooves is preferably within the range of 0.1 to 2.0 mm. The grooves can be arranged regularly or randomly. The grooves can be crossed with each other or can be non-crossing. The grooves can be a linear shape or a curved shape. The grooves can penetrate through the side wall of the tubular body or can be non-penetrating. As long as the property of absorbing and storing body fluid can be obtained, details of the uneven structure such as fine grooves are not particularly limited. The method of making the tubular body porous is not particularly limited. Conventionally known methods can be used. As the conventionally known methods of making the tubular body porous, phase separation method, extraction method, chemical treatment method, drawing method, irradiation etching method (using neutron beam, laser beam or the like), fusing method, foaming method, surface treatment, boring by pushing needle-like body, and a combination of the above methods can be listed. The method of forming the uneven structure such as the fine grooves is not particularly limited. Conventionally known methods (e.g., forming method by molding, forming method by laser beam, forming method by knife, forming method by dicing, and forming method by etching) can be used.

Figure 7A:
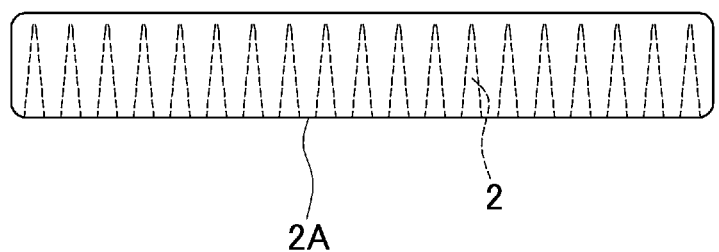
FIG. 7A is a schematic cross-sectional view showing a state that at least an outer surface of a side wall of a tubular body, which is used as a soft body for the wound adhesion area, is made porous.
Figure 7B:
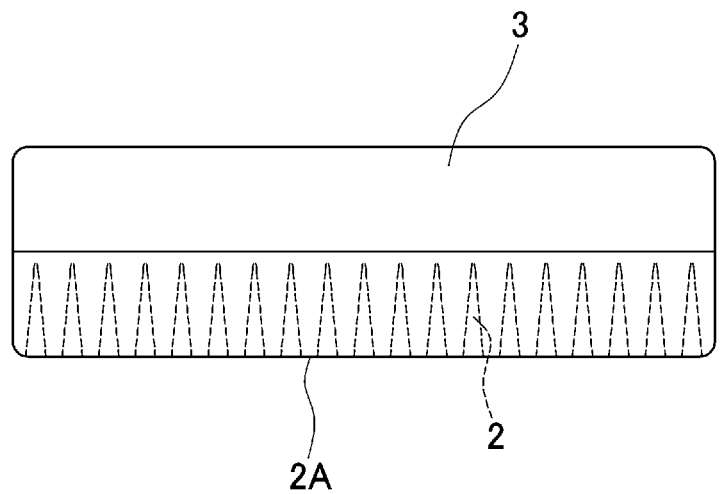
FIG. 7B is a schematic cross-sectional view of a structure formed by combining the wound adhesion area (soft body) shown in FIG. 7A with the guide area (hard body).
Figure 7C:
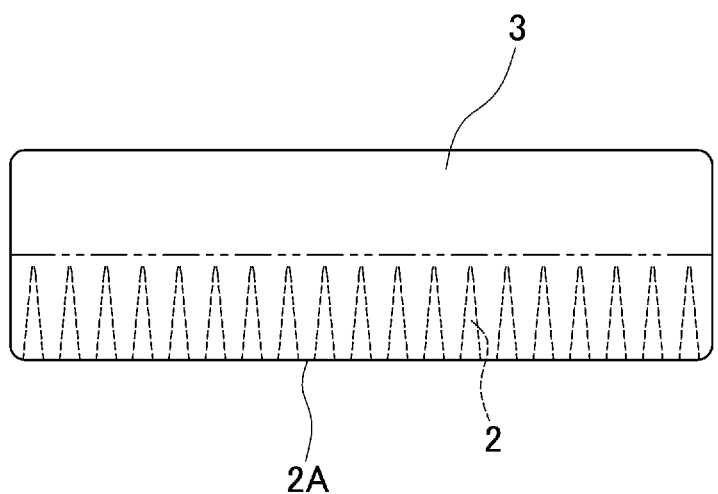
FIG. 7C is a schematic cross-sectional view of a structure formed by integrally combining the wound adhesion area (soft body) and the guide area (hard body) in a state that only a lower layer of one material is made porous.

FIG. 7A is a schematic cross-sectional view showing a state that at least an outer surface of the side wall of the tubular body (or the material body obtained by cutting a side wall of the tubular body in the longitudinal direction to have a cross-sectional shape of a C-shape and a U-shape), which is used as the soft body for the wound adhesion area 2, is made porous. The vertical direction of FIG. 7A is the thickness direction of the side wall of the tubular body. The portion of the pores is shown by broken lines in FIG. 7A. FIG. 7B shows a structure formed by combining the wound adhesion area 2 (soft body) shown in FIG. 7A with the guide area 3 (hard body). FIG. 7C shows a structure formed by integrally combining the wound adhesion area 2 (soft body) and the guide area 3 (hard body) in a state that only a lower layer (a part lower than the two-dot chain line extending in a horizontal direction) of one material is made porous. In the embodiments shown in FIG. 7A to FIG. 7C, the uneven structure such as fine grooves can be formed instead of making the tubular body porous.

About the material bodies having property of absorbing and storing body fluid based on a porous structure and/or an uneven structure, as the preferable soft body, the material is not particularly limited. As examples of the material of the material bodies, various materials such as a resin, a rubber, a metal, a hard pulp, a wood, a plant fiber, a cellulose, a glass, a stone and a ceramic can be listed. In case of the porous structure, the depth of the pores is preferably 0.1 mm or more. The diameter of the pores is preferably within the range of 0.02 to 4.0 mm, more preferably within the range of 0.05 to 1.5 mm, and more preferably within the range of 0.1 to 0.5 mm. The interval between pores is preferably within the range of 0.1 to 2.0 mm. The pores can be arranged regularly or randomly. The shape of the pores extending in the tubular body can be a linear shape or a curved shape. The pores can penetrate through the tubular body or can be non-penetrating. As long as the property of absorbing and storing body fluid can be obtained, details of the pores are not particularly limited. As long as the property of absorbing and storing body fluid can be obtained, the pores can be continuous pores, non-continuous pores (closed pores), or a combination of the continuous pores and the non-continuous pores. The uneven structure can be a single or a plurality of fine grooves, for example. The depth of the grooves is preferably 0.1 mm or more. The width of the grooves is preferably within the range of 0.02 to 4.0 mm, more preferably within the range of 0.05 to 1.5 mm, and more preferably within the range of 0.1 to 0.5 mm. The length of the grooves is preferably within the range of 0.1 to 10.0 mm, and the interval between the grooves is preferably within the range of 0.1 to 2.0 mm. The grooves can be arranged regularly or randomly. The grooves can be crossed with each other or can be non-crossing. The grooves can be a linear shape or a curved shape. The grooves can penetrate through the side wall of the tubular body or can be non-penetrating. As long as the property of absorbing and storing body fluid can be obtained, details of the uneven structure such as the grooves are not particularly limited. The method of making the tubular body porous is not particularly limited. Conventionally known methods can be used. As the conventionally known methods of making the tubular body porous, phase separation method, extraction method, chemical treatment method, drawing method, irradiation etching method (using neutron beam, laser beam or the like), fusing method, foaming method, surface treatment, boring by pushing needle-like body, and a combination of the above methods can be listed. The method of forming the uneven structure such as the fine grooves is not particularly limited. Conventionally known methods (e.g., forming method by molding, forming method by laser beam, forming method by knife, forming method by dicing, and forming method by etching) can be used.

In the adhesive plaster structure of the present invention, the slide groove 3A of the guide area 3 receives the lateral edge portion of the nail (the lateral nail edge) and slid in the longitudinal direction of the nail along the lateral nail edge, for example. Thus, the flexible wound adhesion surface 2A of the wound adhesion area 2 is surely guided to the wound site. Accordingly, the material forming the guide area 3 should have durability and/or rigidity satisfying the above purpose. As long as the purpose of the present invention is attained, the material forming the guide area 3 is not particularly limited. In general, the hard body is preferred. In the present invention, "hard body" means a material body which has at least one of properties selected from the group consisting of low flexibility, low bendability and low softness and has durability and/or rigidity enabling to surely guide the flexible wound adhesion surface 2A of the wound adhesion area 2 to the wound site. As preferable examples of the hard body used for the guide area 3, a resin body having low flexibility, a metal body having low flexibility, a hard pulp body, a wood body, a glass body, a stone material body, a ceramic body, a glass fiber body, a carbon fiber body, and a metal fiber body can be listed. These hard bodies can be used independently or used in combination. For example, the guide area 3 can have a laminate structure formed by at least two kinds of the above described hard bodies so that the outermost layer serves as the slide groove 3A. The thickness of each layer of the guide area 3 in the laminate structure is generally within the range of 0.01 to 5.0 mm, preferably within the range of 0.05 to 2.0 mm, and more preferably within the range of 0.1 to 1.0 mm. As long as the purpose of the present invention is attained, the guide area 3 can have a nonporous or porous structure. The guide area 3 and the hard body for the guide area 3 can have a porous structure and/or an uneven structure (e.g., fine grooves). In addition, they can have property of absorbing and storing body fluid based on the porous structure and/or the uneven structure (e.g., fine grooves). About details of the porous structure and the uneven structure, the explanation made for the wound adhesion area 2 is also applied here.

As long as the purpose of the present invention is attained, the resin body having low flexibility, as the preferable hard body, is not particularly limited. For example, various resin bodies made of the plastic material can be used. As examples of the plastic material, polycarbonate, ABS resin (acrylonitrile-butadiene-styrene copolymer), polyethylene, polypropylene, polyethylene terephthalate, vinyl acetate, polyvinyl chloride, urethane-based resin, nylon, nylon elastomer, polyamide, tenite acetate, silicone rubber, silicone resin, fluororesin (e.g., polytetrafluoroethylene), acrylic-based resin, polyether sulfone resin (PES), polyphenyl sulfone resin (PPSU), and all polymers generally used for a living body in the medical field can be listed. These resins can be used independently or used in combination. As more specific examples, Styrolux (registered trademark) 684D which is styrene-butadiene block copolymer (SBC) available from BASF Corporation (USA), Cryro (registered trademark) R40 (acrylic base) which is acrylic-based multipolymer available from Cyro Industries (USA), Lexan KR01 which is polycarbonate available from SABIC Innovative Plastics (USA), K-resin (registered trademark) which is styrene-butadiene copolymer (SBC) available from Chevron Phillips Chemical Company (USA), TP-UXS (MMBS) (trade name) which is methyl methacrylate butadiene styrene terpolymer available from Denka Company Limited (Japan), Starex (registered trademark) 5010 which is acrylonitrile-butadiene-styrene resin (ABS) available from Samsung Cheil Industries (Korea), Zylar (registered trademark) 220 and Nas (registered trademark) 30 which are styrene-methyl methacrylic acid (SMMS) available from NOVA Chemicals (Canada), and Toyalac 920 (transparent ABS) which is acrylonitrile-butadiene-styrene (ABS) available from Toray Resin Company (USA) can be listed. As an example of mixing two or more kinds of resins, a mixture of ABS resin and polycarbonate can be listed.

As examples of the resin body having low flexibility which is preferable hard body, the material bodies same as the material bodies listed as the resin body having high flexibility which is preferable soft body can be listed. Namely, the tubular body made of the plastic material and the material body obtained by cutting a side wall of the tubular body in the longitudinal direction to have a cross-sectional shape of a C-shape, a U-shape, an arc shape (e.g., semi-arc shape), an approximately arc shape (e.g., approximately semi-arc shape), or an L-shape can be listed. About the material, size and commercially available products of the tubular body, the explanation made for the tubular body, which is the example of the preferred resin body having high flexibility, is also applied. Both the wound adhesion area 2 (soft body) and the guide area 3 (hard body) can be formed by the same kind of material body because the tubular body made of the plastic material and the wound adhesion area 2 made of the material body obtained from the tubular body not only exhibit flexibility by itself but also exhibit physical and mechanical interaction with the guide area 3 and the adhesive plaster structure as a whole exhibits flexibility, bendability, softness and cushioning property to the wound superior to those properties of the wound adhesion area 2 itself in the adhesive plaster structure of the present invention according to surprising knowledge of the inventor in a developing process of the present invention as described above. Accordingly, even when both the wound adhesion area 2 (soft body) and the guide area 3 (hard body) are formed by the same kind of material body, the adhesive plaster structure as a whole exhibits flexibility, bendability, softness and cushioning property to the wound superior to those properties of the wound adhesion area 2 itself. From the viewpoint of improving flexibility, bendability, softness and cushioning property, when both the wound adhesion area 2 (soft body) and the guide area 3 (hard body) are formed by the same kind of material body, as the positional relation between the wound adhesion area 2 and the guide area 3, the gap G is preferably formed between them as shown in FIG. 3H, FIG. 3I and FIG. 3J, for example. The details of the gap G have already been explained.

As examples of the metal fiber body and the metal body having low flexibility, which are the preferable hard bodies, they are not particularly limited as long as they are not harmful to a living body. For example, aluminum, silver, copper, gold, platinum, palladium, indium, iridium, iron, tin, cobalt, chromium, nickel, titanium, and alloy of the above metals can be listed. As examples of the alloy, silver alloy, gold-silver-palladium alloy, gold alloy, alloy for baking ceramic, cobalt-chromium alloy, nickel-chromium alloy, and titanium alloy can be listed, for example.

As long as the purpose of the present invention is attained, the shape of the guide area 3 is not particularly limited. However, in general, the shape can have a cross-section similar to the guide area 3 shown in FIG. 3A to FIG. 3R, for example. The method of making the guide area 3 is not particularly limited. Conventionally know processing methods can be arbitrarily selected according to the material to be used and the desired shape. As examples of the conventionally know processing methods, when resins or similar materials are used, molding (e.g., injection molding, compression molding), bending, machining, and processing by laser beam can be listed. When ceramics or similar materials are used, method sintering to a desired shape, machining, and processing by laser beam can be listed. When metals or similar materials are used, the conventionally known methods (e.g., die casting method, press method, sand casting method, forging method, machining, processing by laser beam, powder metallurgy method) can be used. In addition, coating method can be also used. Furthermore, it can be made by a three-dimensional (3D) printer (laminate shaping method) or a three-dimensional (3D) plotter (cutting shaping method).

As long as the purpose of the present invention is attained, the surface shape of the guide area 3 is not particularly limited. As examples of the surface shape of the guide area 3, a planar shape, a curved shape, a spherical shape, an uneven shape, a regular shape, an irregular shape, and a combination of the above shapes can be listed.

As long as the purpose of the present invention is attained, the shape of the edge portions of the guide area 3 is not particularly limited. As examples of the shape of the edge portions of the guide area 3, a linear shape, a curved shape, an arc shape, a regular shape, an irregular shape, a waved shape, a zigzag shape, and a combination of the above shapes can be listed.

Figure 6A:
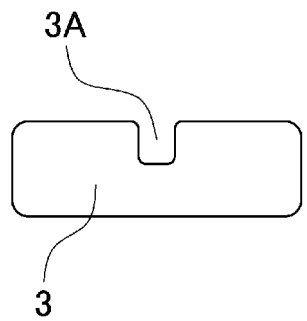
FIGS. 6A to 6E are schematic cross-sectional views showing five examples of cross-sectional shapes of a slide groove 3A of a guide area 3.
Figure 6B:
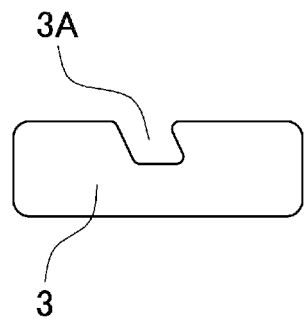
Figure 6C:
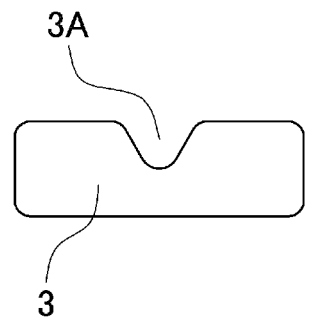
Figure 6D:
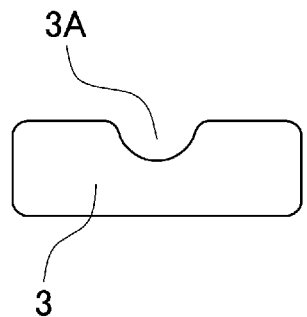
Figure 6E:
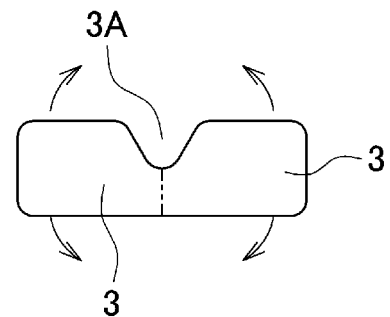

As long as the purpose of the present invention is attained, the shape of the slide groove 3A of the guide area 3 is not particularly limited. The cross-sectional shape of the slide groove 3A can be shapes shown in FIG. 3A to FIG. 3R, for example. As further examples of the cross-sectional shape of the slide groove 3A, the shapes shown in FIGS. 6A to 6E can be listed. In the embodiment shown in FIG. 6E, the portion shown by two-dot chain line located at the bottom portion of the slide groove 3A has high flexibility and the guide area 3 is bendable (pivottable) in the direction of an arrow along the axis in the longitudinal direction of the slide groove 3A. In addition, the guide area 3 can be bendable (pivottable) along the axis in the direction crossing the longitudinal direction of the slide groove 3A, if desired. When the guide area 3 is bendable, structural freedom of the adhesive plaster structure 1 is increased. Thus, freedom of attaching method of the adhesive plaster structure 1 to the finger/toe and range of applicable cases are further increased. When the guide area 3 is bendable (pivottable), the wound adhesion area 2 is also formed to be bendable (pivottable) to follow the guide area 3.

As long as the purpose of the present invention is attained, the shape of the extending shape of the slide groove 3A of the guide area 3 is not particularly limited. As examples of the extending shape of the slide groove 3A, a linear shape, a curved shape, an arc shape, a regular shape, an irregular shape, a waved shape, a zigzag shape, and a combination of the above shapes can be listed.

For both the wound adhesion area 2 and the guide area 3, a part or the whole of them can be made of a cellulose. The cellulose can be a general cellulose, a nanocellulose, or a combination of the general cellulose and the nanocellulose. As examples of the nanocellulose, cellulose nanofiber (CNF) (width: approximately 4 to 100 nm, length: approximately 5 μm or more), cellulose nanocrystals (CNC) (width: approximately 10 to 50 nm, length: approximately 100 to 1000 nm), and bacterial nanocellulose (BNC) (nanocellulose produced by microorganisms) can be listed.

As long as the purpose of the present invention is attained, the method of combining the wound adhesion area 2 and the guide area 3 with each other is not particularly limited. Conventionally known combining methods can be used. As examples of the combining methods, bonding, fusion, welding and fitting can be listed, for example. In addition, for example, as shown in FIG. 7C, when only the lower layer (a part lower than the two-dot chain line extending in a horizontal direction) of one material is made porous, the wound adhesion area 2 (soft body) and the guide area 3 (hard body) can be integrally formed. (As explained above, in the embodiments shown in FIG. 7A to FIG. 7C, the uneven structure such as fine grooves can be formed instead of making the tubular body porous.) Furthermore, for example, when the porous structure and/or the uneven structure (e.g., fine grooves) are applied to the whole of one material, the wound adhesion area 2 (soft body) and the guide area 3 (hard body) can be integrally formed. (In this case, it is necessary to use the hard body having durability and/or rigidity enabling to keep functions of the guide area 3 even when the porous structure and/or the uneven structure are applied.) (About details of the porous structure and the uneven structure, the explanation made for the wound adhesion area 2 and the guide area 3 is also applied here.) Furthermore, for example, when the material forming the wound adhesion area 2 is provided as liquid (i.e., solution, dispersion, melt or the like), the wound adhesion area 2 and the guide area 3 can be integrally formed by coating the liquid on a desired area of the guide area 3 and drying or solidifying the liquid. When at least one of the wound adhesion area 2 and the guide area 3 has an adhesiveness effective for combining them with each other, the adhesiveness can be used for combining them. The wound adhesion area 2 and the guide area 3 can be integrally formed by a three-dimensional (3D) printer (laminate shaping method) and/or a three-dimensional (3D) plotter (cutting shaping method).

Conventionally known adhesive agents can be used as an adhesive agent when adhering the wound adhesion area 2 and the guide area 3 with each other. As an example of the conventionally known adhesive agent, "Aron Alpha" (registered trademark) manufactured by Toagosei Co., Ltd. (Japan) can be listed. As an example of particularly preferred adhesive agent, Aron Alpha A "Sankyo" (registered trademark) which is an adhesive agent for medical use and manufactured by Toagosei Co., Ltd. (Japan) can be listed. Alternatively, an adhesive agent so-called "nail glue" which is generally used for attaching an artificial nail to one's own nail can be used, for example. Together with the nail glue, an activator (hardening accelerator) can be used for shortening the time required for adhesion. As a specific example of the nail glue, "ibd 5 Second Nail Glue" manufactured by shinwa Corporation (Japan) can be listed. As a specific example of the activator, "MITHOS Activator" manufactured by shinwa Corporation (Japan) can be listed.

Figure 8:
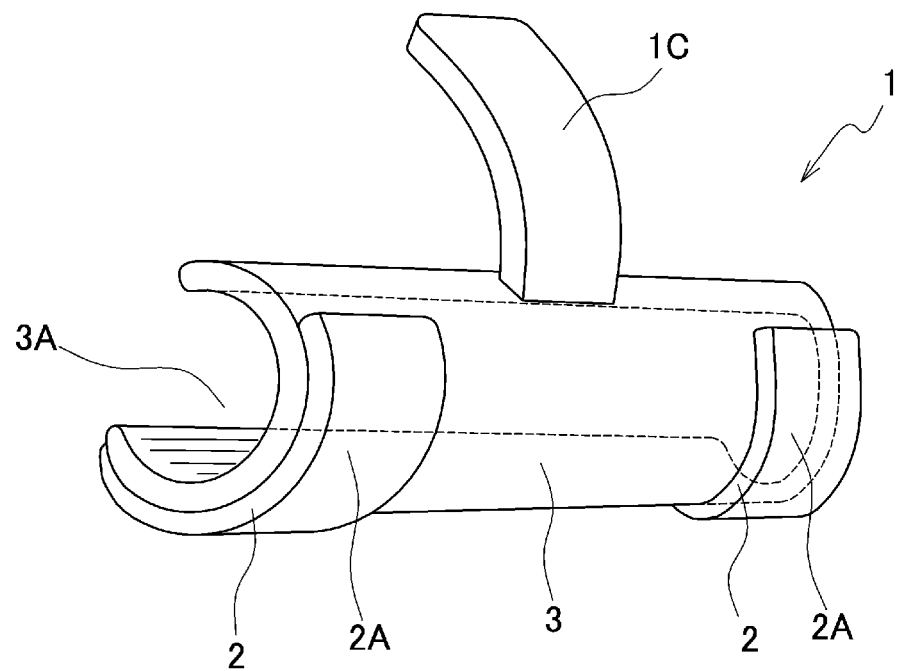
FIG. 8 is a schematic perspective view showing an example of the adhesive plaster structure of the present invention.

FIG. 8 shows a schematic perspective view showing an embodiment of the adhesive plaster structure 1 of the present invention. In the adhesive plaster structure 1 shown in FIG. 8, the guide area 3 has a C-shape in cross section, and the wound adhesion area 2 is arranged on an outer surface of both end portions of the guide area 3. As shown in FIG. 8, the adhesive plaster structure of the present invention can have a handle 1C to facilitate attaching the adhesive plaster structure 1 to the finger/toe.

Figure 9:
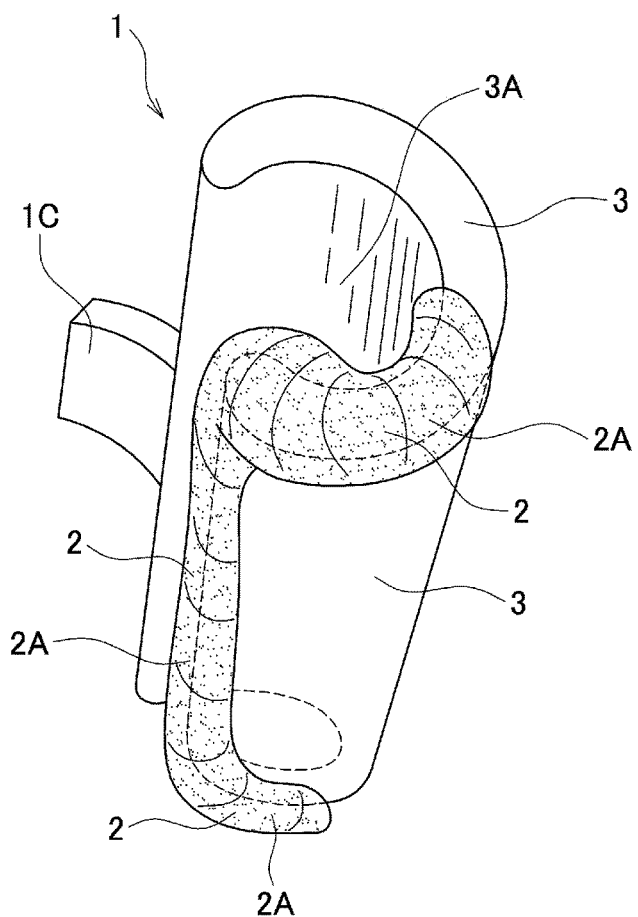
FIG. 9 is a schematic perspective view showing another example of the adhesive plaster structure of the present invention.

FIG. 9 shows a schematic perspective view showing another embodiment of the adhesive plaster structure 1 of the present invention. The adhesive plaster structure 1 shown in FIG. 9 has a structure same as the structure of the adhesive plaster structure 1 shown in FIG. 8 except for that the wound adhesion area 2 is arranged only on one edge portion of the guide area 3 extending in the longitudinal direction and a corner part of both edges of the edge portion. (Namely, the wound adhesion area 2 is arranged only on a portion having possibility to make contact with the flesh (soft tissue) of the finger/toe at a relatively sharp angle when attaching or after attaching the adhesive plaster structure 1 of the present invention to the finger/toe.)

Figure 10:
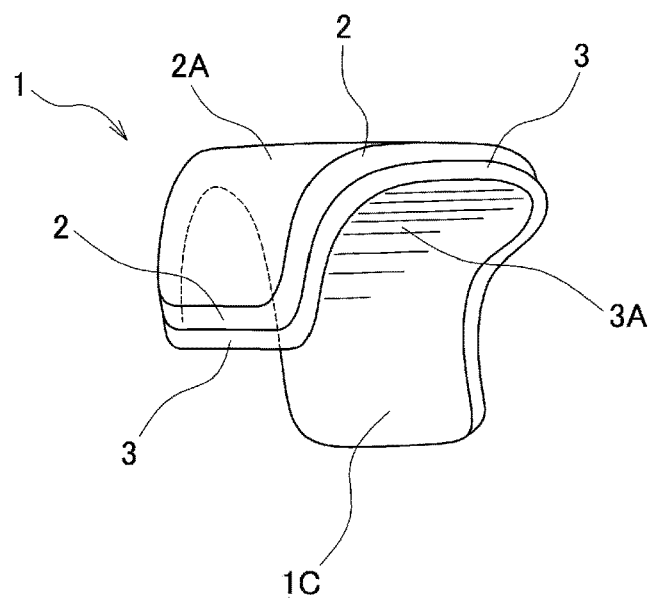
FIG. 10 is a schematic perspective view showing another example of the adhesive plaster structure of the present invention.

FIG. 10 shows a schematic perspective view showing another embodiment of the adhesive plaster structure 1 of the present invention. In the adhesive plaster structure 1 shown in FIG. 10, the guide area 3 has a J-shape in cross section, and the wound adhesion area 2 is arranged on one outer surface of the guide area 3. The adhesive plaster structure 1 shown in FIG. 10 also has the handle 1C to facilitate attaching the adhesive plaster structure 1 to the finger/toe. In the embodiment shown in FIG. 10, the handle 1C is formed integrally with the body portion, and therefore the border between the handle 1C and the body portion is not clear.

Except for the above described embodiments, various shapes can be used for the adhesive plaster structure 1 of the present invention. As long as the purpose of the present invention is attained, the positional relation between the wound adhesion area 2 and the guide area 3 and the shapes of them are not particularly limited before and after the adhesive plaster structure 1 of the present invention is attached to the finger/toe. For example, when the adhesive plaster structure of the present invention is attached to the finger/toe, the positional relation between the wound adhesion area 2 and the guide area 3 and the shapes of them can be changed or kept unchanged. For example, in one embodiment of the adhesive plaster structure 1 of the present invention, the guide area 3 can be formed in a frame body-shape having an opening, and at least a part of the wound adhesion area 2 can be arranged to cover the opening, and at least a part of the wound adhesion area 2 can penetrate through the opening to be exposed on the reverse side by receiving stress when the adhesive plaster structure 1 is attached to the finger/toe.

The adhesive plaster structure 1 of the present invention can be easily attached to the finger/toe. As long as the excellent effect of the present invention can be obtained, the method of attaching the adhesive plaster structure 1 of the present invention to the finger/toe is not particularly limited. The method of attaching the adhesive plaster structure 1 to the finger/toe can be arbitrarily selected according to the individual case such as the condition of the ingrown nail, the condition of the wound caused by the ingrown nail, and the shape of the finger/toe and the nail of the patient. In one example of attaching the adhesive plaster structure 1 of the present invention to the finger/toe, the tip portion 1A of the adhesive plaster structure 1 is inserted from the tip side of a finger/toe F along a lateral nail edge Ns, and the slide groove 3A is slid to the root side of the nail along the lateral nail edge Ns (lateral portion of the nail). Thus, the flexible wound adhesion surface 2A of the wound adhesion area 2 is guided to the position of the wound caused by an ingrown nail Fi (shown in FIG. 5A, FIG. 5B and FIG. 5C). By using the adhesive plaster structure 1 of the present invention, the flexible wound adhesion surface 2A can be surely guided to the wound Fi even when the wound Fi to be treated is located at the root portion of the nail (invisible position covered by the posterior nail fold). This is impossible in the conventional technology. Furthermore, the adhesive plaster structure of the present invention has a function of assisting to correct the ingrown nail since an effect of correcting the ingrown nail is provided by an effect of pushing up the lateral nail edge (lateral edge of the nail).

The number of the adhesive plaster structures 1 of the present invention to be attached to one finger/toe is not particularly limited. Two or more adhesive plaster structures 1 of the present invention can be simultaneously used to one finger/toe. In this case, the simultaneously used two or more adhesive plaster structures 1 can be arranged only on one side of two right and left lateral nail edges (lateral edges of the nail) or can be separately arranged on two lateral nail edges (lateral edges of the nail). The number of the adhesive plaster structures 1 arranged on one lateral nail edge (lateral edge of the nail) is not particularly limited. When two or more adhesive plaster structures 1 of the present invention are simultaneously used to one finger/toe, at least two of the adhesive plaster structures 1 can be connected with each other. The method of connecting at least two adhesive plaster structures 1 with each other is not particularly limited. For example, they can be connected with each other by an adhesive agent or the like via a separately prepared crosslinking member or the like, or can be directly connected without using the crosslinking member or the like.

Figure 11:
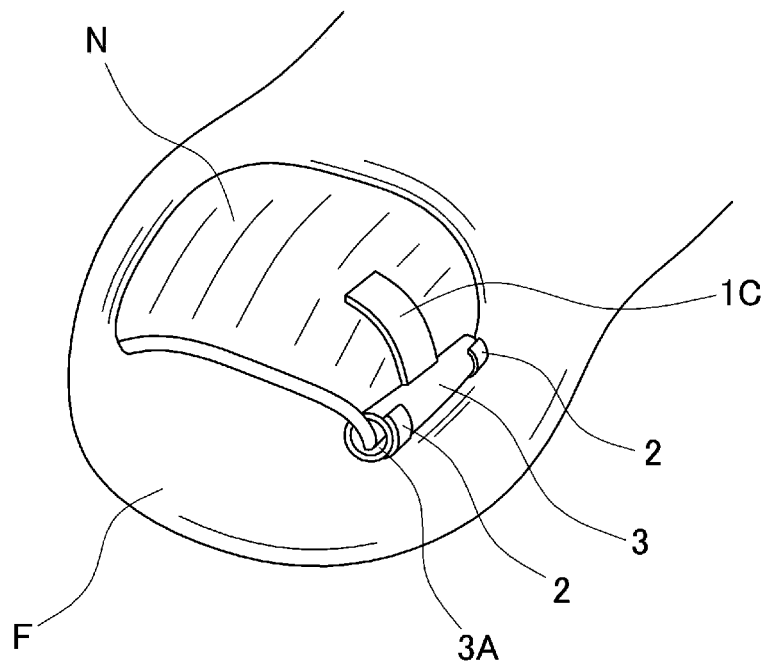
FIG. 11 is a schematic perspective view showing an example of the adhesive plaster structure of the present invention in a state of being attached to the finger/toe.

FIG. 11 shows a state that an example of the adhesive plaster structure 1 is attached to the finger/toe. The adhesive plaster structure 1 can be attached to the nail after the adhesive plaster structure 1 is attached to the finger/toe, if desired. The handle 1C can be cut after the adhesive plaster structure 1 is attached to the finger/toe, if desired. If the handle 1C is formed in a curved shape having a smaller curvature radius than that of the nail in the width direction (i.e., the direction crossing the longitudinal direction of the nail) or the handle 1C is formed in a flat plate shape, and the handle 1C is adhered to the upper side surface of the nail after the adhesive plaster structure 1 is attached to the finger/toe, the handle 1C functions like a plate spring and applies stress to pull up the lateral nail edge (lateral portion of the nail). Thus, the function of correcting the ingrown nail can be largely exhibited.

When the ingrown nail happens on a tip edge portion of the nail, not on the lateral edge portion of the nail (lateral nail edge), the adhesive plaster structure 1 of the present invention can be attached along the tip edge portion. When the ingrown nail happens both on the lateral edge portion of the nail (lateral nail edge) and the tip edge portion of the nail, at least two adhesive plaster structures 1 of the present invention can be attached along both the lateral edge portion of the nail and the tip edge portion of the nail.

Conventionally known adhesive agents can be used as an adhesive agent when adhering the adhesive plaster structure 1 to the nail and adhering the handle 1C to the upper side surface of the nail after the adhesive plaster structure 1 is attached to the finger/toe. As an example of the conventionally known adhesive agent, "Aron Alpha" (registered trademark) manufactured by Toagosei Co., Ltd. (Japan) can be listed. As an example of particularly preferred adhesive agent, Aron Alpha A "Sankyo" (registered trademark) which is an adhesive agent for medical use and manufactured by Toagosei Co., Ltd. (Japan) can be listed. Alternatively, an adhesive agent so-called "nail glue" which is generally used for attaching an artificial nail to one's own nail can be used, for example. Together with the nail glue, an activator (hardening accelerator) can be used for shortening the time required for adhesion. As a specific example of the nail glue, "ibd 5 Second Nail Glue" manufactured by shinwa Corporation (Japan) can be listed. As a specific example of the activator, "MITHOS Activator" manufactured by shinwa Corporation (Japan) can be listed.

In the embodiment where a relatively large area of the tip portion 1A side of the adhesive plaster structure 1 is formed only by the wound adhesion area 2 (e.g., absorbent cotton body and a sponge body) as shown in FIG. 1D, FIG. 1F, FIG. 1H, FIG. 1I and FIG. 1L, flexibility, bendability and softness of the tip portion 1A side may be extremely high. When attaching the adhesive plaster structure 1 of such embodiment, for example, the tip portion 1A side (e.g., absorbent cotton body and a sponge body) is firstly inserted from the tip end side of the finger/toe F along the lateral nail edge Ns so as to be stuffed (shown in FIG. 5A and other figures), and then the tip portion 1A side is further pushed to the root direction of the nail by the guide area 3 (hard body).

In the embodiment where a relatively large area of the rear end portion 1B side of the adhesive plaster structure 1 is formed only by the wound adhesion area 2 (e.g., absorbent cotton body and a sponge body) as shown in FIG. 1D, FIG. 1E, FIG. 1G, FIG. 1I and FIG. 1L, flexibility, bendability and softness of the rear end portion 1B side may be extremely high. When attaching the adhesive plaster structure 1 of such embodiment, since the guide area 3 (hard body) is located forward of the rear end portion 1B side (e.g., absorbent cotton body and a sponge body), for example, the guide area 3 (hard body) is firstly inserted from the tip end side of the finger/toe F along the lateral nail edge Ns (shown in FIG. 5A and other figures), and then the rear end portion 1B side (e.g., absorbent cotton body and a sponge body) is pulled by the guide area 3 (hard body) toward the root direction of the nail.

Figure 12A:
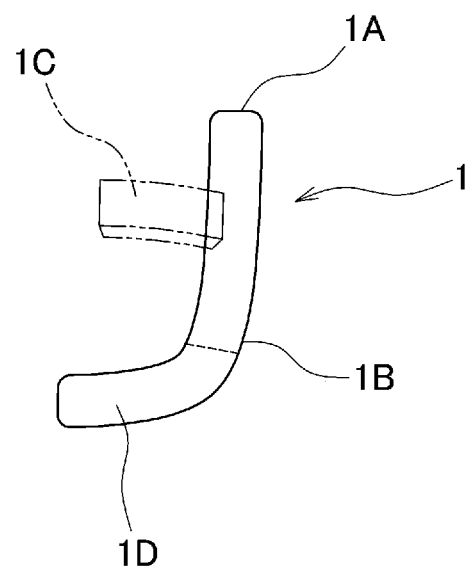
FIG. 12A is a schematic perspective view showing an example of the adhesive plaster structure of the present invention (having an extension portion for receiving a tip edge portion of the nail).
Figure 12B:
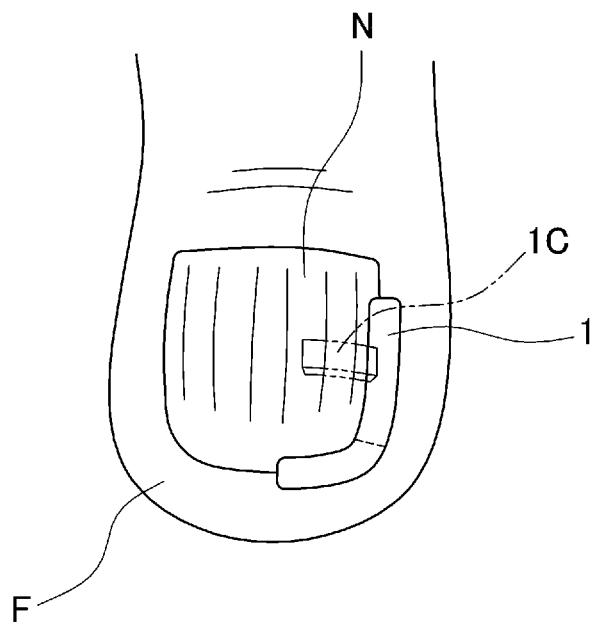
FIG. 12B is a schematic perspective view showing a state that the adhesive plaster structure shown in FIG. 12A is attached to the finger/toe.

As shown in FIG. 12A, in one embodiment of the adhesive plaster structure of the present invention, an extension portion 1D extending from the rear end portion 1B of the adhesive plaster structure 1 in a direction crossing the longitudinal direction of the adhesive plaster structure 1 is further provided, and the extension portion 1D has a groove (not illustrated) to receive the tip edge portion of the nail when the adhesive plaster structure 1 is attached to the finger/toe. Also in this embodiment, the handle 1C can be provided. In FIG. 12A, the handle 1C is indicated by two-dot chain lines. FIG. 12B shows a schematic perspective view of the embodiment of including the extension portion 1D in a state that the adhesive plaster structure 1 is attached to the finger/toe. The structure and function of the extension portion 1D are not particularly limited. The extension portion 1D can be provided with or without the structure and function same as the body portion. For example, the extension portion 1D can be provided with or without the wound adhesion area 2. The groove of the extension portion 1D can merely have a function of receiving the tip edge portion of the nail. In any case, the extension portion 1D receives the tip edge portion of the nail. Thus, the adhesive plaster structure 1 attached to the finger/toe is held more stably.

Figure 13A:
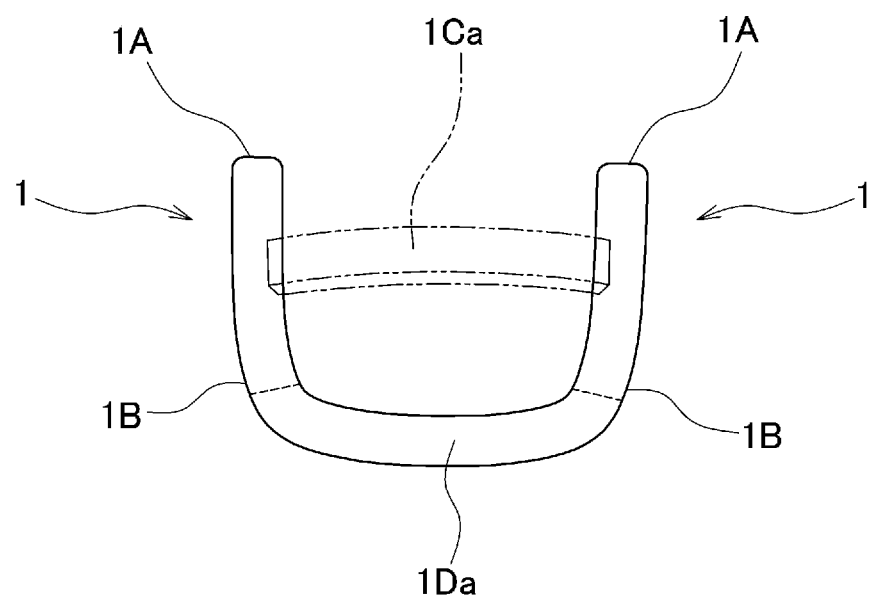
FIG. 13A is a schematic perspective view showing an example of the adhesive plaster structure of the present invention (having an extension portion for receiving a tip edge portion of the nail) attached to the finger/toe along both side edge portions of the nail.
Figure 13B:
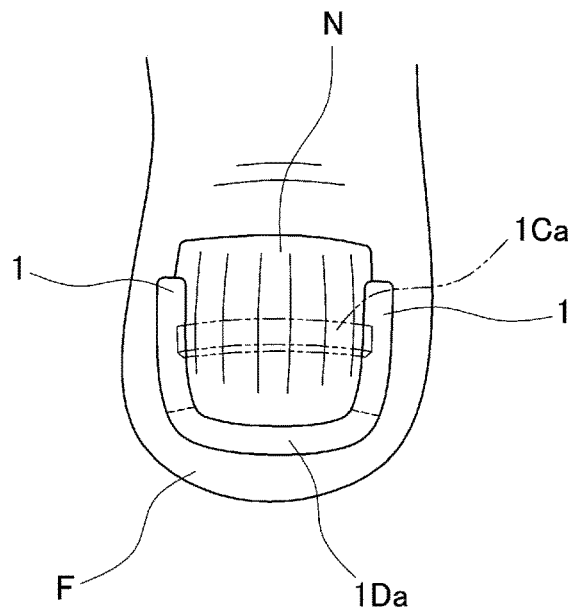
FIG. 13B is a schematic perspective view showing a state that the adhesive plaster structure shown in FIG. 13A is attached to the finger/toe.

As shown in FIG. 13A, one embodiment of the adhesive plaster structure of the present invention is a pair of adhesive plaster structures 1 attached to the finger/toe along both sides of the lateral nail edges (lateral end portions of the nail) of the nail, wherein a crosslinking extension portion 1Da extending in a direction crossing the longitudinal direction of the adhesive plaster structure 1 so as to bridge rear end portions 1B of the pair of adhesive plaster structures 1, and the extension portion 1Da has a groove (not illustrated) to receive the tip edge portion of the nail when the pair of adhesive plaster structures 1 is attached to the finger/toe. In this embodiment, a handle 1Ca (having a shape of bridging between the pair of adhesive plaster structures 1) can be provided. In FIG. 13A, the handle 1Ca is indicated by two-dot chain lines. FIG. 13B shows a schematic perspective view showing a state that the pair of adhesive plaster structures in the embodiment of having the crosslinking extension portion 1Da is attached to the finger/toe. The structure and function of the crosslinking extension portion 1Da are not particularly limited. The crosslinking extension portion 1Da can be provided with or without the structure and function same as the body portion. For example, the crosslinking extension portion 1Da can be provided with or without the wound adhesion area 2. The groove of the crosslinking extension portion 1Da can merely have a function of receiving the tip edge portion of the nail. In any case, the crosslinking extension portion 1Da receives the tip edge portion of the nail. Thus, the adhesive plaster structure 1 attached to the finger/toe is held more stably.

The size of the adhesive plaster structure of the present invention is not particularly limited. The size can be arbitrarily selected according to the size of the finger/toe having the wound to be treated, the size of the nail (especially the length of the lateral nail edge (lateral edge portion of the nail)), the position and condition of the wound to be treated and requirements of the treatment, and other conditions. However, the size of the adhesive plaster structure measured along the longitudinal direction is generally within the range of 0.5 to 120 mm. From the viewpoint of improving applicability of the adhesive plaster structure, the size is preferably within the range of 2.0 to 60 mm, and more preferably within the range of 3.0 to 20 mm. The size of the adhesive plaster structure of the present invention measured along the direction crossing the longitudinal direction is generally within the range of 0.5 to 120 mm. From the viewpoint of improving applicability of the adhesive plaster structure, the size is preferably within the range of 2.0 to 60 mm, and more preferably within the range of 3.0 to 20 mm. (The above described sizes are the size of only the body portion excluding the handle 1C and the extension portion 1D. However, when the handle 1C is integrally formed with the body portion and the border is unclear as shown in the embodiment of FIG. 10, for example, the above described sizes can be the size including the handle 1C.) The thickness of the adhesive plaster structure of the present invention (i.e., the size measured along the direction perpendicular to both the longitudinal direction of the adhesive plaster structure of the present invention and the direction crossing the longitudinal direction) is generally within the range of 0.1 to 30 mm. From the viewpoint of improving applicability of the adhesive plaster structure, the thickness is preferably within the range of 1.0 to 20 mm, and more preferably within the range of 2.0 to 15 mm. The thickness of the adhesive plaster structure of the present invention can be even or uneven.

If desired, medicine effective for healing the wound can be applied to at least one selected from the group consisting of the wound adhesion area 2 and the guide area 3 of the adhesive plaster structure of the present invention. As the application method, the conventionally known methods such as embrocation and impregnation can be used. As examples of the medicine, an inorganic antimicrobial agent (e.g., silver sulfadiazine (SSD)), an antibiotic and a nutrient of the nail (e.g., water-soluble keratin and vitamin H) can be listed. However, even when the above described medicine is not simultaneously used, the wound caused by the ingrown nail can be treated effectively, efficiently and immediately by using the adhesive plaster structure of the present invention.

When the adhesive plaster structure of the present invention is attached to the finger/toe, even severe pain of the wound is relieved almost instantly or within several seconds and the pain disappears almost completely within several minutes or several tens of minutes. In addition, healing of the wound is advanced rapidly after the attachment of the adhesive plaster structure. Normally, healing of the wound is finished within very short period, i.e., about one week to ten days. In the treatment methods of the conventional technology, on the other hand, therapeutic effect to the wound caused by the ingrown nail cannot be expected immediately (i.e., pain of the wound does not disappear immediately). It is known in this industry that sufficient healing cannot be obtained in many cases of the serious wound even if the treatment is continued for long periods (about one or two months), and it takes about two or three months to obtain sufficient healing of the wound in many cases.

Hereafter, the present invention will be explained by using examples. However, the present invention is not limited to the examples.

Example 1

By using the adhesive plaster structure having a shape shown in FIG. 10, the treatment of the wound of the ingrown nail was applied to a female patient of 24-year-old (having the ingrown nail on the big toe of the left foot).

1. Material and Dimension of Adhesive Plaster Structure

A hydrogel sheet ("Duoactive ET" (registered trademark) manufactured by ConvaTec Japan (Japan)) (thickness before swelling: 0.7 mm) was used for the material of the wound adhesion area 2 of the adhesive plaster structure, and an ABS resin was used for the material of the guide area 3. Thickness of the guide area 3: 0.5 mm. (The hydrogel sheet used here is not initially swollen and is swollen after applied to the wound by the body fluid exuded from the wound.) For adhering the wound adhesion area 2 and the guide area 3 with each other, Aron Alpha A "Sankyo" (registered trademark) which is an adhesive agent for medical use and manufactured by Toagosei Co., Ltd. (Japan) was used. The size measured along the longitudinal direction of the adhesive plaster structure was 10 mm. The size (including the handle 1C) measured along the direction crossing the longitudinal direction of the adhesive plaster structure was 14 mm, and the size of the portion where the wound adhesion area 2 exists was 8 mm.

2. Method of Treatment

The tip portion of the adhesive plaster structure was inserted from the tip end side of the nail along the lateral nail edge, and the slide groove 3A was slid toward the root direction of the nail along the lateral nail edge. Thus, the flexible wound adhesion surface 2A of the wound adhesion area 2 was guided to the position of the wound caused by the ingrown nail. The adhesive plaster structure was pushed in until whole the adhesive plaster structure reaches the root side compared to the tip end (free edge) of the nail. Then, the adhesive agent (Aron Alpha A "Sankyo" (registered trademark) manufactured by Toagosei Co., Ltd. (Japan)) was poured into between the guide area 3/the handle 1C and the upper side surface of the nail. Thus, the adhesive plaster structure was adhered to the upper side surface of the nail and fixed.

The above described attachment operation was done on the first treatment date. On the second treatment date (seven days after the first treatment date), the adhesive plaster structure was removed and the adhesive plaster structure was replaced by doing the same attachment operation again. Six days after the second treatment date, the adhesive plaster structure was naturally removed while the patient was taking a bath. On the next day (seven days after the second treatment date), the inventor observed the toe and confirmed complete healing.

3. Details of Healing Process

Figure 14A:
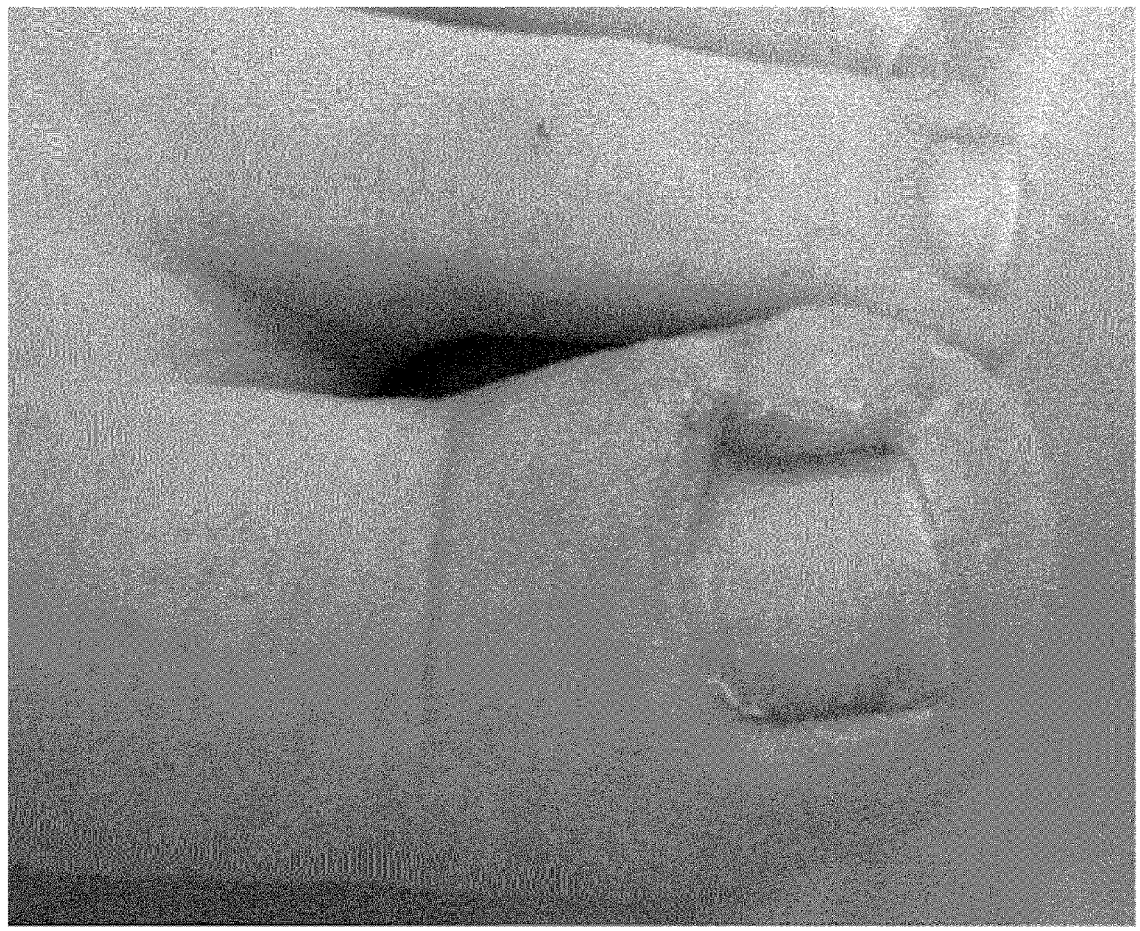
FIG. 14A is a photograph of the toe concerning the example 1 before the correction treatment of the first treatment date.
Figure 14B:
FIG. 14B is a photograph of the toe concerning the example 1 before the correction treatment of the first treatment date.

FIG. 14A and FIG. 14B show photographs of the toe before the correction treatment of the first treatment date (before attaching the adhesive plaster structure). Formation of large granuloma, redness, swelling and pain were confirmed. There was difficulty in walking.

Figure 15A:
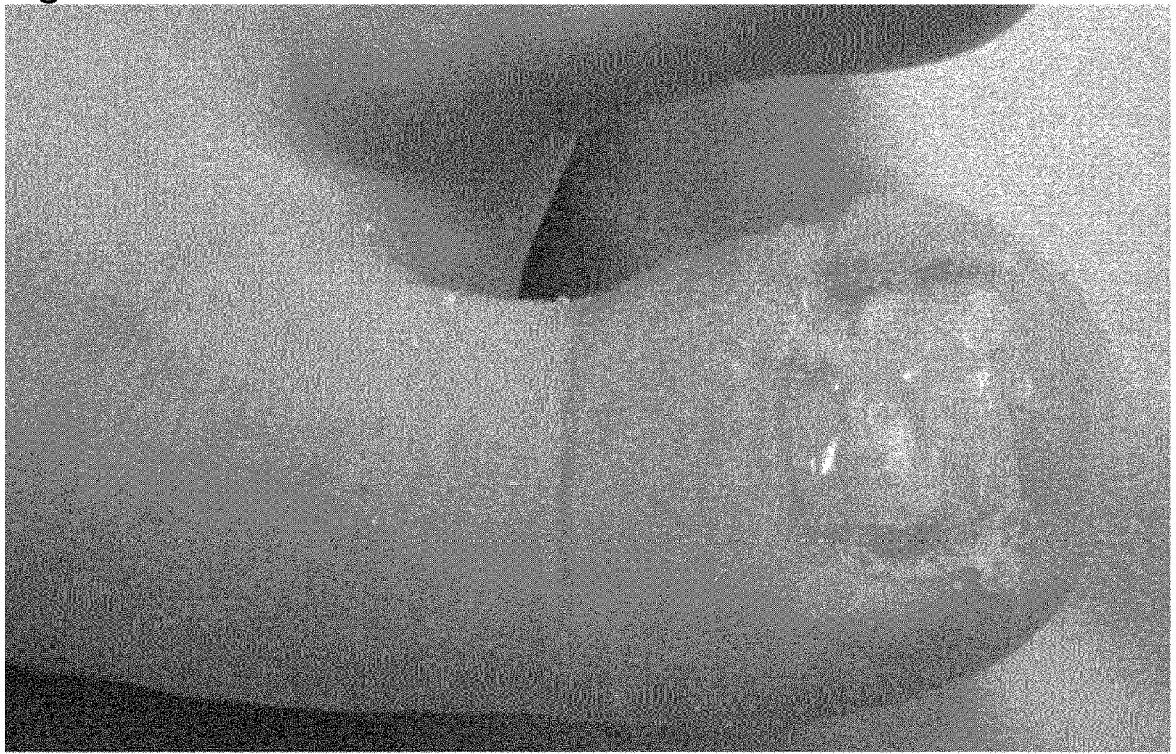
FIG. 15A is a photograph of the toe concerning the example 1 after the correction treatment of the first treatment date.
Figure 15B:
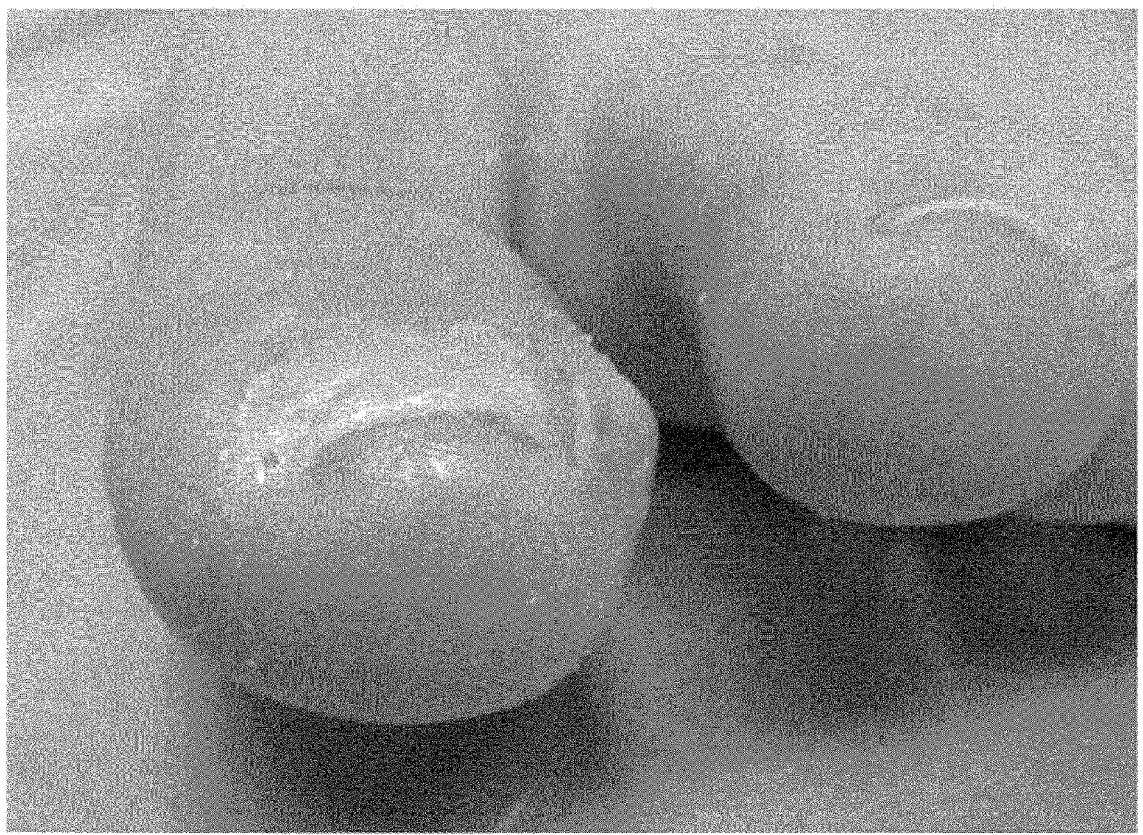
FIG. 15B is a photograph of the toe concerning the example 1 after the correction treatment of the first treatment date.

FIG. 15A and FIG. 15B show photographs of the toe after the correction treatment of the first treatment date (after attaching the adhesive plaster structure). Just after attaching the adhesive plaster structure, pain disappeared and walking was improved.

Figure 16A:
FIG. 16A is a photograph of the toe concerning the example 1 before the correction treatment of the second treatment date.
Figure 16B:
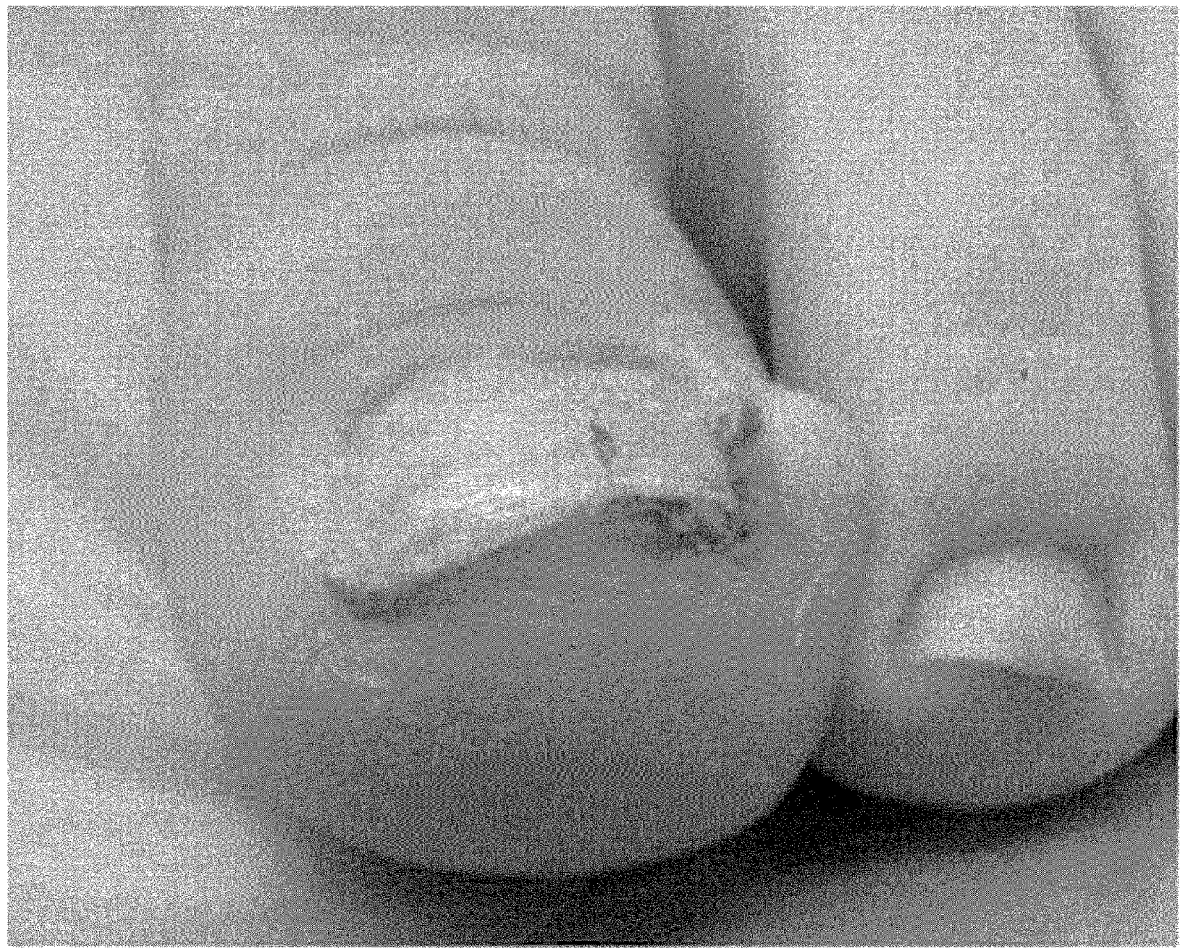
FIG. 16B is a photograph of the toe concerning the example 1 before the correction treatment of the second treatment date.

FIG. 16A and FIG. 16B show photographs of the toe before the correction treatment of the second treatment date (seven days after the first treatment date) (before replacing the adhesive plaster structure). At this point, approximately 80 percent of healing was observed. There was no pain and walking was normal.

Figure 17A:
FIG. 17A is a photograph of the toe concerning the example 1 after the correction treatment of the second treatment date.
Figure 17B:
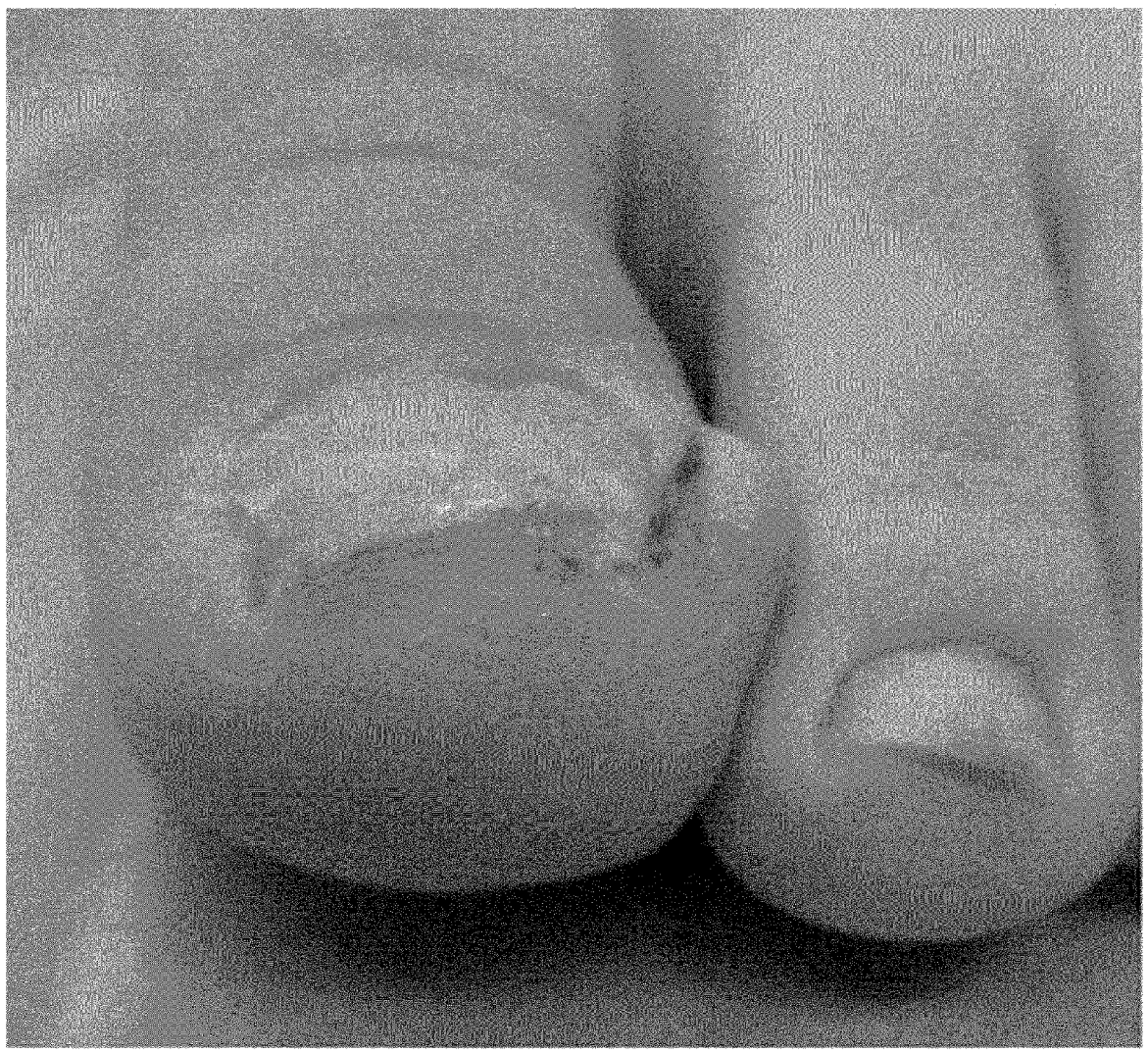
FIG. 17B is a photograph of the toe concerning the example 1 after the correction treatment of the second treatment date.

FIG. 17A and FIG. 17B show photographs of the toe after the correction treatment of the second treatment date (seven days after the first treatment date) (after replacing the adhesive plaster structure).

Figure 18A:
FIG. 18A is a photograph of the toe concerning the example 1 seven days after the correction treatment of the second treatment date.
Figure 18B:
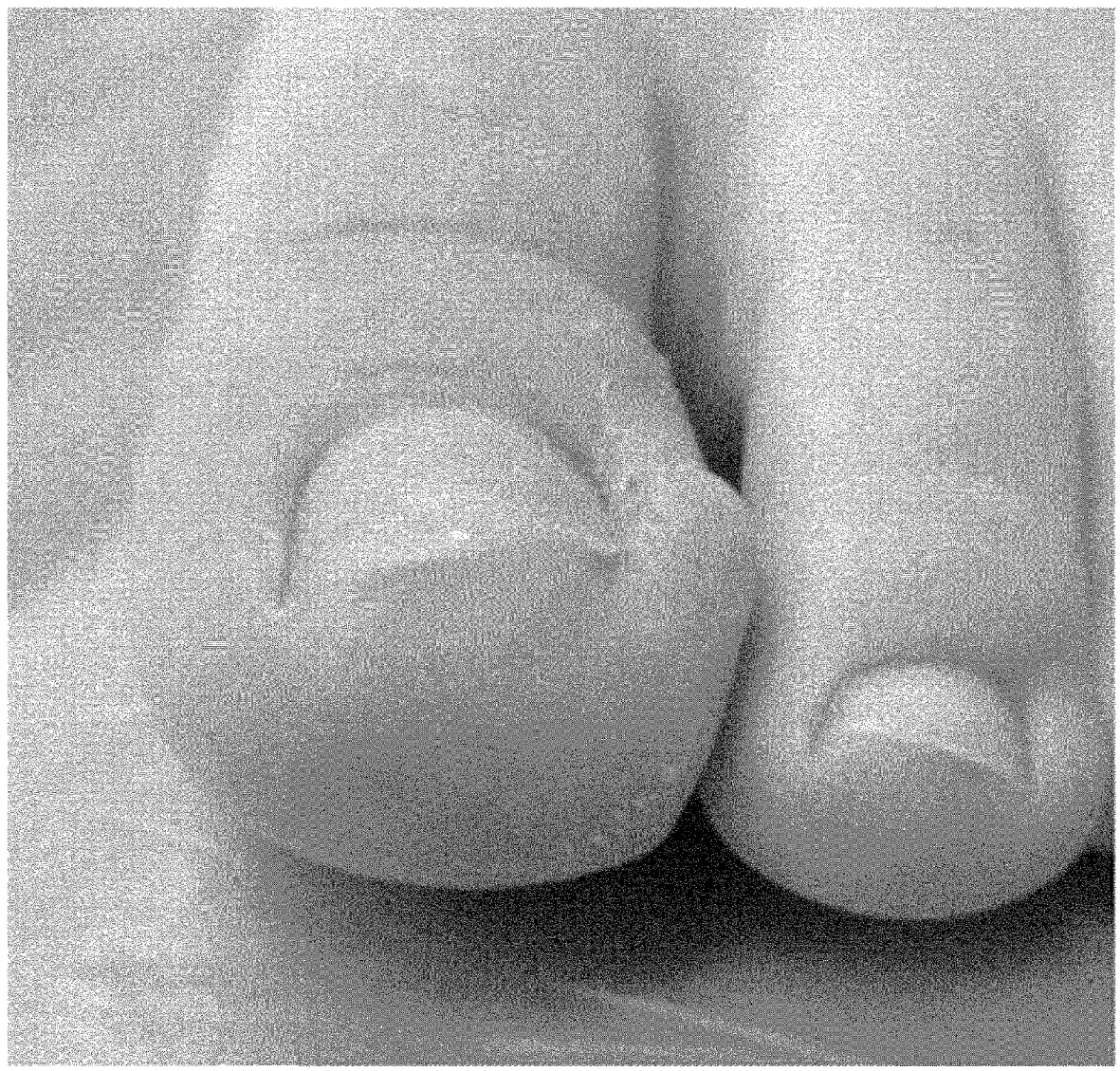
FIG. 18B is a photograph of the toe concerning the example 1 seven days after the correction treatment of the second treatment date.

FIG. 18A and FIG. 18B show photographs of the toe seven days after the correction treatment of the second treatment date. The symptoms were completely cured except for that a little swelling was left. It is presumed that the symptoms were completely cured within two or three days after the second treatment date (i.e., nine to ten days after the first treatment date).

Example 2

By using the adhesive plaster structure substantially same as that of the example 1, the treatment of the wound of the ingrown nail was applied to a female patient of 20-year-old (having the ingrown nail on the big toe of the left foot) by the same operation as the first treatment date of the example 1.

Seven days after the treatment date, the inventor observed the toe and confirmed complete healing.

(Details of Healing Process)

Figure 19A:
FIG. 19A is a photograph of the toe concerning the example 2 before the correction treatment of the treatment date.
Figure 19B:
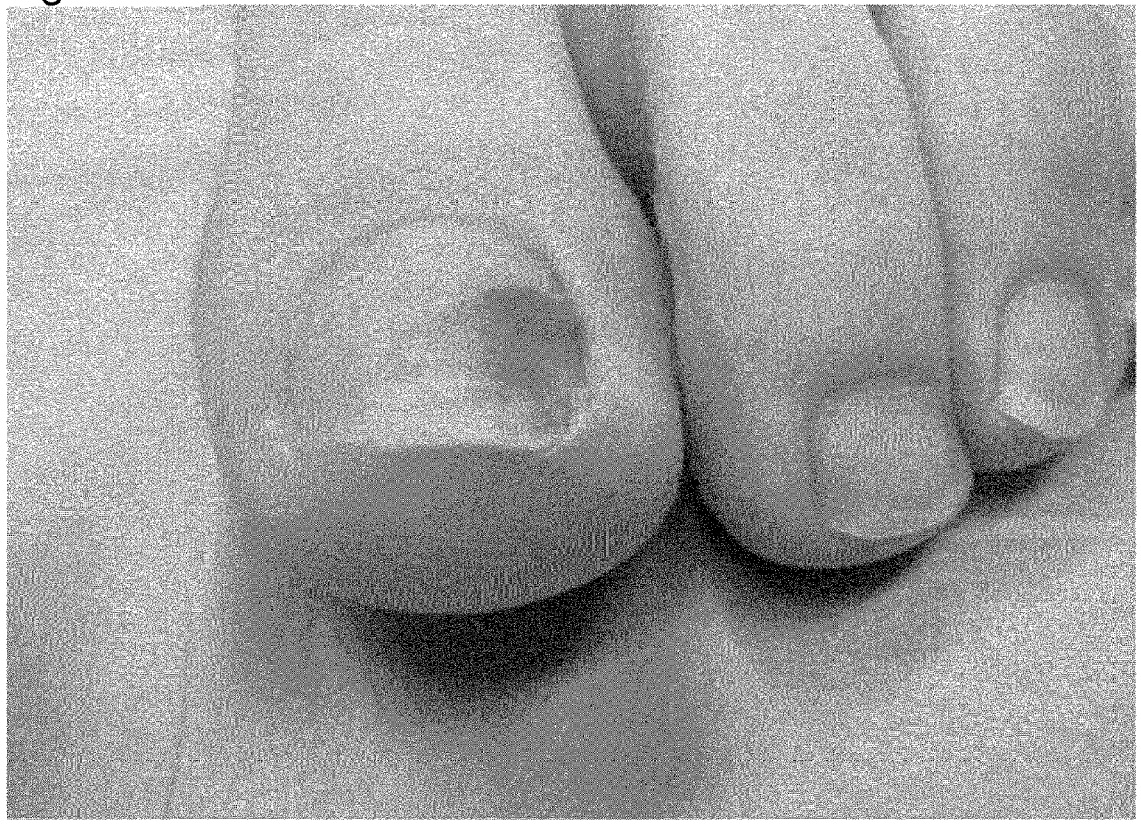
FIG. 19B is a photograph of the toe concerning the example 2 before the correction treatment of the treatment date.

FIG. 19A and FIG. 19B show photographs of the toe before the correction treatment of the treatment date (before attaching the adhesive plaster structure). Severe pain, internal bleeding, inflammation and formation of granuloma were confirmed. There was difficulty in walking.

Figure 20A:
FIG. 20A is a photograph of the toe concerning the example 2 after the correction treatment of the treatment date.
Figure 20B:
FIG. 20B is a photograph of the toe concerning the example 2 after the correction treatment of the treatment date.

FIG. 20A and FIG. 20B show photographs of the toe after the correction treatment of the treatment date (after attaching the adhesive plaster structure). Just after attaching the adhesive plaster structure, pain disappeared and walking was improved.

Figure 21A:
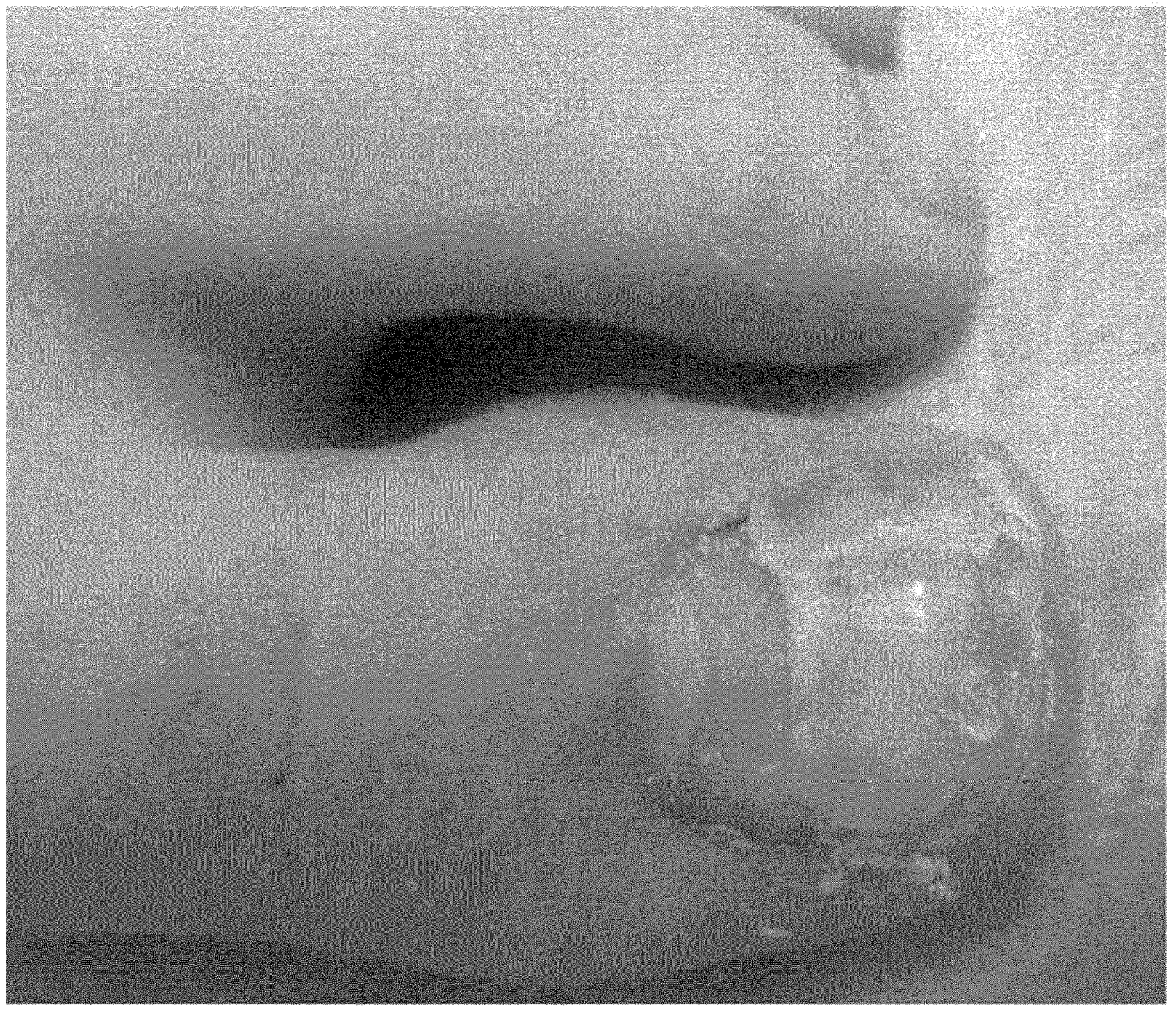
FIG. 21A is a photograph of the toe concerning the example 2 seven days after the correction treatment of the treatment date and before removing the adhesive plaster structure.
Figure 21B:
FIG. 21B is a photograph of the toe concerning the example 2 seven days after the correction treatment of the treatment date and before removing the adhesive plaster structure.

FIG. 21A and FIG. 21B show photographs of the toe seven days after the correction treatment of the treatment date and before removing the adhesive plaster structure.

Figure 22A:
FIG. 22A is a photograph of the toe concerning the example 2 seven days after the correction treatment of the treatment date and after removing the adhesive plaster structure.
Figure 22B:
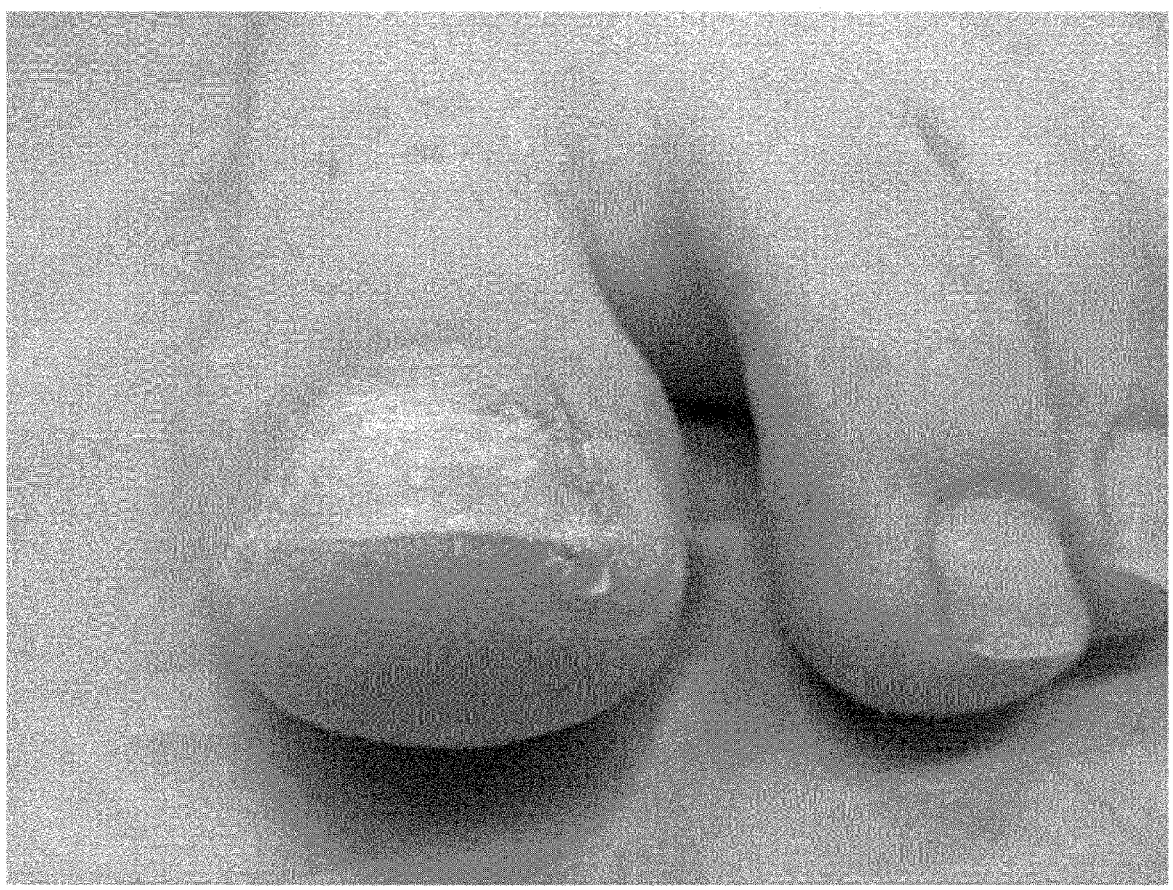
FIG. 22B is a photograph of the toe concerning the example 2 seven days after the correction treatment of the treatment date and after removing the adhesive plaster structure.

FIG. 22A and FIG. 22B show photographs of the toe seven days after the correction treatment of the treatment date and after removing the adhesive plaster structure. The symptoms were completely cured.

Example 3

By using the adhesive plaster structure substantially same as that of the example 1, the treatment of wound of the ingrown nail was applied to a female patient of 27-year-old (having the ingrown nail on the big toe of the left foot) by the same operation as the first treatment date of the example 1. However, since the patient of the example 3 had the wound on both lateral nail edges (lateral edge portions of the nail) of both sides of the big toe of the left foot, two (a pair of) adhesive plaster structures having a linearly symmetric shape (i.e., having a mirror image relationship to each other) were used. The pair of adhesive plaster structures were attached to both sides of the finger/toe one by one, and adhered/fixed to the upper side surface of the nail by an adhesive agent. At that time, the handles 1C of both adhesive plaster structures are overlapped with each other at the upper side surface of the nail and adhered/fixed to each other by an adhesive agent.

Seven days after the treatment date, the inventor observed the toe and confirmed almost complete healing.

(Details of Healing Process)

Figure 23A:
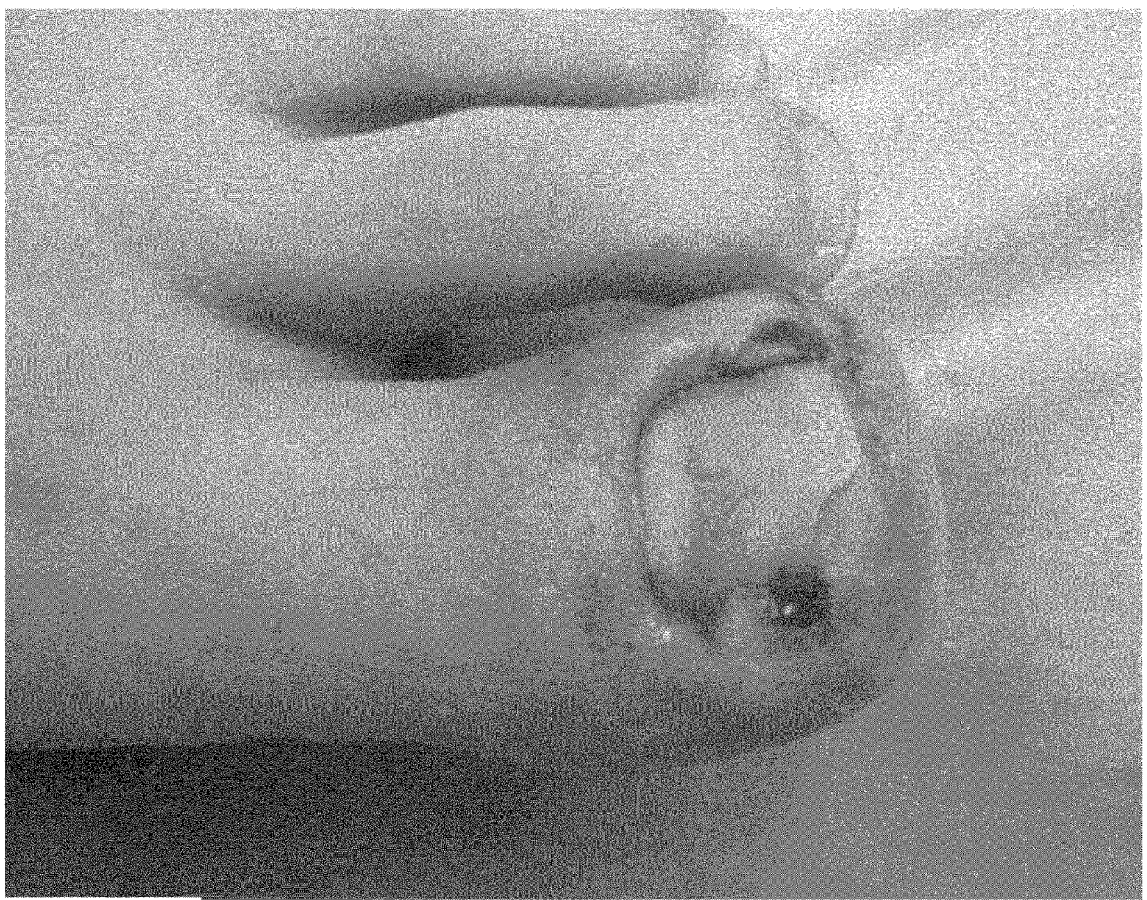
FIG. 23A is a photograph of the toe concerning the example 3 before the correction treatment of the treatment date.
Figure 23B:
FIG. 23B is a photograph of the toe concerning the example 3 before the correction treatment of the treatment date.

FIG. 23A and FIG. 23B show photographs of the toe before the correction treatment of the treatment date (before attaching the adhesive plaster structure). Absence of the nail, severe pain, internal bleeding, inflammation, swelling and formation of granuloma were confirmed. There was difficulty in walking.

Figure 24A:
FIG. 24A is a photograph of the toe concerning the example 3 after the correction treatment of the treatment date.
Figure 24B:
FIG. 24B is a photograph of the toe concerning the example 3 after the correction treatment of the treatment date.

FIG. 24A and FIG. 24B show photographs of the toe after the correction treatment of the treatment date (after attaching the adhesive plaster structure). Just after attaching the adhesive plaster structure, pain disappeared and walking was improved.

Figure 25A:
FIG. 25A is a photograph of the toe concerning the example 3 seven days after the correction treatment of the treatment date and before removing the adhesive plaster structure.
Figure 25B:
FIG. 25B is a photograph of the toe concerning the example 3 seven days after the correction treatment of the treatment date and before removing the adhesive plaster structure.

FIG. 25A and FIG. 25B show photographs of the toe seven days after the correction treatment of the treatment date and before removing the adhesive plaster structure.

Figure 26A:
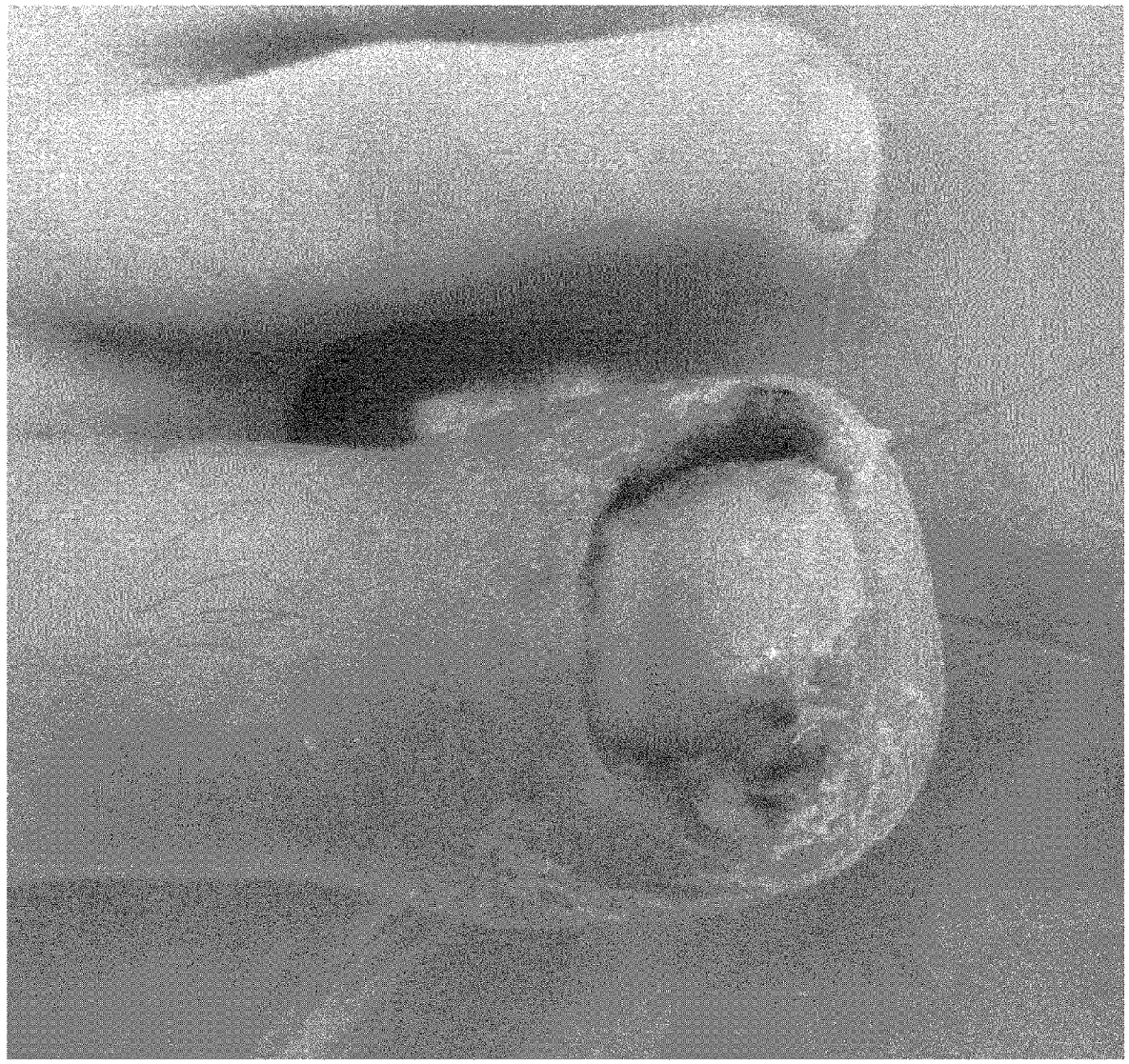
FIG. 26A is a photograph of the toe concerning the example 3 seven days after the correction treatment of the treatment date and after removing the adhesive plaster structure.
Figure 26B:
FIG. 26B is a photograph of the toe concerning the example 3 seven days after the correction treatment of the treatment date and after removing the adhesive plaster structure.

FIG. 26A and FIG. 26B show photographs of the toe seven days after the correction treatment of the treatment date and after removing the adhesive plaster structure. The symptoms were almost completely cured. The inflammation almost disappeared and epithelialization had almost completed at the part of the granuloma. It was clear that symptoms would be completely cured within several days by natural healing.

Comparative Example 1

By using the tool having a similar structure as that of the example 1 except for that the wound adhesion area 2 is not provided, the treatment of the wound of the ingrown nail was applied to a male patient of 45-year-old (having the ingrown nail on the big toe of the left foot) by the same operation as the first treatment date of the example 1. The condition of the wound of the ingrown nail before treatment was almost same as the example 1. The replacement of the tool and disinfection of the affected area were periodically repeated (approximately once a week). The above described treatment was continued for about two months.

(Details of Healing Process)

After about two months from the beginning of the treatment, the degree of healing was approximately 50%. There was still difficulty in walking. Although pain was slightly relieved after about one week from when the tool was firstly attached (beginning of the treatment), the pain didn't disappear. The pain was still confirmed after about two months had passed.

INDUSTRIAL APPLICABILITY

When the adhesive plaster structure of the present invention is attached to the finger/toe, because of the function of the slide groove 3A of the guide area 3, the flexible wound adhesion surface 2A of the wound adhesion area 2 is surely guided to the position of the wound caused by the ingrown nail. When the adhesive plaster structure of the present invention is used, because of a linkage between the wound adhesion area 2 and the guide area 3, the wound of the ingrown nail can be surely treated also near the root of the nail in addition to near the tip of the nail regardless of degree of the deformation of the ingrown nail and severity of pain of the wound caused by the ingrown nail. In the conventional technology, the root of the nail could not be treated effectively and efficiently. By using the present invention, the wound caused by the ingrown nail can be treated effectively and efficiently and pain of the wound caused by the ingrown nail can be relieved rapidly and drastically. (Namely, the wound can be immediately cured.) Furthermore, the adhesive plaster structure of the present invention has a function of assisting to correct the ingrown nail since an effect of correcting the ingrown nail is provided by an effect of pushing up the lateral nail edge (lateral edge of the nail).

DESCRIPTION OF REFERENCE SIGNS

1: adhesive plaster structure
1A: tip portion of adhesive plaster structure
1B: rear end portion of adhesive plaster structure
1C: an example of handle of adhesive plaster structure
1Ca: another example of adhesive plaster structure
1D: an example of extension portion extended from rear end portion of adhesive plaster structure in direction crossing longitudinal direction
1Da: another example of extension portion extended from rear end portion of adhesive plaster structure in direction crossing longitudinal direction
1E: overhang portion for holding adhesive plaster structure on finger/toe
2: wound adhesion area
2A: flexible wound adhesion surface
2B: two edge portions of wound adhesion area to cover two edge portions extending in longitudinal direction of guide area
2C: overhang portion for covering and protecting granuloma
3: guide area
3A: slide groove
3B: two edge portions extending in longitudinal direction of guide area
F: finger/toe of patient
Fi: wound caused by ingrown nail
Fg: granuloma caused by influence of wound
G: gap between wound adhesion area and guide area
N: nail
Ns: lateral nail edge (lateral edge portion of nail)

What is claimed is:

1. An adhesive plaster structure configured to attach to a finger or a toe along a lateral nail edge for treating a wound neighboring an ingrown nail, the adhesive plaster structure comprising:

(i) a wound adhesion area having a flexible wound adhesion surface to be adhered to the wound neighboring the ingrown nail; and (ii) a guide area having a slide groove that is configured to receive the lateral nail edge, the slide groove configured to slide in a longitudinal direction of a nail along the lateral nail edge, wherein the wound adhesion area is formed by a soft body and has a first solid structure, the guide area is formed by a hard body and has a second solid structure, the adhesive plaster structure has an approximately rod shape, when an end portion of the adhesive plaster structure adapted to be located at a root side of the finger or the toe is defined as a tip portion and an end portion of the adhesive plaster structure adapted to be located at a tip side of the finger or the toe is defined as a rear end portion in a state that the adhesive plaster structure is attached to the finger or the toe, the slide groove extends at least over a part of a length between the tip portion and the rear end portion of the adhesive plaster structure in the longitudinal direction of the adhesive plaster structure, the flexible wound adhesion surface is arranged between the lateral nail edge and the wound neighboring the ingrown nail in a state that the slide groove receives the lateral nail edge when the adhesive plaster structure is attached to the finger or the toe, the wound adhesion area is disposed concentrically around a side of the guide area opposite of the slide groove such that the flexible wound adhesion surface of the wound adhesion area follows a same contour of and is oriented identically to the guide area, the guide area and the disposed wound adhesion area are arranged together as a single component physically defined at least by the first and second solid structures of the wound adhesion area and the guide area, respectively, wherein the guide area and the wound adhesion area are configured to attach to the finger or the toe as the single component, the guide area configured to guide the flexible wound adhesion surface of the wound adhesion area, as the single component, to a position of the wound caused by the ingrown nail as the adhesive plaster structure is being attached to the finger or the toe such that the flexible wound adhesion surface is: (i) submerged under the lateral nail edge and (ii) enclosed by flesh of the finger or the toe after the adhesive plaster structure has been attached to the finger or the toe.

2. The adhesive plaster structure according to claim 1, wherein the soft body of the wound adhesion area is selected from the group consisting of a hydrogel body, a gauze, a woven fabric, a nonwoven fabric, an absorbent cotton body, a rubber body, a foamed polyurethane body, a sponge body, a fiber body, a resin body having high flexibility and a material body having a property of absorbing and storing body fluid by a porous structure and/or an uneven structure, and the hard body of the guide area is selected from the group consisting of a resin body having low flexibility, a metal body having low flexibility, a hard pulp body, a glass body, a stone material body and a ceramic body.

3. The adhesive plaster structure according to claim 1, further comprising:

a handle to facilitate attaching the adhesive plaster structure to the finger or the toe.

4. The adhesive plaster structure according to claim 1, further comprising:

an extension portion extending from the rear end portion of the adhesive plaster structure in a direction crossing the longitudinal direction of the adhesive plaster structure, wherein the extension portion has a groove to receive a tip edge portion of the ingrown nail when the adhesive plaster structure is attached to the finger or the toe.

5. The adhesive plaster structure according to claim 1, wherein a longitudinal extent of the adhesive plaster structure is configured to extend in the longitudinal direction of the ingrown nail along the lateral nail edge when the adhesive plaster structure is attached to the finger or the toe.

6. The adhesive plaster structure according to claim 1, wherein the soft body of the wound adhesion area has a defined shape and thickness and the wound adhesion area has a positional relation with the guide area.

* * * * *